US012410238B2

(12) United States Patent
Moran et al.

(10) Patent No.: US 12,410,238 B2
(45) Date of Patent: Sep. 9, 2025

(54) MONOCLONAL ANTIBODIES AGAINST JC VIRUS

(71) Applicant: Icahn School of Medicine at Mount Sinai, New York, NY (US)

(72) Inventors: Thomas Moran, New York, NY (US); Thomas Kraus, New York, NY (US); J. Andrew Duty, New York, NY (US); Domenico Tortorella, New York, NY (US)

(73) Assignee: ICAHN School of Medicine at Mount Sinai, New York, NY (US)

( * ) Notice: Subject to any disclaimer, the term of this patent is extended or adjusted under 35 U.S.C. 154(b) by 816 days.

(21) Appl. No.: 17/620,496

(22) PCT Filed: Jun. 19, 2020

(86) PCT No.: PCT/US2020/038708
§ 371 (c)(1),
(2) Date: Dec. 17, 2021

(87) PCT Pub. No.: WO2020/257633
PCT Pub. Date: Dec. 24, 2020

(65) Prior Publication Data
US 2022/0356228 A1 Nov. 10, 2022

Related U.S. Application Data

(60) Provisional application No. 62/863,433, filed on Jun. 19, 2019.

(51) Int. Cl.
| | |
|---|---|
| *C07K 16/08* | (2006.01) |
| *A61P 25/28* | (2006.01) |
| *A61P 31/20* | (2006.01) |
| *C12N 15/63* | (2006.01) |

(52) U.S. Cl.
CPC .............. *C07K 16/08* (2013.01); *C12N 15/63* (2013.01); *A61P 25/28* (2018.01); *A61P 31/20* (2018.01); *C07K 16/084* (2013.01); *C07K 2317/21* (2013.01); *C07K 2317/24* (2013.01); *C07K 2317/56* (2013.01); *C07K 2317/565* (2013.01); *C07K 2317/76* (2013.01)

(58) Field of Classification Search
CPC ................ C07K 16/08; C07K 2317/24; C07K 2317/565; C07K 16/084; C07K 2317/21; C07K 2317/56; C07K 2317/76; C07K 2317/92; C12N 15/63; A61P 25/28; A61P 31/20
See application file for complete search history.

(56) References Cited

U.S. PATENT DOCUMENTS

| | | |
|---|---|---|
| 9,567,391 B2 | 2/2017 | Simon et al. |
| 2010/0008851 A1 | 1/2010 | Nicolaides et al. |
| 2011/0263827 A1 | 10/2011 | Ghayur et al. |

FOREIGN PATENT DOCUMENTS

| | | |
|---|---|---|
| WO | 2013/142299 A1 | 9/2013 |
| WO | 2014/002035 A2 | 1/2014 |
| WO | 2014/102399 A1 | 7/2014 |
| WO | 2017/046676 A1 | 3/2017 |

OTHER PUBLICATIONS

International Search Report and Written Opinion mailed Dec. 17, 2020 for related International Application No. PCT/US20/38708, 16 pages.
Chen, Gang et al., "Synthetic antibodies and peptides recognizing progressive multifocal leukoencephalopathy-specific point mutations in polyomavirus JC capsid viral protein 1", MABS, vol. 7, No. 4, Apr. 16, 2015, pp. 681-692.
Extended European Search Report mailed Mar. 10, 2023, in European Application No. 20825849.1, 19 pages.
Partial supplementary European search report mailed Nov. 15, 2022, for European application No. 20825849.1, 17 pages.

*Primary Examiner* — Misook Yu
*Assistant Examiner* — Alec Jon Peters
(74) *Attorney, Agent, or Firm* — Fox Rothschild LLP

(57) ABSTRACT

Provided herein are monoclonal antibodies and antigen-binding fragments thereof that bind to the John Cunningham virus. Also provided are pharmaceutical compositions comprising the monoclonal antibodies and antigen-binding fragments thereof, as well as methods of using such monoclonal antibodies and antigen-binding fragments thereof, including methods for the treatment and/or prevention of JCV infections and/or progressive multifocal leukoencephalopathy.

Figure 1:
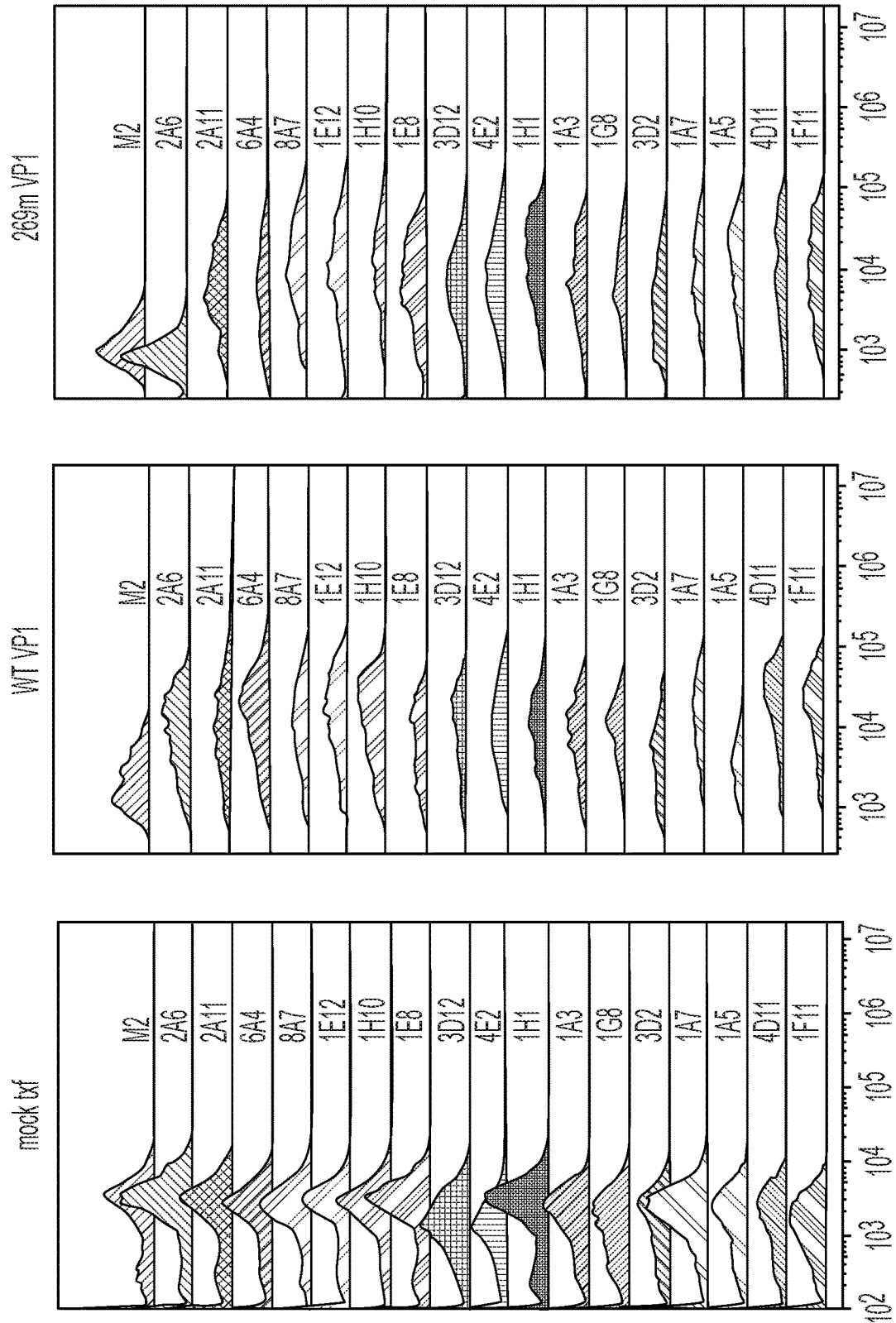
Figure 1:
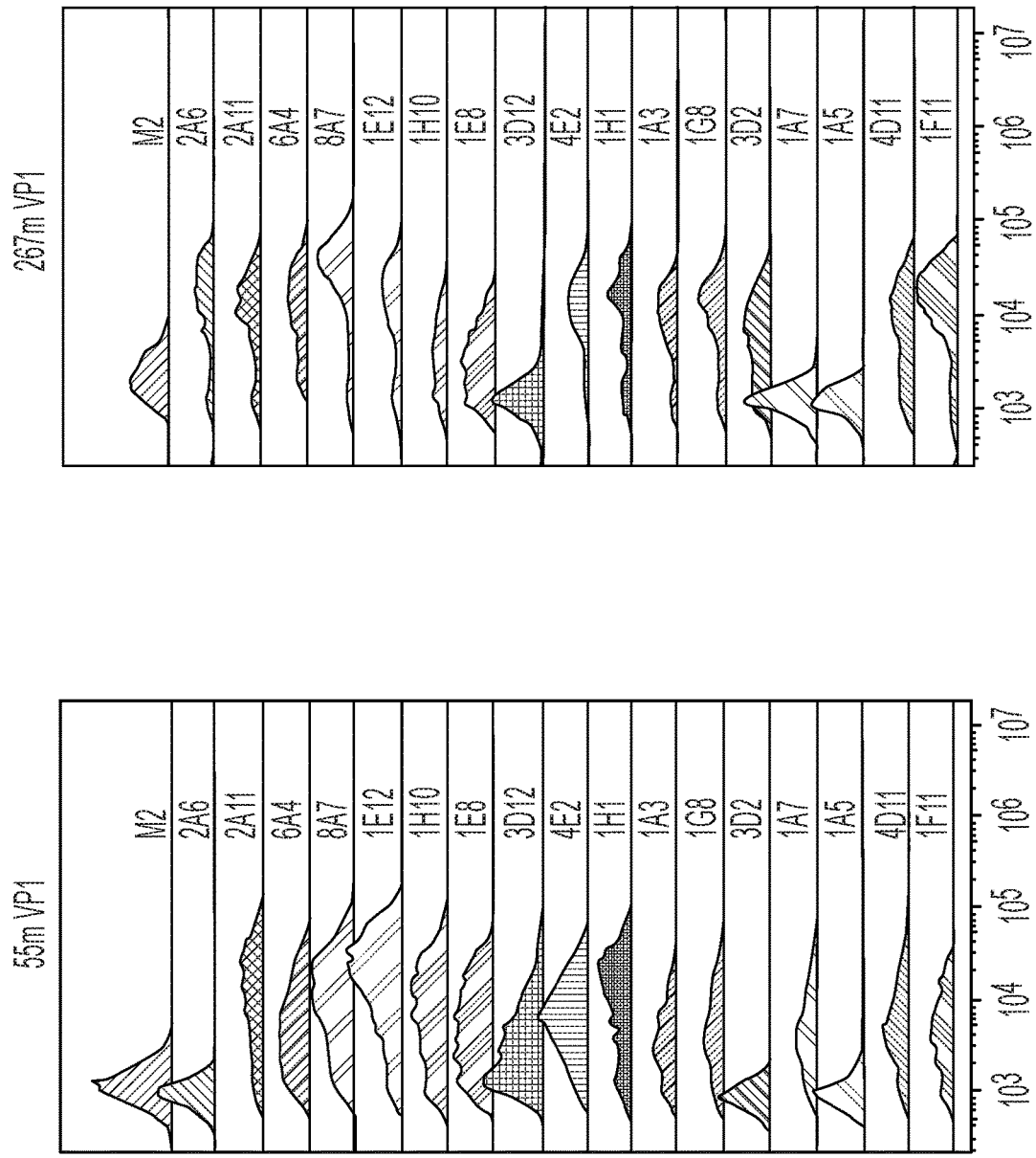

28 Claims, 3 Drawing Sheets
Specification includes a Sequence Listing.

MONOCLONAL ANTIBODIES AGAINST JC VIRUS

CROSS-REFERENCE TO RELATED APPLICATIONS

The present application is a National Stage Application under 35 U.S.C. § 371 of International Application No. PCT/US2020/038708 filed Jun. 19, 2020, which claims the benefit of priority to U.S. Provisional Patent Application Ser. No. 62/863,433 filed Jun. 19, 2019, the disclosures of all of which are hereby incorporated by reference in their entireties.

FIELD OF THE INVENTION

The disclosure relates generally to the field of molecular biology and medicine. More particularly, the disclosure provides monoclonal antibodies and antigen-binding fragments thereof that bind to the John Cunningham virus and pharmaceutical compositions thereof, as well as methods of using such monoclonal antibodies and antigen-binding fragments thereof, including methods for the treatment and/or prevention of JCV infections and/or progressive multifocal leukoencephalopathy.

REFERENCE TO A SEQUENCE LISTING

This application contains a Sequence Listing, which has been submitted electronically in txt format and is hereby incorporated by reference in its entirety. Said txt copy, created on Dec. 16, 2021, is named 084284_00244_ST25.txt and is 79,539 bytes in size.

BACKGROUND

The John Cunningham virus (JCV), a member of the polyomavirus family, is present in 60-80% of the population, where it is primarily located within the kidneys. Although persistent, the virus is usually well-controlled by the immune system and an infection is typically not apparent clinically. However, in patients with immune deficiencies, the virus may disseminate into glia cells such as oligodendrocytes and astrocytes in the brain and cause progressive multifocal leukoencephalopathy (PML), a debilitating and fatal demyelinating disease. Once a virus infection is established in the brain, it can spread to other susceptible cells causing myelin destruction and cell death. No antiviral therapy to date has shown efficacy against JCV/PML, which remains an essentially untreatable brain infection.

Patients with hereditary immune deficiencies that are susceptible to the development of PML include, for example, patients with common variable immune deficiency (CVID), severe combined immune deficiency (SCID), Wiskott-Aldrich syndrome (WAS), adenosine deaminase (ADA) deficiency, and hyper IgM syndrome.

PML also frequently develops in patients with acquired immune deficiencies, such as in patients with B cell lymphoproliferative disease including chronic lymphocytic leukemia and Hodgkin's lymphoma or in individuals infected with the human immunodeficiency virus (HIV).

Before the development of antiretroviral therapy, the incidence of PML in acquired immune deficiency syndrome (AIDS) patients ranged from 7-10%. While treatments to restore immunity in HIV infected patients have reduced the incidence of PML significantly, in some instances, antiretroviral therapy unmasks a JCV infection not previously identified in the patient. The ensuing immune response can cause a severe and life-threatening disease called Immune Reconstitution Inflammatory Syndrome (IRIS). While the incidence of PML in AIDS patients has been reduced, patients that develop PML have a poor prognosis and no proven treatments are available. As such, PML remains a major concern and cause of mortality in HIV patients.

Further, in patients that are immunosuppressed due to treatment for an autoimmune disease (including multiple sclerosis (MS) or lupus), cancer, after receiving a transplant, or for any other cause of compromised immunity, the development of PML continues to be a life-threatening problem. For instance, while treatment of MS with natalizumab, a humanized monoclonal antibody against the cell adhesion molecule α4-integrin, is very effective, the risk of developing PML is quite high (1 in 44), with a mortality rate approaching 25%. Cases of PML have been reported to occur during treatment with, for example, TNF alpha inhibitors, and virtually every treatment associated with immunosuppression.

Currently, the main treatment option for PML patients is to restore immunity when possible, e.g. by removal of the immunosuppressive agent. However, in addition to the return of disease symptoms, the restored cellular immune response can attack infected sites in the brain causing IRIS. As such, compositions and methods of preventing and treating PML are urgently needed.

SUMMARY

Provided herein are monoclonal anti-JCV antibodies and antigen-binding fragments thereof that bind to JCV, including to mutant versions of JCV. Also provided are compositions and methods for using one or more of the anti-JCV antibodies and antigen-binding fragments thereof disclosed herein for treating a subjected infected with JCV, both prophylactically and therapeutically.

In some aspects, the disclosure provides an antibody or antigen-binding fragment thereof which binds to JCV, the antibody or antigen-binding fragment thereof comprising a heavy chain variable region and a light chain variable region, wherein the heavy chain variable region comprises three CDRs (CDR1H, CDR2H, and CDR3H), and wherein the light chain variable region comprises three CDRs (CDR1L, CDR2L, and CDR3L).

In one aspect, the disclosure provides an antibody or antigen-binding fragment thereof which binds JCV, wherein:

CDR1H comprises the sequence $X_1X_2TFSDX_3Y$ (SEQ ID NO:56);
wherein $X_1$ is G or E;
wherein $X_2$ is F or I;
wherein $X_3$ is H, L, Y, or F;
CDR2H comprises the sequence $ISX_4X_5GX_6X_7I$ (SEQ ID NO:58);
wherein $X_4$ is T or F;
wherein $X_5$ is S or G;
wherein $X_6$ is R or S;
wherein $X_7$ is T or A;
CDR3H comprises the sequence $AX_8DX_9YDNX_{10}GWX_{11}Y$ (SEQ ID NO:61);
wherein $X_8$ is G or S;
wherein $X_9$ is Y or F;
wherein $X_{10}$ is S or V;
wherein $X_{11}$ is D, E, Y, or N;

CDR1L comprises the sequence QSLX$_{25}$YSDGNTY (SEQ ID NO:65);
   wherein X$_{25}$ is V, I or L;
   CDR2L comprises the sequence KVS; and
   CDR3L comprises the sequence MQGX$_{26}$HWPRT (SEQ ID NO:67);
   wherein X$_{26}$ is T, S or A.

In one aspect, the disclosure provides an antibody or antigen-binding fragment thereof which binds JCV, wherein:
   CDR1H comprises the sequence X$_1$X$_2$TFSDX$_3$Y (SEQ ID NO:56);
   wherein X$_1$ is G or E;
   wherein X$_2$ is F or I;
   wherein X$_3$ is H, L, Y, or F;
   CDR2H comprises the sequence ISX$_4$X$_5$GX$_6$X$_7$I (SEQ ID NO:58);
   wherein X$_4$ is T or F;
   wherein X$_5$ is S or G;
   wherein X$_6$ is R or S;
   wherein X$_7$ is T or A;
   CDR3H comprises the sequence AX$_8$DX$_9$YDNX$_{10}$GWX$_{11}$Y (SEQ ID NO:61);
   wherein X$_8$ is G or S;
   wherein X$_9$ is Y or F;
   wherein X$_{10}$ is S or V;
   wherein X$_{11}$ is D, E, Y, or N;
   CDR1L comprises the sequence QSLX$_{12}$YSDGNTY (SEQ ID NO:64);
   wherein X$_{12}$ is V or I;
   CDR2L comprises the sequence KVS; and
   CDR3L comprises the sequence MQGX$_{13}$HWPRT (SEQ ID NO:66);
   wherein X$_{13}$ is T or S.

In one embodiment, the disclosure provides an antibody or antigen-binding fragment thereof which binds to JCV, wherein CDR1H of the antibody or antigen-binding fragment thereof comprises SEQ ID NO: 1, CDR2H comprises SEQ ID NO:12, CDR3H comprises SEQ ID NO:23, CDR1L comprises SEQ ID NO:36, CDR2L comprises the sequence KVS, and CDR3L comprises SEQ ID NO:45. In one embodiment, the antibody or antigen-binding fragment thereof further comprises a heavy chain variable region that comprises a sequence that is at least 90% identical to SEQ ID NO:69, and a light chain variable region that comprises a sequence that is at least 90% identical to SEQ ID NO:70.

In one embodiment, the disclosure provides an antibody or antigen-binding fragment thereof which binds to JCV, wherein CDR1H of the antibody or antigen-binding fragment thereof comprises SEQ ID NO:2, CDR2H comprises SEQ ID NO:12, CDR3H comprises SEQ ID NO:24, CDR1L comprises SEQ ID NO:36, CDR2L comprises the sequence KVS, and CDR3L comprises SEQ ID NO:45. In one embodiment, the antibody or antigen-binding fragment thereof further comprises a heavy chain variable region that comprises a sequence that is at least 90% identical to SEQ ID NO:71, and a light chain variable region that comprises a sequence that is at least 90% identical to SEQ ID NO:72.

In one embodiment, the disclosure provides an antibody or antigen-binding fragment thereof which binds to JCV, wherein CDR1H of the antibody or antigen-binding fragment thereof comprises SEQ ID NO:3, CDR2H comprises SEQ ID NO:12, CDR3H comprises SEQ ID NO:25, CDR1L comprises SEQ ID NO:36, CDR2L comprises the sequence KVS, and CDR3L comprises SEQ ID NO:45. In one embodiment, the antibody or antigen-binding fragment thereof further comprises a heavy chain variable region that comprises a sequence that is at least 90% identical to SEQ ID NO:73, and a light chain variable region that comprises a sequence that is at least 90% identical to SEQ ID NO:74.

In one embodiment, the disclosure provides an antibody or antigen-binding fragment thereof which binds to JCV, wherein CDR1H of the antibody or antigen-binding fragment thereof comprises SEQ ID NO:3, CDR2H comprises SEQ ID NO:12, CDR3H comprises SEQ ID NO:26, CDR1L comprises SEQ ID NO:36, CDR2L comprises the sequence KVS, and CDR3L comprises SEQ ID NO:45. In one embodiment, the antibody or antigen-binding fragment thereof further comprises a heavy chain variable region that comprises a sequence that is at least 90% identical to SEQ ID NO:75, and a light chain variable region that comprises a sequence that is at least 90% identical to SEQ ID NO:76.

In one embodiment, the disclosure provides an antibody or antigen-binding fragment thereof which binds to JCV, wherein CDR1H of the antibody or antigen-binding fragment thereof comprises SEQ ID NO:3, CDR2H comprises SEQ ID NO:13, CDR3H comprises SEQ ID NO:27, CDR1L comprises SEQ ID NO:36, CDR2L comprises the sequence KVS, and CDR3L comprises SEQ ID NO:46. In one embodiment, the antibody or antigen-binding fragment thereof further comprises a heavy chain variable region that comprises a sequence that is at least 90% identical to SEQ ID NO:77, and a light chain variable region that comprises a sequence that is at least 90% identical to SEQ ID NO:78.

In one embodiment, the disclosure provides an antibody or antigen-binding fragment thereof which binds to JCV, wherein CDR1H of the antibody or antigen-binding fragment thereof comprises SEQ ID NO:3, CDR2H comprises SEQ ID NO:14, CDR3H comprises SEQ ID NO:28, CDR1L comprises SEQ ID NO:37, CDR2L comprises the sequence KVS, and CDR3L comprises SEQ ID NO:45. In one embodiment, the antibody or antigen-binding fragment thereof further comprises a heavy chain variable region that comprises a sequence that is at least 90% identical to SEQ ID NO:79, and a light chain variable region that comprises a sequence that is at least 90% identical to SEQ ID NO:80.

In one embodiment, the disclosure provides an antibody or antigen-binding fragment thereof which binds to JCV, wherein CDR1H of the antibody or antigen-binding fragment thereof comprises SEQ ID NO:3, CDR2H comprises SEQ ID NO:12, CDR3H comprises SEQ ID NO:26, CDR1L comprises SEQ ID NO:36, CDR2L comprises the sequence KVS, and CDR3L comprises SEQ ID NO:45. In one embodiment, the antibody or antigen-binding fragment thereof further comprises a heavy chain variable region that comprises a sequence that is at least 90% identical to SEQ ID NO:81, and a light chain variable region that comprises a sequence that is at least 90% identical to SEQ ID NO:82.

In one embodiment, the disclosure provides an antibody or antigen-binding fragment thereof which binds to JCV, wherein CDR1H of the antibody or antigen-binding fragment thereof comprises SEQ ID NO:4, CDR2H comprises SEQ ID NO:15, CDR3H comprises SEQ ID NO:28, CDR1L comprises SEQ ID NO:36, CDR2L comprises the sequence KVS, and CDR3L comprises SEQ ID NO:45. In one embodiment, the antibody or antigen-binding fragment thereof further comprises a heavy chain variable region that comprises a sequence that is at least 90% identical to SEQ ID NO:83, and a light chain variable region that comprises a sequence that is at least 90% identical to SEQ ID NO:84.

In one embodiment, the disclosure provides an antibody or antigen-binding fragment thereof which binds to JCV, wherein CDR1H of the antibody or antigen-binding fragment thereof comprises SEQ ID NO:3, CDR2H comprises SEQ ID NO:12, CDR3H comprises SEQ ID NO:28, CDR1L comprises SEQ ID NO:38, CDR2L comprises the sequence KVS, and CDR3L comprises SEQ ID NO:47. In one embodiment, the antibody or antigen-binding fragment thereof further comprises a heavy chain variable region that comprises a sequence that is at least 90% identical to SEQ ID NO:99, and a light chain variable region that comprises a sequence that is at least 90% identical to SEQ ID NO:100.

In one embodiment, the disclosure provides an antibody or antigen-binding fragment thereof which binds to JCV, wherein CDR1H of the antibody or antigen-binding fragment thereof comprises SEQ ID NO:5, CDR2H comprises SEQ ID NO:12, CDR3H comprises SEQ ID NO:23, CDR1L comprises SEQ ID NO:36, CDR2L comprises the sequence KVS, and CDR3L comprises SEQ ID NO:45. In one embodiment, the antibody or antigen-binding fragment thereof further comprises a heavy chain variable region that comprises a sequence that is at least 90% identical to SEQ ID NO:101, and a light chain variable region that comprises a sequence that is at least 90% identical to SEQ ID NO:102.

In one aspect, the disclosure provides an antibody or antigen-binding fragment thereof which binds to the John Cunningham virus (JCV), wherein:
CDR1H comprises SEQ ID NO:6;
CDR2H comprises SEQ ID NO:16;
CDR3H comprises the sequence ARRGFEQQLSYYYYYGX$_{14}$DV (SEQ ID NO:62);
wherein X$_{14}$ is L or M;
CDR1L comprises SEQ ID NO:39;
CDR2L comprises the sequence WAS;
CDR3L comprises the sequence QQYYX$_{15}$X$_{16}$PWT (SEQ ID NO:68);
wherein X$_{15}$ is T or S; and
wherein X$_{16}$ is T or F.

In one embodiment, the disclosure provides an antibody or antigen-binding fragment thereof which binds to JCV, wherein CDR1H of the antibody or antigen-binding fragment thereof comprises SEQ ID NO:6, CDR2H comprises SEQ ID NO:16, CDR3H comprises SEQ ID NO:29, CDR1L comprises SEQ ID NO:39, CDR2L comprises the sequence WAS and CDR3L comprises SEQ ID NO:48. In one embodiment, the antibody or antigen-binding fragment thereof further comprises a heavy chain variable region that comprises a sequence that is at least 90% identical to SEQ ID NO:85, and a light chain variable region that comprises a sequence that is at least 90% identical to SEQ ID NO:86.

In one embodiment, the disclosure provides an antibody or antigen-binding fragment thereof which binds to JCV, wherein CDR1H of the antibody or antigen-binding fragment thereof comprises SEQ ID NO:6, CDR2H comprises SEQ ID NO:16, CDR3H comprises SEQ ID NO:30, CDR1L comprises SEQ ID NO:39, CDR2L comprises the sequence WAS, and CDR3L comprises SEQ ID NO:49. In one embodiment, the antibody or antigen-binding fragment thereof further comprises a heavy chain variable region that comprises a sequence that is at least 90% identical to SEQ ID NO:88, and a light chain variable region that comprises a sequence that is at least 90% identical to SEQ ID NO:89.

In one aspect, the disclosure provides an antibody or antigen-binding fragment thereof which binds to the John Cunningham virus (JCV), wherein:
CDR1H comprises the sequence GYTFTX$_{17}$YD (SEQ ID NO:57);
wherein X$_{17}$ is F or N;
CDR2H comprises the sequence X$_{23}$NPNSGNX$_{24}$ (SEQ ID NO:60);
wherein X$_{23}$ is M, V, or T;
wherein X$_{24}$ is T or S;
CDR3H comprises the sequence ARKIWVGX$_{20}$TX$_{21}$FDX$_{22}$ (SEQ ID NO:63);
wherein X$_{20}$ is H or T;
wherein X$_{21}$ is T or I;
wherein X$_{22}$ is R or Y;
CDR1L comprises SEQ ID NO:40 or SEQ ID NO:41;
CDR2L comprises the sequence AAS or sequence AVS;
CDR3L comprises SEQ ID NO:50, SEQ ID NO:51, or SEQ ID NO:52.

In one aspect, the disclosure provides an antibody or antigen-binding fragment thereof which binds to the John Cunningham virus (JCV), wherein:
CDR1H comprises the sequence GYTFTX$_{17}$YD (SEQ ID NO:57);
wherein X$_{17}$ is F or N;
CDR2H comprises the sequence X$_{18}$NPNSGNX$_{19}$ (SEQ ID NO:59);
wherein X$_{18}$ is M or V;
wherein X$_{19}$ is T or S;
CDR3H comprises the sequence ARKIWVGX$_{20}$TX$_{21}$FDX$_{22}$ (SEQ ID NO:63);
wherein X$_{20}$ is H or T;
wherein X$_{21}$ is T or I;
wherein X$_{22}$ is R or Y;
CDR1L comprises SEQ ID NO:40 or SEQ ID NO:41;
CDR2L comprises the sequence AAS or sequence AVS;
CDR3L comprises SEQ ID NO:50 or SEQ ID NO:51.

In one embodiment, the disclosure provides an antibody or antigen-binding fragment thereof which binds to JCV, wherein CDR1H of the antibody or antigen-binding fragment thereof comprises SEQ ID NO:7, CDR2H comprises SEQ ID NO:17, CDR3H comprises SEQ ID NO:31, CDR1L comprises SEQ ID NO:40, CDR2L comprises the sequence AAS, and CDR3L comprises SEQ ID NO:50. In one embodiment, the antibody or antigen-binding fragment thereof further comprises a heavy chain variable region that comprises a sequence that is at least 90% identical to SEQ ID NO:89, and a light chain variable region that comprises a sequence that is at least 90% identical to SEQ ID NO:90.

In one embodiment, the disclosure provides an antibody or antigen-binding fragment thereof which binds to JCV, wherein CDR1H of the antibody or antigen-binding fragment thereof comprises SEQ ID NO:8, CDR2H comprises SEQ ID NO:18, CDR3H comprises SEQ ID NO:32, CDR1L comprises SEQ ID NO:41, CDR2L comprises the sequence AAS, and CDR3L comprises SEQ ID NO:51. In one embodiment, the antibody or antigen-binding fragment thereof further comprises a heavy chain variable region that comprises a sequence that is at least 90% identical to SEQ ID NO:91, and a light chain variable region that comprises a sequence that is at least 90% identical to SEQ ID NO:92.

In one embodiment, the disclosure provides an antibody or antigen-binding fragment thereof which binds to JCV, wherein CDR1H of the antibody or antigen-binding fragment thereof comprises SEQ ID NO:8, CDR2H comprises SEQ ID NO:19, CDR3H comprises SEQ ID NO:32, CDR1L comprises SEQ ID NO:41, CDR2L comprises the sequence AVS, and CDR3L comprises SEQ ID NO:52. In one embodiment, the antibody or antigen-binding fragment thereof further comprises a heavy chain variable region that comprises a sequence that is at least 90% identical to SEQ ID NO:103, and a light chain variable region that comprises a sequence that is at least 90% identical to SEQ ID NO:104.

In one aspect, the disclosure provides an antibody or antigen-binding fragment thereof which binds to the John Cunningham virus (JCV), wherein:

CDR1H comprises SEQ ID NO:9, SEQ ID NO:10, or SEQ ID NO:11;

CDR2H comprises SEQ ID NO:20, SEQ ID NO:21, or SEQ ID NO:22;

CDR3H comprises SEQ ID NO:33, SEQ ID NO:34, or SEQ ID NO:35;

CDR1L comprises SEQ ID NO:42, SEQ ID NO:43, or SEQ ID NO:44;

CDR2L comprises the sequence WAS, sequence GAS, or sequence GTS; and

CDR3L comprises SEQ ID NO:53, SEQ ID NO:54, or SEQ ID NO:55.

In one embodiment, the disclosure provides an antibody or antigen-binding fragment thereof which binds to JCV, wherein CDR1H of the antibody or antigen-binding fragment thereof comprises SEQ ID NO:9, CDR2H comprises SEQ ID NO:20, CDR3H comprises SEQ ID NO:33, CDR1L comprises SEQ ID NO:42, CDR2L comprises the sequence WAS, and CDR3L comprises SEQ ID NO:53. In one embodiment, the antibody or antigen-binding fragment thereof further comprises a heavy chain variable region that comprises a sequence that is at least 90% identical to SEQ ID NO:93, and a light chain variable region that comprises a sequence that is at least 90% identical to SEQ ID NO:94.

In one embodiment, the disclosure provides an antibody or antigen-binding fragment thereof which binds to JCV, wherein CDR1H of the antibody or antigen-binding fragment thereof comprises SEQ ID NO: 10, CDR2H comprises SEQ ID NO:21, CDR3H comprises SEQ ID NO:34, CDR1L comprises SEQ ID NO:43, CDR2L comprises the sequence GAS, and CDR3L comprises SEQ ID NO:54. In one embodiment, the antibody or antigen-binding fragment thereof further comprises a heavy chain variable region that comprises a sequence that is at least 90% identical to SEQ ID NO:95, and a light chain variable region that comprises a sequence that is at least 90% identical to SEQ ID NO:96.

In one embodiment, the disclosure provides an antibody or antigen-binding fragment thereof which binds to JCV, wherein CDR1H of the antibody or antigen-binding fragment thereof comprises SEQ ID NO: 11, CDR2H comprises SEQ ID NO:22, CDR3H comprises SEQ ID NO:35, CDR1L comprises SEQ ID NO:44, CDR2L comprises the sequence GTS, and CDR3L comprises SEQ ID NO:55. In one embodiment, the antibody or antigen-binding fragment thereof further comprises a heavy chain variable region that comprises a sequence that is at least 90% identical to SEQ ID NO:97, and a light chain variable region that comprises a sequence that is at least 90% identical to SEQ ID NO:98.

In one aspect, the disclosure provides an antibody or antigen-binding fragment thereof which binds to the John Cunningham virus (JCV), wherein: the heavy chain variable region comprises SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, or SEQ ID NO:103; and the light chain variable region comprises SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, or SEQ ID NO:98; SEQ ID NO:100, SEQ ID NO:102, or SEQ ID NO:104.

In one embodiment, the disclosure provides an antibody or antigen-binding fragment thereof which binds to JCV, wherein the heavy chain variable region of the antibody or antigen-binding fragment thereof comprises SEQ ID NO:69 and the light chain variable region comprises SEQ ID NO:70.

In one embodiment, the disclosure provides an antibody or antigen-binding fragment thereof which binds to JCV, wherein the heavy chain variable region of the antibody or antigen-binding fragment thereof comprises SEQ ID NO:71 and the light chain variable region comprises SEQ ID NO:72.

In one embodiment, the disclosure provides an antibody or antigen-binding fragment thereof which binds to JCV, wherein the heavy chain variable region of the antibody or antigen-binding fragment thereof comprises SEQ ID NO:73 and the light chain variable region comprises SEQ ID NO:74.

In one embodiment, the disclosure provides an antibody or antigen-binding fragment thereof which binds to JCV, wherein the heavy chain variable region of the antibody or antigen-binding fragment thereof comprises SEQ ID NO:75 and the light chain variable region comprises SEQ ID NO:76.

In one embodiment, the disclosure provides an antibody or antigen-binding fragment thereof which binds to JCV, wherein the heavy chain variable region of the antibody or antigen-binding fragment thereof comprises SEQ ID NO:77 and the light chain variable region comprises SEQ ID NO:78.

In one embodiment, the disclosure provides an antibody or antigen-binding fragment thereof which binds to JCV, wherein the heavy chain variable region of the antibody or antigen-binding fragment thereof comprises SEQ ID NO:79 and the light chain variable region comprises SEQ ID NO:80.

In one embodiment, the disclosure provides an antibody or antigen-binding fragment thereof which binds to JCV, wherein the heavy chain variable region of the antibody or antigen-binding fragment thereof comprises SEQ ID NO:81 and the light chain variable region comprises SEQ ID NO:82.

In one embodiment, the disclosure provides an antibody or antigen-binding fragment thereof which binds to JCV, wherein the heavy chain variable region of the antibody or antigen-binding fragment thereof comprises SEQ ID NO:83 and the light chain variable region comprises SEQ ID NO:84.

In one embodiment, the disclosure provides an antibody or antigen-binding fragment thereof which binds to JCV, wherein the heavy chain variable region of the antibody or antigen-binding fragment thereof comprises SEQ ID NO:85 and the light chain variable region comprises SEQ ID NO:86.

In one embodiment, the disclosure provides an antibody or antigen-binding fragment thereof which binds to JCV, wherein the heavy chain variable region of the antibody or antigen-binding fragment thereof comprises SEQ ID NO:87 and the light chain variable region comprises SEQ ID NO:88.

In one embodiment, the disclosure provides an antibody or antigen-binding fragment thereof which binds to JCV, wherein the heavy chain variable region of the antibody or antigen-binding fragment thereof comprises SEQ ID NO:89 and the light chain variable region comprises SEQ ID NO:90.

In one embodiment, the disclosure provides an antibody or antigen-binding fragment thereof which binds to JCV, wherein the heavy chain variable region of the antibody or antigen-binding fragment thereof comprises SEQ ID NO:91 and the light chain variable region comprises SEQ ID NO:92.

In one embodiment, the disclosure provides an antibody or antigen-binding fragment thereof which binds to JCV, wherein the heavy chain variable region of the antibody or antigen-binding fragment thereof comprises SEQ ID NO:93 and the light chain variable region comprises SEQ ID NO:94.

In one embodiment, the disclosure provides an antibody or antigen-binding fragment thereof which binds to JCV, wherein the heavy chain variable region of the antibody or antigen-binding fragment thereof comprises SEQ ID NO:95 and the light chain variable region comprises SEQ ID NO:96.

In one embodiment, the disclosure provides an antibody or antigen-binding fragment thereof which binds to JCV, wherein the heavy chain variable region of the antibody or antigen-binding fragment thereof comprises SEQ ID NO:97 and the light chain variable region comprises SEQ ID NO:98.

In one embodiment, the disclosure provides an antibody or antigen-binding fragment thereof which binds to JCV, wherein the heavy chain variable region of the antibody or antigen-binding fragment thereof comprises SEQ ID NO:99 and the light chain variable region comprises SEQ ID NO:100.

In one embodiment, the disclosure provides an antibody or antigen-binding fragment thereof which binds to JCV, wherein the heavy chain variable region of the antibody or antigen-binding fragment thereof comprises SEQ ID NO:101 and the light chain variable region comprises SEQ ID NO:102.

In one embodiment, the disclosure provides an antibody or antigen-binding fragment thereof which binds to JCV, wherein the heavy chain variable region of the antibody or antigen-binding fragment thereof comprises SEQ ID NO:103 and the light chain variable region comprises SEQ ID NO:104.

In some embodiments, the anti-JCV antibody or antigen-binding fragment thereof disclosed herein is a chimeric antibody, a CDR-grafted antibody, or a humanized antibody or antigen-binding fragment thereof.

In some embodiments, the anti-JCV antibody or antigen-binding fragment thereof disclosed herein is a multispecific or a bispecific antibody or antigen-binding fragment thereof.

In some embodiments, the anti-JCV antibody or antigen-binding fragment thereof disclosed herein is an scFv, Fv, Fab', Fab, F(ab')$_2$, or diabody.

In some embodiments, the anti-JCV antibody or antigen-binding fragment thereof disclosed herein is has isotype IgG1, IgG2a, or IgG2b.

In some embodiments, the anti-JCV antibody or antigen-binding fragment thereof disclosed herein contains a S241P substitution in the constant region of the heavy chain.

In some embodiments, the antibody or antigen-binding fragment thereof disclosed herein is deglycosylated.

In some embodiments, the anti-JCV antibody or antigen-binding fragment thereof disclosed herein is lacking a C-terminal lysine in the heavy chain.

In some embodiments, the anti-JCV antibody or antigen-binding fragment thereof disclosed herein is conjugated to one or more of a cytotoxin, a fluorescent label, and an imaging agent.

The disclosure also provides nucleic acid molecules or a set of nucleic acid molecules encoding the anti-JCV antibodies and antigen-binding fragments thereof disclosed herein, as well as cells comprising such nucleic acids. In some embodiments, the nucleic acids encoding the anti-JCV antibodies and antigen-binding fragments thereof disclosed herein are isolated nucleic acids.

In one embodiment, the disclosure provides a vector comprising a nucleic acid encoding an anti-JCV antibody or antigen-binding fragment thereof disclosed herein. In one embodiment, the disclosure provides a cell comprising a vector disclosed herein. In one embodiment, the cell comprising a vector disclosed herein is a CHO or HEK293 cell. In one embodiment, the cell comprising a vector disclosed herein expresses an anti-JCV antibody or antigen-binding fragment thereof disclosed herein.

The disclosure also provides methods of inhibiting the binding of JCV to a cell, neutralizing JCV, reducing the replication of JCV, preventing the infection of a cell by JCV, and/or reducing the internalization of JCV by a cell, the methods comprising contacting JCV with one or more of the anti-JCV antibodies or antigen-binding fragments thereof disclosed herein. In some embodiments, the JCV is wild type JCV. In other embodiments, the JCV comprises a VP1 protein with an amino acid sequence consisting essentially of SEQ ID NO:141, wherein the VP1 protein contains one or more mutations at positions 55, 60, 61, 122, 265, 267, 269, 271, and 283 of SEQ ID NO:141, and/or wherein the VP1 protein contains one or more deletions at position 50-51 or 123-125. In some embodiments, the JCV comprises a VP1 mutant with a L55F, an S267F, and/or an S269F mutation.

```
SEQ ID NO: 141 (JCV virus VP1 protein):
MAPTKRKGERKDPVQVPKLLIRGGVEVLEVKTGVDSITEVECFLTPEMG

DPDEHLRGFSKSISISDTFESDSPNRDMLPCYSVARIPLPNLNEDLTCG

NILMWEAVTLKTEVIGVTSLMNVHSNGQATHDNGAGKPVQGTSFHFFSV

GGEALELQGVLFNYRTKYPDGTIFPKNATVQSQVMNTEHKAYLDKNKAY

PVECWVPDPTRNENTRYFGTLTGGENVPPVLHITNTATTVLLDEFGVGP

LCKGDNLYLSAVDVCGMFTNRSGSQQWRGLSRYFKVQLRKRRVKNPYPI

SFLLTDLINRRTPRVDGQPMYGMDAQVEEVRVFEGTEELPGDPDMMRYV

DKYGQLQTKML
```

In some embodiments, the disclosure provides a method of reducing JCV titers and/or replication of JCV in a subject in need thereof, the method comprising administering to the subject an effective amount of an anti-JCV antibody or antigen-binding fragment thereof disclosed herein. In some embodiments, the central nervous system of the subject is infected with JCV or is at risk of being infected with JCV.

In one embodiment, the disclosure provides a method of reducing dissemination of JCV to the central nervous system in a subject in need thereof, the method comprising administering to the subject an effective amount of anti-JCV antibody an antibody or antigen-binding fragment thereof disclosed herein.

In one embodiment, the disclosure provides a method of reducing the occurrence, duration, and/or severity of IRIS in a subject in need thereof, the method comprising administering to the subject an effective amount of an anti-JCV antibody or antigen-binding fragment thereof disclosed herein. In some embodiments, the anti-JCV antibody or antigen-binding fragment thereof is administered after the subject has developed IRIS.

In one embodiment, the disclosure provides a method of treating PML in a subject in need thereof, the method comprising administering to the subject an effective amount of an anti-JCV antibody or antigen-binding fragment thereof disclosed herein. In some embodiments, the method further comprises administering one or more additional anti-JCV antibodies or antigen-binding fragments thereof disclosed herein. In some embodiments, the subject has previously received and/or is currently receiving treatment with an anti-retroviral agent. In some embodiments, the subject has previously received and/or is currently receiving treatment with an immunosuppressing agent and/or an immunomodulatory agent. In some embodiments, the immunosuppressing and/or immunomodulatory agent is a modulator of TNF-α, BLys, α4-integrin, CTLA-4, CD11a, CD20, CD30, CD52, sphingosine 1-phosphate receptor, inosine monophosphate dehydrogenase, janus kinase, and/or dihydroorotate dehydrogenase. In some embodiments, the immunosuppressing and/or immunomodulatory agent is Natalizumab, Efalizumab, Belimumab, Rituximab, Fingolimod, Dimethylfumarate, Alemtuzumab, Adalimumab, Etanercept, Ofatumumab, Mycophenolate mofetil, Betalacept, Brentuximab, Fludarabine, Ruxolitinib, Leflunomide, and/or Infliximab. In one embodiment, the central nervous system of the subject is infected with JCV. In one embodiment, the subject has MS and has previously received and/or is currently receiving treatment with a modulator of α4-integrin.

In one embodiment, the disclosure provides a method of treating PML in a subject in need thereof, the method comprising administering to the subject an effective amount of an anti-JCV antibody or antigen-binding fragment thereof disclosed herein, wherein the subject has an immune deficiency. In one embodiment, the immune deficiency is a hereditary immune deficiency, including, but not limited to, adenosine deaminase deficiency, CD40 ligand deficiency, combined immune deficiency, common variable immune deficiency, dedicator of cytokinesis 8 protein (DOCK8) deficiency, gamma heavy chain disease, hyper-IgM syndrome, immunodeficiency-centromeric instability-facial dysmorphism syndrome, purine nucleoside phosphorylase deficiency, severe combined immune deficiency, signal transducer and activator of transcription 1 gain-of-function immune deficiency, Wiskott-Aldrich syndrome, X-linked agammaglobulinaemia, idiopathic CD4+ lymphopenia, and sarcoidosis. In one embodiment, the immune deficiency is an acquired immune deficiency. In one embodiment, the subject is infected with HIV and/or has AIDS.

In one embodiment, the disclosure provides a method of treating PML in a subject in need thereof, the method comprising administering to the subject an effective amount of an anti-JCV antibody or antigen-binding fragment thereof disclosed herein, wherein the subject has cancer, including, but not limited to glioma, glioblastoma, thymoma, mesothelioma, sarcoma, uterine carcinosarcoma, chromphobe renal cell carcinoma, adenoid cystic carcinoma, acute myeloid leukemia, melanoma, uveal melanoma, papillary renal cell carcinoma, clear cell renal cell carcinoma, chloangiocarcinoma, lung adenocarcinoma, diffuse large B-cell lymphoma, pheochromocytoma and paraganglioma, pancreatic cancer, thyroid cancer, lung cancer, colorectal cancer, squamous cancer, breast cancer, prostate cancer, bladder cancer, gastric cancer, testicular germ cell cancer, ovarian cancer, head and neck cancer, uterine cancer, cervical cancer, or liver cancer.

In one embodiment, the disclosure provides a method of treating PML in a subject in need thereof, the method comprising administering to the subject an effective amount of an antibody or antigen-binding fragment thereof disclosed herein, wherein the subject has an autoimmune disease, including, but not limited to, rheumatoid arthritis, psoriatic arthritis, psoriasis, juvenile idiopathic arthritis, inflammatory bowel disease, ankylosing spondylitis, and multiple sclerosis. In a preferred embodiment, the autoimmune disease is multiple sclerosis or Crohn's disease.

In one embodiment, the disclosure provides a method of treating PML in a subject in need thereof, the method comprising administering to the subject an effective amount of an antibody or antigen-binding fragment thereof disclosed herein, wherein the subject has received a transplant, including, but not limited to, a haematopoietic stem cell transplant, a bone marrow transplant, and/or an organ transplant.

In one embodiment, the disclosure provides a method of reducing the likelihood of developing PML in a subject in need thereof, the method comprising administering to the subject an effective amount of an anti-JCV antibody or antigen-binding fragment thereof disclosed herein. In some embodiments, the method further comprises administering one or more additional anti-JCV antibodies or antigen-binding fragments thereof disclosed herein. In one embodiment, the central nervous system of the subject is infected with JCV.

In one embodiment, the disclosure provides a method of reducing the likelihood of developing PML in a subject in need thereof, the method comprising administering to the subject an effective amount of an anti-JCV antibody or antigen-binding fragment thereof disclosed herein, wherein the subject has an immune deficiency. In one embodiment, the immune deficiency is a hereditary immune deficiency, including, but not limited to, adenosine deaminase deficiency, CD40 ligand deficiency, combined immune deficiency, common variable immune deficiency, dedicator of cytokinesis 8 protein (DOCK8) deficiency, gamma heavy chain disease, hyper-IgM syndrome, immunodeficiency-centromeric instability-facial dysmorphism syndrome, purine nucleoside phosphorylase deficiency, severe combined immune deficiency, signal transducer and activator of transcription 1 gain-of-function immune deficiency, Wiskott-Aldrich syndrome, X-linked agammaglobulinaemia, idiopathic CD4+ lymphopenia, and sarcoidosis. In one embodiment, the immune deficiency is an acquired immune deficiency. In one embodiment, the subject is infected with HIV and/or has AIDS.

In one embodiment, the disclosure provides a method of reducing the likelihood of developing PML in a subject in need thereof, the method comprising administering to the subject an effective amount of an anti-JCV antibody or antigen-binding fragment thereof disclosed herein, wherein the subject has cancer, including, but not limited to glioma, glioblastoma, thymoma, mesothelioma, sarcoma, uterine carcinosarcoma, chromphobe renal cell carcinoma, adenoid cystic carcinoma, acute myeloid leukemia, melanoma, uveal melanoma, papillary renal cell carcinoma, clear cell renal cell carcinoma, chloangiocarcinoma, lung adenocarcinoma, diffuse large B-cell lymphoma, pheochromocytoma and paraganglioma, pancreatic cancer, thyroid cancer, lung cancer, colorectal cancer, squamous cancer, breast cancer, prostate cancer, bladder cancer, gastric cancer, testicular germ cell cancer, ovarian cancer, head and neck cancer, uterine cancer, cervical cancer, or liver cancer.

In one embodiment, the disclosure provides a method of reducing the likelihood of developing PML in a subject in need thereof, the method comprising administering to the subject an effective amount of an anti-JCV antibody or antigen-binding fragment thereof disclosed herein, wherein the subject has an autoimmune disease, including, but not limited to, rheumatoid arthritis, psoriatic arthritis, psoriasis, juvenile idiopathic arthritis, inflammatory bowel disease, ankylosing spondylitis, and multiple sclerosis. In a preferred embodiment, the autoimmune disease is multiple sclerosis or Crohn's disease.

In one embodiment, the disclosure provides a method of reducing the likelihood of developing PML in a subject in need thereof, the method comprising administering to the subject an effective amount of an anti-JCV antibody or antigen-binding fragment thereof disclosed herein, wherein the subject has received a transplant, including, but not limited to, a haematopoietic stem cell transplant, a bone marrow transplant, and/or an organ transplant.

In one embodiment, the disclosure provides a method of reducing the likelihood of developing PML in a subject in need thereof, the method comprising administering to the subject an effective amount of an anti-JCV antibody or antigen-binding fragment thereof disclosed herein, wherein the administration of the anti-JCV antibody or antigen-binding fragment occurs before administering an immuno-suppressing agent and/or an immunomodulatory agent to the subject. In some embodiments, the anti-JCV antibody or antigen-binding fragment thereof is further administered during and/or after administration of the immunosuppressing agent and/or immunomodulatory agent. In some embodiments, the immunosuppressing and/or immunomodulatory agent is a modulator of TNF-α, BLys, α4-integrin, CTLA-4, CD11a, CD20, CD30, CD52, sphingosine 1-phosphate receptor, inosine monophosphate dehydrogenase, janus kinase, and/or dihydroorotate dehydrogenase. In some embodiment, the immunosuppressing and/or immunomodulatory agent is Natalizumab, Efalizumab, Belimumab, Rituximab, Fingolimod, Dimethylfumarate, Alemtuzumab, Adalimumab, Etanercept, Ofatumumab, Mycophenolate mofetil, Betalacept, Brentuximab, Fludarabine, Ruxolitinib, Leflunomide, and/or Infliximab. In one embodiment, the subject has multiple sclerosis and has previously received, is currently receiving, and/or will subsequently receive treatment with a modulator of α4-integrin.

In one embodiment, the disclosure provides a method of reducing the likelihood of developing PML in a subject in need thereof, the method comprising administering to the subject an effective amount of an anti-JCV antibody or antigen-binding fragment thereof disclosed herein, wherein the administration of the anti-JCV antibody or antigen-binding fragment occurs before administering an anti-retroviral agent to the subject. In some embodiments, the anti-JCV antibody or antigen-binding fragment thereof is further administered during and/or after administration of the anti-retroviral agent.

In one embodiment, the disclosure provides a method of reducing the likelihood of developing PML in a subject in need thereof, the method comprising administering to the subject an effective amount of an anti-JCV antibody or antigen-binding fragment thereof disclosed herein, wherein the administration of the anti-JCV antibody or antigen-binding fragment occurs before subjecting the subject to a cell or organ transplantation. In some embodiments, the anti-JCV antibody or antigen-binding fragment thereof is further administered during and/or after subjecting the subject to the cell or organ transplantation.

In one embodiment, the disclosure provides a method of treating PML, the method comprising administering to the subject an effective amount of a vector encoding one or more anti-JCV antibodies or antigen-binding fragments thereof disclosed herein.

In one embodiment, the disclosure provides a method of reducing the likelihood of developing PML, the method comprising administering to the subject an effective amount of a vector encoding one or more anti-JCV antibodies or antigen-binding fragments thereof disclosed herein.

BRIEF DESCRIPTION OF THE DRAWINGS

FIG. 1 illustrates the binding of purified anti-JCV antibodies to 293TT cells expressing JCV wild type VP1 (WT VP1), VP1 mutant L55F ("55m VP1"), VP1 mutant S267F ("267m VP1"), or VP1 mutant S269F (269m VP1"), respectively. Binding was determined by flow cytometry. Mean fluorescent intensity is shown on the x-axis (increasing fluorescence from left to right). No antibody binding was observed for the negative control ("mock txf"). Individual antibody clones are indicated (e.g. 2A5, 2A11, etc.). M2=M2E10, control antibody.

FIG. 2 illustrates the dose-dependent neutralization of native (wild type) JCV by selected anti-JCV antibodies. Shown is the ability of wild type JCV to infect 293TT cells in presence of different amounts of selected anti-JCV antibodies (1A7, 1A10, 1F11, 2A11, 3D2, 1E12, 8A7, and 6A4, respectively) as compared the control antibody M2E10. Infectivity was assessed by one-step qRT-PCR for JCV capsid proteins VP1 and VP2.

DETAILED DESCRIPTION

Antibodies

The term "antibody" is used in the broadest sense and includes monoclonal antibodies (including full length or intact monoclonal antibodies), polyclonal antibodies, multivalent antibodies, multispecific antibodies (e.g., bispecific antibodies), antibody fragments, and antigen-binding portions thereof (e.g., paratopes, CDRs), so long as they exhibit the desired biological activity and specificity.

As used herein, "antibody variable domain" refers to the portions of the light and heavy chains of antibody molecules that include amino acid sequences of complementarity determining regions (CDRs; i.e., CDR1, CDR2, and CDR3), and framework regions. $V_H$ refers to the variable domain of the heavy chain. $V_L$ refers to the variable domain of the light chain. The term "framework regions" refers to those variable domain residues other than the CDR residues.

As used herein, the term "complementarity determining regions" refers to portions of an antibody variable domain that are (typically, but not always) involved in antigen binding. Each variable domain typically has three CDR regions identified as CDR1, CDR2 and CDR3. Each CDR can comprise amino acid residues from a CDR as defined by e.g. Kabat (Kabat et al., Sequences of Proteins of Immunological Interest, 5th Ed. Public Health Service, National Institutes of Health, Bethesda, Md. (1987, 1991)). Each CDR can also comprise amino acid residues from a "hypervariable loop" as defined by Chothia (Chothia & Lesk 196 J. Mol. Biol. 901 (1987)). In some instances, a CDR can include amino acids from both a CDR region defined according to Kabat and a hypervariable loop. The Kabat residue designations do not always correspond directly with the linear numbering of the amino acid residues (primary amino acid sequence). The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody or antigen-binding fragment thereof by alignment of residues of homology in the sequence of the antibody or antigen-binding fragment thereof with a "standard" Kabat numbered sequence. Alternatively, a CDR may be defined according to the ImMunoGeneTics (IMGT) system (Lefranc, M.-P. et al., Dev. Comp. Immunol., 27, 55-77 (2003)).

The disclosure provides antibodies and an antigen-binding fragments thereof that bind to JCV.

In one aspect, the anti-JCV antibody or antigen-binding fragment thereof comprises a heavy chain variable region and a light chain variable region;
wherein each of the heavy chain and the light chain variable regions comprises a CDR1, CDR2, and CDR3; and
wherein:
CDR1H comprises the sequence $X_1X_2TFSDX_3Y$ (SEQ ID NO:56);
wherein $X_1$ is G or E;
wherein $X_2$ is F or I;
wherein $X_3$ is H, L, Y, or F;
CDR2H comprises the sequence $ISX_4X_5GX_6X_7I$ (SEQ ID NO:58);
wherein $X_4$ is T or F;
wherein $X_5$ is S or G;
wherein $X_6$ is R or S;
wherein $X_7$ is T or A;
CDR3H comprises the sequence $AX_8DX_9YDNX_{10}GWX_{11}Y$ (SEQ ID NO:61);
wherein $X_8$ is G or S;
wherein $X_9$ is Y or F;
wherein $X_{10}$ is S or V;
wherein $X_{11}$ is D, E, Y, or N;
CDR1L comprises the sequence $QSLX_{25}YSDGNTY$ (SEQ ID NO:65);
wherein $X_{25}$ is V, I or L;
CDR2L comprises the sequence KVS; and
CDR3L comprises the sequence $MQGX_{26}HWPRT$ (SEQ ID NO:67);
wherein $X_{26}$ is T, S or A.

In one aspect, the anti-JCV antibody or antigen-binding fragment thereof comprises a heavy chain variable region and a light chain variable region;
wherein each of the heavy chain and the light chain variable regions comprises a CDR1, CDR2, and CDR3; and
wherein:
CDR1H comprises the sequence $X_1X_2TFSDX_3Y$ (SEQ ID NO:56);
wherein $X_1$ is G or E;
wherein $X_2$ is F or I;
wherein $X_3$ is H, L, Y, or F;
CDR2H comprises the sequence $ISX_4X_5GX_6X_7I$ (SEQ ID NO:58);
wherein $X_4$ is T or F;
wherein $X_5$ is S or G;
wherein $X_6$ is R or S;
wherein $X_7$ is T or A;
CDR3H comprises the sequence $AX_8DX_9YDNX_{10}GWX_{11}Y$ (SEQ ID NO:61);
wherein $X_8$ is G or S;
wherein $X_9$ is Y or F;
wherein $X_{10}$ is S or V;
wherein $X_{11}$ is D, E, Y, or N;
CDR1L comprises the sequence $QSLX_{12}YSDGNTY$ (SEQ ID NO:64);
wherein $X_{12}$ is V or I;
CDR2L comprises the sequence KVS; and
CDR3L comprises the sequence $MQGX_{13}HWPRT$ (SEQ ID NO:66);
wherein $X_{13}$ is T or S.

In one embodiment, the anti-JCV antibody or antigen-binding fragment thereof comprises six CDRs, wherein CDR1H of the antibody or antigen-binding fragment thereof comprises SEQ ID NO:1, CDR2H comprises SEQ ID NO:12, CDR3H comprises SEQ ID NO:23, CDR1L comprises SEQ ID NO:36, CDR2L comprises the sequence KVS, and CDR3L comprises SEQ ID NO:45.

In one embodiment, the anti-JCV antibody or antigen-binding fragment thereof comprises six CDRs, wherein CDR1H of the antibody or antigen-binding fragment thereof comprises SEQ ID NO:2, CDR2H comprises SEQ ID NO:12, CDR3H comprises SEQ ID NO:24, CDR1L comprises SEQ ID NO:36, CDR2L comprises the sequence KVS, and CDR3L comprises SEQ ID NO:45.

In one embodiment, the anti-JCV antibody or antigen-binding fragment thereof comprises six CDRs, wherein CDR1H of the antibody or antigen-binding fragment thereof comprises SEQ ID NO:3, CDR2H comprises SEQ ID NO:12, CDR3H comprises SEQ ID NO:25, CDR1L comprises SEQ ID NO:36, CDR2L comprises the sequence KVS, and CDR3L comprises SEQ ID NO:45.

In one embodiment, the anti-JCV antibody or antigen-binding fragment thereof comprises six CDRs, wherein CDR1H of the antibody or antigen-binding fragment thereof comprises SEQ ID NO:3, CDR2H comprises SEQ ID NO:12, CDR3H comprises SEQ ID NO:26, CDR1L comprises SEQ ID NO:36, CDR2L comprises the sequence KVS, and CDR3L comprises SEQ ID NO:45.

In one embodiment, the anti-JCV antibody or antigen-binding fragment thereof comprises six CDRs, wherein CDR1H of the antibody or antigen-binding fragment thereof comprises SEQ ID NO:3, CDR2H comprises SEQ ID NO:13, CDR3H comprises SEQ ID NO:27, CDR1L comprises SEQ ID NO:36, CDR2L comprises the sequence KVS, and CDR3L comprises SEQ ID NO:46.

In one embodiment, the anti-JCV antibody or antigen-binding fragment thereof comprises six CDRs, wherein CDR1H of the antibody or antigen-binding fragment thereof comprises SEQ ID NO:3, CDR2H comprises SEQ ID NO:14, CDR3H comprises SEQ ID NO:28, CDR1L comprises SEQ ID NO:37, CDR2L comprises the sequence KVS, and CDR3L comprises SEQ ID NO:45.

In one embodiment, the anti-JCV antibody or antigen-binding fragment thereof comprises six CDRs, wherein CDR1H of the antibody or antigen-binding fragment thereof comprises SEQ ID NO:3, CDR2H comprises SEQ ID NO:12, CDR3H comprises SEQ ID NO:26, CDR1L comprises SEQ ID NO:36, CDR2L comprises the sequence KVS, and CDR3L comprises SEQ ID NO:45.

In one embodiment, the anti-JCV antibody or antigen-binding fragment thereof comprises six CDRs, wherein CDR1H of the antibody or antigen-binding fragment thereof comprises SEQ ID NO:4, CDR2H comprises SEQ ID NO:15, CDR3H comprises SEQ ID NO:28, CDR1L comprises SEQ ID NO:36, CDR2L comprises the sequence KVS, and CDR3L comprises SEQ ID NO:45.

In one embodiment, the anti-JCV antibody or antigen-binding fragment thereof comprises six CDRs, wherein CDR1H of the antibody or antigen-binding fragment thereof comprises SEQ ID NO:3, CDR2H comprises SEQ ID NO:12, CDR3H comprises SEQ ID NO:28, CDR1L comprises SEQ ID NO:38, CDR2L comprises the sequence KVS, and CDR3L comprises SEQ ID NO:47.

In one embodiment, the anti-JCV antibody or antigen-binding fragment thereof comprises six CDRs, wherein CDR1H of the antibody or antigen-binding fragment thereof comprises SEQ ID NO:5, CDR2H comprises SEQ ID NO:12, CDR3H comprises SEQ ID NO:23, CDR1L comprises SEQ ID NO:36, CDR2L comprises the sequence KVS, and CDR3L comprises SEQ ID NO:45.

In one aspect, the anti-JCV antibody or antigen-binding fragment thereof comprises a heavy chain variable region and a light chain variable region;
wherein each of the heavy chain and the light chain variable regions comprises a CDR1, CDR2, and CDR3; and
wherein:
CDR1H comprises SEQ ID NO:6;
CDR2H comprises SEQ ID NO:16;
CDR3H comprises the sequence ARRGFEQQLSYYYYYGX$_{14}$DV (SEQ ID NO:62);
wherein X$_{14}$ is L or M;
CDR1L comprises SEQ ID NO:39;
CDR2L comprises the sequence WAS;
CDR3L comprises the sequence QQYYX$_{15}$X$_{16}$PWT (SEQ ID NO:68);
wherein X$_{15}$ is T or S; and
wherein X$_{16}$ is T or F.

In one embodiment, the anti-JCV antibody or antigen-binding fragment thereof comprises six CDRs, wherein CDR1H of the antibody or antigen-binding fragment thereof comprises SEQ ID NO:6, CDR2H comprises SEQ ID NO:16, CDR3H comprises SEQ ID NO:29, CDR1L comprises SEQ ID NO:39, CDR2L comprises the sequence WAS and CDR3L comprises SEQ ID NO:48.

In one embodiment, the anti-JCV antibody or antigen-binding fragment thereof comprises six CDRs, wherein CDR1H of the antibody or antigen-binding fragment thereof comprises SEQ ID NO:6, CDR2H comprises SEQ ID NO:16, CDR3H comprises SEQ ID NO:30, CDR1L comprises SEQ ID NO:39, CDR2L comprises the sequence WAS, and CDR3L comprises SEQ ID NO:49.

In one aspect, the anti-JCV antibody or antigen-binding fragment thereof comprises a heavy chain variable region and a light chain variable region;
wherein each of the heavy chain and the light chain variable regions comprises a CDR1, CDR2, and CDR3; and
wherein:
CDR1H comprises the sequence GYTFTX$_{17}$YD (SEQ ID NO:57);
wherein X$_{17}$ is F or N;
CDR2H comprises the sequence X$_{23}$NPNSGNX$_{24}$ (SEQ ID NO:60);
wherein X$_{23}$ is M, V, or T;
wherein X$_{24}$ is T or S;
CDR3H comprises the sequence ARKIWVGX$_{20}$TX$_{21}$FDX$_{22}$ (SEQ ID NO:63);
wherein X$_{20}$ is H or T;
wherein X$_{21}$ is T or I;
wherein X$_{22}$ is R or Y;
CDR1L comprises SEQ ID NO:40 or SEQ ID NO:41;
CDR2L comprises the sequence AAS or sequence AVS;
CDR3L comprises SEQ ID NO:50, SEQ ID NO:51, or SEQ ID NO:52. In one aspect, the anti-JCV antibody or antigen-binding fragment thereof comprises a heavy chain variable region and a light chain variable region;
wherein each of the heavy chain and the light chain variable regions comprises a CDR1, CDR2, and CDR3; and
wherein:
CDR1H comprises the sequence GYTFTX$_{17}$YD (SEQ ID NO:57);
wherein X$_{17}$ is F or N;
CDR2H comprises the sequence X$_{18}$NPNSGNX$_{19}$ (SEQ ID NO:59);
wherein X$_{18}$ is M or V;
wherein X$_{19}$ is T or S;
CDR3H comprises the sequence ARKIWVGX$_{20}$TX$_{21}$FDX$_{22}$ (SEQ ID NO:63);
wherein X$_{20}$ is H or T;
wherein X$_{21}$ is T or I;
wherein X$_{22}$ is R or Y;
CDR1L comprises SEQ ID NO:40 or SEQ ID NO:41;
CDR2L comprises the sequence AAS or sequence AVS;
CDR3L comprises SEQ ID NO:50 or SEQ ID NO:51.

In one embodiment, the anti-JCV antibody or antigen-binding fragment thereof comprises six CDRs, wherein CDR1H of the antibody or antigen-binding fragment thereof comprises SEQ ID NO:7, CDR2H comprises SEQ ID NO:17, CDR3H comprises SEQ ID NO:31, CDR1L comprises SEQ ID NO:40, CDR2L comprises the sequence AAS, and CDR3L comprises SEQ ID NO:50.

In one embodiment, the anti-JCV antibody or antigen-binding fragment thereof comprises six CDRs, wherein CDR1H of the antibody or antigen-binding fragment thereof comprises SEQ ID NO:8, CDR2H comprises SEQ ID NO:18, CDR3H comprises SEQ ID NO:32, CDR1L comprises SEQ ID NO:41, CDR2L comprises the sequence AAS, and CDR3L comprises SEQ ID NO:51.

In one embodiment, the anti-JCV antibody or antigen-binding fragment thereof comprises six CDRs, wherein CDR1H of the antibody or antigen-binding fragment thereof comprises SEQ ID NO:8, CDR2H comprises SEQ ID NO:19, CDR3H comprises SEQ ID NO:32, CDR1L comprises SEQ ID NO:41, CDR2L comprises the sequence AVS, and CDR3L comprises SEQ ID NO:52.

In one aspect, the anti-JCV antibody or antigen-binding fragment thereof comprises a heavy chain variable region and a light chain variable region;
wherein each of the heavy chain and the light chain variable regions comprises a CDR1, CDR2, and CDR3; and
wherein:
CDR1H comprises SEQ ID NO:9, SEQ ID NO:10, or SEQ ID NO:11;
CDR2H comprises SEQ ID NO:20, SEQ ID NO:21, or SEQ ID NO:22;
CDR3H comprises SEQ ID NO:33, SEQ ID NO:34, or SEQ ID NO:35;
CDR1L comprises SEQ ID NO:42, SEQ ID NO:43, or SEQ ID NO:44;
CDR2L comprises the sequence WAS, sequence GAS, or sequence GTS; and
CDR3L comprises SEQ ID NO:53, SEQ ID NO:54, or SEQ ID NO:55.

In one embodiment, the anti-JCV antibody or antigen-binding fragment thereof comprises six CDRs, wherein CDR1H of the antibody or antigen-binding fragment thereof comprises SEQ ID NO:9, CDR2H comprises SEQ ID NO:20, CDR3H comprises SEQ ID NO:33, CDR1L comprises SEQ ID NO:42, CDR2L comprises the sequence WAS, and CDR3L comprises SEQ ID NO:53.

In one embodiment, the anti-JCV antibody or antigen-binding fragment thereof comprises six CDRs, wherein CDR1H of the antibody or antigen-binding fragment thereof comprises SEQ ID NO:10, CDR2H comprises SEQ ID NO:21, CDR3H comprises SEQ ID NO:34, CDR1L comprises SEQ ID NO:43, CDR2L comprises the sequence GAS, and CDR3L comprises SEQ ID NO:54.

In one embodiment, the anti-JCV antibody or antigen-binding fragment thereof comprises six CDRs, wherein CDR1H of the antibody or antigen-binding fragment thereof comprises SEQ ID NO:11, CDR2H comprises SEQ ID NO:22, CDR3H comprises SEQ ID NO:35, CDR1L comprises SEQ ID NO:44, CDR2L comprises the sequence GTS, and CDR3L comprises SEQ ID NO:55.

In certain embodiments, the CDRs of an anti-JCV antibody or antigen-binding fragment thereof disclosed herein are located in frameworks obtained from a human antibody or antigen-binding fragment thereof. In some embodiments, surface-exposed framework residues of an anti-JCV antibody or antigen-binding fragment thereof disclosed herein are replaced with framework residues of a human antibody or antigen-binding fragment thereof. The CDRs may also be located in murine or humanized frameworks linked to human constant regions (i.e., chimeric antibodies). In one embodiment, the CDRs of an anti-JCV or antigen-binding fragment thereof are located in frameworks that are a composite of two or more human antibodies. In one embodiment, the anti-JCV or antigen-binding fragment thereof is a CDR-grafted antibody.

Also provided herein are variable heavy and light chain variable region sequences as well as any pairings thereof that are similar, but not identical to the variable heavy chain and variable light chains disclosed in SEQ ID NOs:69-104 and any pairings thereof. As used herein, the term "identity" refers to sequence identity between two nucleic acid molecules or polypeptides. Identity can be determined by comparing a position in each sequence, which may be aligned for purposes of comparison. For example, when a position in the compared nucleotide sequence is occupied by the same base, then the molecules are identical at that position. A degree identity between nucleic acid or amino acid sequences is a function of the number of identical or matching nucleotides or amino acids at shared positions. For example, polypeptides having at least 85%, at least 90%, at least 95%, at least 96%, at least 97%, at least 98%, or at least 99% identity to specific polypeptides described herein and preferably exhibiting substantially the same functions, as well as polynucleotides encoding such polypeptides, are contemplated. Methods and computer programs for determining both sequence identity and similarity are publicly available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at http://www.ncbi.nlm.nih.gov/blast/). In comparing sequences, these methods account for various substitutions, deletions, and other modifications.

In one aspect, the disclosure provides an anti-JCV antibody or antigen-binding fragment thereof that comprises a heavy chain variable region that is at least 80%, at least 85%, at least 90%, at least 95%, at least 96%, at least 97%, at least 98%, or at least 99% identical to a sequence selected from SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, or SEQ ID NO:103.

In one aspect, the disclosure provides an anti-JCV or antigen-binding fragment thereof that comprises a light chain variable region that is at least 80%, at least 85%, at least 90%, at least 95%, at least 96%, at least 97%, at least 98%, or at least 99% identical to a sequence selected from SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO: 94, SEQ ID NO:96, or SEQ ID NO:98; SEQ ID NO:100, SEQ ID NO:102, or SEQ ID NO:104.

In one embodiment, the anti-JCV antibody or antigen-binding fragment thereof comprises:
(a) a heavy chain variable region that is at least 80%, at least 85%, at least 90%, at least 95%, at least 96%, at least 97%, at least 98%, or at least 99% identical to a sequence selected from SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, or SEQ ID NO:103; and
(b) a light chain variable region that is at least 80%, at least 85%, at least 90%, at least 95%, at least 96%, at least 97%, at least 98%, or at least 99% identical to a sequence selected from SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, or SEQ ID NO:98; SEQ ID NO:100, SEQ ID NO:102, or SEQ ID NO:104.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:69, and a light chain variable region that is at least at least 80%, at least 85%, at least 90%, at least 95%, at least 96%, at least 97%, at least 98%, or at least 99% identical to SEQ ID NO:70.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:71, and a light chain variable region that is at least at least 80%, at least 85%, at least 90%, at least 95%, at least 96%, at least 97%, at least 98%, or at least 99% identical to SEQ ID NO:72.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:73, and a light chain variable region that is at least at least 80%, at least 85%, at least 90%, at least 95%, at least 96%, at least 97%, at least 98%, or at least 99% identical to SEQ ID NO:74.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:75, and a light chain variable region that is at least at least 80%, at least 85%, at least 90%, at least 95%, at least 96%, at least 97%, at least 98%, or at least 99% identical to SEQ ID NO:76.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:77, and a light chain variable region that is at least at least 80%, at least 85%, at least 90%, at least 95%, at least 96%, at least 97%, at least 98%, or at least 99% identical to SEQ ID NO:78.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:79, and a light chain variable region that is at least at least 80%, at least 85%, at least 90%, at least 95%, at least 96%, at least 97%, at least 98%, or at least 99% identical to SEQ ID NO:80.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:81, and a light chain variable region that is at least at least 80%, at least 85%, at least 90%, at least 95%, at least 96%, at least 97%, at least 98%, or at least 99% identical to SEQ ID NO:82.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:83, and a light chain variable region that is at least at least 80%, at least 85%, at least 90%, at least 95%, at least 96%, at least 97%, at least 98%, or at least 99% identical to SEQ ID NO:84.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:85, and a light chain variable region that is at least at least 80%, at least 85%, at least 90%, at least 95%, at least 96%, at least 97%, at least 98%, or at least 99% identical to SEQ ID NO:86.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:87, and a light chain variable region that is at least at least 80%, at least 85%, at least 90%, at least 95%, at least 96%, at least 97%, at least 98%, or at least 99% identical to SEQ ID NO:88.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:89, and a light chain variable region that is at least at least 80%, at least 85%, at least 90%, at least 95%, at least 96%, at least 97%, at least 98%, or at least 99% identical to SEQ ID NO:90.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:91, and a light chain variable region that is at least at least 80%, at least 85%, at least 90%, at least 95%, at least 96%, at least 97%, at least 98%, or at least 99% identical to SEQ ID NO92.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:93, and a light chain variable region that is at least at least 80%, at least 85%, at least 90%, at least 95%, at least 96%, at least 97%, at least 98%, or at least 99% identical to SEQ ID NO:94.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:95, and a light chain variable region that is at least at least 80%, at least 85%, at least 90%, at least 95%, at least 96%, at least 97%, at least 98%, or at least 99% identical to SEQ ID NO:96.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:97, and a light chain variable region that is at least at least 80%, at least 85%, at least 90%, at least 95%, at least 96%, at least 97%, at least 98%, or at least 99% identical to SEQ ID NO:98.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:99, and a light chain variable region that is at least at least 80%, at least 85%, at least 90%, at least 95%, at least 96%, at least 97%, at least 98%, or at least 99% identical to SEQ ID NO:100.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:101, and a light chain variable region that is at least at least 80%, at least 85%, at least 90%, at least 95%, at least 96%, at least 97%, at least 98%, or at least 99% identical to SEQ ID NO:102.

In one embodiment, the anti-JCV antibody or antigen-binding fragment thereof further comprises a heavy chain variable region that is at least at least 80%, at least 85%, at least 90%, at least 95%, at least 96%, at least 97%, at least 98%, or at least 99% identical to SEQ ID NO:103, and a light chain variable region that is at least at least 80%, at least 85%, at least 90%, at least 95%, at least 96%, at least 97%, at least 98%, or at least 99% identical to SEQ ID NO:104.

In one embodiment, the disclosure provides an antibody or antigen-binding fragment thereof which binds to JCV, wherein the heavy chain variable region of the antibody or antigen-binding fragment thereof comprises SEQ ID NO:69 and the light chain variable region comprises SEQ ID NO:70.

In one embodiment, the disclosure provides an antibody or antigen-binding fragment thereof which binds to JCV, wherein the heavy chain variable region of the antibody or antigen-binding fragment thereof comprises SEQ ID NO:71 and the light chain variable region comprises SEQ ID NO:72.

In one embodiment, the disclosure provides an antibody or antigen-binding fragment thereof which binds to JCV, wherein the heavy chain variable region of the antibody or antigen-binding fragment thereof comprises SEQ ID NO:73 and the light chain variable region comprises SEQ ID NO:74.

In one embodiment, the disclosure provides an antibody or antigen-binding fragment thereof which binds to JCV, wherein the heavy chain variable region of the antibody or antigen-binding fragment thereof comprises SEQ ID NO:75 and the light chain variable region comprises SEQ ID NO:76.

In one embodiment, the disclosure provides an antibody or antigen-binding fragment thereof which binds to JCV, wherein the heavy chain variable region of the antibody or antigen-binding fragment thereof comprises SEQ ID NO:77 and the light chain variable region comprises SEQ ID NO:78.

In one embodiment, the disclosure provides an antibody or antigen-binding fragment thereof which binds to JCV, wherein the heavy chain variable region of the antibody or antigen-binding fragment thereof comprises SEQ ID NO:79 and the light chain variable region comprises SEQ ID NO:80.

In one embodiment, the disclosure provides an antibody or antigen-binding fragment thereof which binds to JCV, wherein the heavy chain variable region of the antibody or antigen-binding fragment thereof comprises SEQ ID NO:81 and the light chain variable region comprises SEQ ID NO:82.

In one embodiment, the disclosure provides an antibody or antigen-binding fragment thereof which binds to JCV, wherein the heavy chain variable region of the antibody or antigen-binding fragment thereof comprises SEQ ID NO:83 and the light chain variable region comprises SEQ ID NO:84.

In one embodiment, the disclosure provides an antibody or antigen-binding fragment thereof which binds to JCV, wherein the heavy chain variable region of the antibody or antigen-binding fragment thereof comprises SEQ ID NO:85 and the light chain variable region comprises SEQ ID NO:86.

In one embodiment, the disclosure provides an antibody or antigen-binding fragment thereof which binds to JCV, wherein the heavy chain variable region of the antibody or antigen-binding fragment thereof comprises SEQ ID NO:87 and the light chain variable region comprises SEQ ID NO:88.

In one embodiment, the disclosure provides an antibody or antigen-binding fragment thereof which binds to JCV, wherein the heavy chain variable region of the antibody or antigen-binding fragment thereof comprises SEQ ID NO:89 and the light chain variable region comprises SEQ ID NO:90.

In one embodiment, the disclosure provides an antibody or antigen-binding fragment thereof which binds to JCV, wherein the heavy chain variable region of the antibody or antigen-binding fragment thereof comprises SEQ ID NO:91 and the light chain variable region comprises SEQ ID NO:92.

In one embodiment, the disclosure provides an antibody or antigen-binding fragment thereof which binds to JCV, wherein the heavy chain variable region of the antibody or antigen-binding fragment thereof comprises SEQ ID NO:93 and the light chain variable region comprises SEQ ID NO:94.

In one embodiment, the disclosure provides an antibody or antigen-binding fragment thereof which binds to JCV, wherein the heavy chain variable region of the antibody or antigen-binding fragment thereof comprises SEQ ID NO:95 and the light chain variable region comprises SEQ ID NO:96.

In one embodiment, the disclosure provides an antibody or antigen-binding fragment thereof which binds to JCV, wherein the heavy chain variable region of the antibody or antigen-binding fragment thereof comprises SEQ ID NO:97 and the light chain variable region comprises SEQ ID NO:98.

In one embodiment, the disclosure provides an antibody or antigen-binding fragment thereof which binds to JCV, wherein the heavy chain variable region of the antibody or antigen-binding fragment thereof comprises SEQ ID NO:99 and the light chain variable region comprises SEQ ID NO:100.

In one embodiment, the disclosure provides an antibody or antigen-binding fragment thereof which binds to JCV, wherein the heavy chain variable region of the antibody or antigen-binding fragment thereof comprises SEQ ID NO:101 and the light chain variable region comprises SEQ ID NO:102.

In one embodiment, the disclosure provides an antibody or antigen-binding fragment thereof which binds to JCV, wherein the heavy chain variable region of the antibody or antigen-binding fragment thereof comprises SEQ ID NO:103 and the light chain variable region comprises SEQ ID NO:104.

It will be evident that any of the frameworks described herein can be utilized in combination with any of the CDRs and CDR motifs described herein.

The disclosure also provides anti-JCV antibodies or antigen-binding fragments thereof that contain one or more amino acid sequence modification as compared to other anti-JCV antibodies or antigen-binding fragments thereof disclosed herein. Amino acid sequence variants of the anti-JCV antibody or antigen-binding fragment thereof may be prepared by introducing appropriate nucleotide changes into the nucleic acid encoding the anti-JCV antibody or antigen-binding fragment thereof, or by peptide synthesis. Such modifications include, for example, deletions from, insertions into, and/or substitutions of residues within the amino acid sequences of an anti-JCV antibody or antigen-binding fragment thereof disclosed herein. Combinations of deletions, insertions, and/or substitutions may be made, provided that the final construct possesses the desired characteristics, e.g., binding specificity, inhibition of biological activity.

One type of a variant of an anti-JCV antibody or antigen-binding fragment thereof contemplated by this disclosure is a conservative amino acid substitution variant. These variants have at least one amino acid residue in the anti-JCV antibody or antigen-binding fragment thereof replaced by a different residue that has similar side chain properties. Amino acids can be grouped according to similarities in the properties of their side chains (see Lehninger, BIOCHEMISTRY (2nd ed., Worth Publishers, New York, 1975):

(1) non-polar: Ala (A), Val (V), Leu (L), Ile (I), Pro (P), Phe (F), Trp (W), Met (M);

(2) uncharged polar: Gly (G), Ser (S), Thr (T), Cys (C), Tyr (Y), Asn (N), Gln (Q);

(3) acidic: Asp (D), Glu (E);

(4) basic: Lys (K), Arg (R), His (H).

As such, a non-limiting example for a conservative amino acid substitution is one that replaces a non-polar amino acid with another non-polar amino acid.

Alternatively, naturally occurring residues can be divided into groups based on common side-chain properties:
(1) hydrophobic: Ala (A), Val (V), Leu (L), Ile (I), Met (M);
(2) neutral hydrophilic: Ser (S), Thr (T), Cys (C), Asn (N), Gln (Q);
(3) acidic: Asp (D), Glu (E);
(4) basic: Lys (K), Arg (R), His (H);
(5) residues that influence chain orientation: Gly (G), Pro (P);
(6) aromatic: Phe (F), Trp (W), Tyr (Y).
As such, a non-limiting example for a conservative amino acid substitution is one that replaces a hydrophobic amino acid with another hydrophobic amino acid.

The disclosure also provides non-conservative amino acid substitutions in the anti-JCV antibodies or antigen-binding fragments thereof disclosed herein, provided that the mutated anti-JCV antibody or antigen-binding fragment thereof possesses the desired characteristics, e.g., binding specificity, inhibition of biological activity.

Further contemplated are amino acid sequence insertions, which can include amino- and/or carboxyl-terminal fusions ranging in length from one residue to polypeptides containing a hundred or more residues, as well as intrasequence insertions of single or multiple amino acid residues. Examples of terminal insertions include an anti-JCV antibody or antigen-binding fragment thereof with an N-terminal methionyl residue or the antibody or antigen-binding fragment thereof fused to a cytotoxic polypeptide. Other insertional variants of the anti-JCV antibody or antigen-binding fragment thereof include the fusion to the N- or C-terminus of the antibody or antigen-binding fragment thereof to an enzyme or a polypeptide which increases the serum half-life of the antibody or antigen-binding fragment thereof, such as, for example, biotin.

Any cysteine residue not involved in maintaining the proper conformation of the anti-JCV antibodies or antigen-binding fragments thereof also can be substituted, for example with a serine or an alanine, to improve the oxidative stability of the molecule and prevent aberrant crosslinking. Conversely, cysteine bond(s) can be added to the anti-JCV antibody or antigen-binding fragment thereof to improve its stability (particularly where the antibody or antigen-binding fragment thereof is an antibody fragment such as an Fv fragment).

In some embodiments, the anti-JCV antibodies or antigen-binding fragments thereof described herein have amino acid alterations that alter the original glycosylation pattern of the antibody or antigen-binding fragment thereof. By "altering the original glycosylation pattern" is meant deleting one or more carbohydrate moieties found in the antibody or antigen-binding fragment thereof, and/or adding one or more glycosylation sites that are not present in the antibody or antigen-binding fragment thereof. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, wherein X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used. Addition of glycosylation sites to the anti-JCV antibodies or antigen-binding fragments thereof is accomplished by altering the amino acid sequence such that it contains one or more of the above-described tripeptide sequences (for N-linked glycosylation sites). The alteration can also be made by the addition of, or substitution by, one or more serine or threonine residues to the sequence of the original anti-JCV antibody or antigen-binding fragment thereof (for O-linked glycosylation sites).

In some embodiments, the anti-JCV antibodies or antigen-binding fragments thereof provided herein are deglycosylated or aglycosylated. In some embodiments, the contemplated anti-JCV antibody or antigen-binding fragment thereof lacks a C-terminal lysine in the heavy chain and/or contains a S241P substitution in the constant region of the heavy chain. Where the antibody or antigen-binding fragment thereof comprises an Fc region, the carbohydrate(s) attached thereto can be altered. For example, antibodies with a mature carbohydrate structure that lacks fucose attached to an Fc region of the antibody or antigen-binding fragment thereof are described. See, e.g., U.S. Patent Pubs. No. 2003/0157108; No. 2004/0093621. Antibodies with a bisecting N-acetylglucosamine (GlcNAc) in the carbohydrate attached to an Fc region of the antibody or antigen-binding fragment thereof are referenced in WO 03/011878; U.S. Pat. No. 6,602,684. Antibodies with at least one galactose residue in the oligosaccharide attached to an Fc region of the antibody or antigen-binding fragment thereof are reported in WO 97/30087. See also WO 98/58964; WO 99/22764 concerning antibodies with altered carbohydrate attached to the Fc region thereof.

Antibodies with improved binding to the neonatal Fc receptor (FcRn), and increased half-lives, are described in WO 00/42072 and U.S. Patent Pub. No. 2005/0014934. These antibodies comprise an Fc region with one or more substitutions therein which improve binding of the Fc region to FcRn. For example, the Fc region can have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues).

Antibody Fragments and Types

The disclosure further provides fragments of the anti-JCV antibodies disclosed herein as well as different antibody types of the anti-JCV antibodies disclosed herein.

For instance, the disclosure provides a Fab fragment, which comprises or consists essentially a variable ($V_L$) and constant ($C_L$) domain of the light chain and a variable domain ($V_H$) and the first constant domain ($C_H1$) of the heavy chain.

The disclosure further provides a Fab' fragment, which refers to a Fab fragment having one or more cysteine residues at the C-terminus of the $C_H1$ domain.

The disclosure also provides an Fd fragment comprising or consisting essentially of $V_H$ and $C_H1$ domains.

The disclosure also provides an Fd' fragment comprising $V_H$ and $C_H1$ domains and one or more cysteine residues at the C-terminus of the $C_H1$ domain.

Single-chain Fv or scFv antibody fragments comprise or consist essentially of the $V_H$ and $V_L$ domains of antibody, such that these domains are present in a single polypeptide chain. Generally, an Fv polypeptide further comprises a polypeptide linker between the $V_H$ and $V_L$ domains, which allows the scFv to form the desired structure for antigen binding. See, for example, Pluckthun, 113 Pharmacology Monoclonal Antibodies 269 (Rosenburg & Moore, eds., Springer-Verlag, New York, 1994). Accordingly, the disclosure also provides a scFv fragment comprising or consisting essentially of the $V_L$ and $V_H$ domains of a single arm of an antibody.

In one embodiment, the disclosure provides a diabody comprising two antigen binding sites, comprising a heavy chain variable domain ($V_H$) connected to a light chain variable domain ($V_L$) in the same polypeptide chain.

In one embodiment, the disclosure provides a dAb fragment comprising or consisting essentially of a $V_H$ domain.

In one embodiment, the disclosure provides a F(ab')2 fragment, which comprises a bivalent fragment comprising two Fab' fragments linked by a disulfide bridge at the hinge region.

Linear antibodies refers to the antibodies as described in Zapata et al., Protein Engin., 8(10):1057-1062 (1995). Briefly, these antibodies comprise a pair of tandem Fd segments ($V_H$-$C_H$1-$V_H$-$C_H$1), which, together with complementary light chain polypeptides, form a pair of antigen binding regions. Linear antibodies can be bispecific or monospecific. Accordingly, the disclosure also provides a linear antibody comprising a pair of tandem Fd segments ($V_H$-$C_H$1-$V_H$-$C_H$1) which, together with complementary light chain polypeptides, form a pair of antigen binding regions.

Various techniques have been developed and are available for the production of antibody fragments. Traditionally, these fragments were derived via proteolytic digestion of intact antibodies. See, e.g., Morimoto et al., 24 J. Biochem. Biophys. Meths. 107 (1992); Brennan et al., 229 Science 81 (1985). However, these fragments can now be produced directly by recombinant host cells. For example, antibody fragments can be isolated from the antibody phage libraries discussed herein. Alternatively, Fab'-SH fragments can be directly recovered from E. coli and chemically coupled to form F(ab')2 fragments (Carter et al., 1992). According to another approach, F(ab')2 fragments can be isolated directly from recombinant host cell culture. Other techniques for the production of antibody fragments will be apparent to the skilled practitioner.

The anti-JCV antibodies or antigen-binding fragments disclosed herein may have all types of constant regions, including IgM, IgG, IgD, and IgE, and any isotype, including IgG1, IgG2, IgG3, and IgG4. In one embodiment, the human isotype IgG1 is used. In another embodiment, the human isotype IgG2a, IgG 2b, or IgG 2c is used. The light chain constant regions can be X or K. The anti-JCV antibody or antigen-binding fragment thereof may comprise sequences from more than one class or isotype.

Antibody Conjugates

In some embodiments of the aspects described herein, the anti-JCV antibody or antigen-binding fragment thereof is conjugated to a functional moiety. Examples of useful functional moieties include, but are not limited to, a blocking moiety, a detectable moiety, a diagnostic moiety, a targeting moiety, and a therapeutic moiety.

Exemplary blocking moieties include moieties of sufficient steric bulk and/or charge such that reduced glycosylation occurs, for example, by blocking the ability of a glycosidase to glycosylate the antibody or antigen-binding fragment thereof. The blocking moiety may, additionally or alternatively, reduce effector function, for example, by inhibiting the ability of the Fc region to bind a receptor or complement protein. Preferred blocking moieties include cysteine adducts and PEG moieties.

In one embodiment, the blocking moiety is a cysteine, preferably a cysteine that has associated with a free cysteine, e.g., during or subsequent to the translation of the Fc containing polypeptide, e.g., in cell culture. Other blocking cysteine adducts include cystine, mixed disulfide adducts, or disulfide linkages.

In another embodiment, the blocking moiety is a polyalkylene glycol moiety, for example, a PEG moiety and preferably a PEG-maleimide moiety. Preferred pegylation moieties (or related polymers) can be, for example, polyethylene glycol ("PEG"), polypropylene glycol ("PPG"), polyoxyethylated glycerol ("POG") and other polyoxyethylated polyols, polyvinyl alcohol ("PVA") and other polyalkylene oxides, polyoxyethylated sorbitol, or polyoxyethylated glucose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 Daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic. Pegylation can improve pharmacokinetic performance of a molecule by increasing the molecule's apparent molecular weight. The increased apparent molecular weight reduces the rate of clearance from the body following subcutaneous or systemic administration. In many cases, pegylation can decrease antigenicity and immunogenicity. In addition, pegylation can increase the solubility of a biologically-active molecule.

Examples of detectable moieties for the detection of the anti-JCV antibodies and antigen-binding fragments thereof contemplated by the disclosure include fluorescent moieties or labels, imaging agents, radioisotopic moieties, radiopaque moieties, and the like, e.g. detectable labels such as biotin, fluorophores, chromophores, spin resonance probes, or radiolabels. Exemplary fluorophores include fluorescent dyes (e.g. fluorescein, rhodamine, and the like) and other luminescent molecules (e.g. luminol). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei ($^{13}$C, $^{15}$N, $^{2}$H, $^{125}$I, $^{123}$I, $^{99}$Tc, $^{43}$K, $^{52}$Fe, $^{67}$Ga, $^{68}$Ga, $^{111}$In and the like). Other useful moieties are known in the art.

Examples of diagnostic moieties include detectable moieties suitable for revealing the presence of a disease or disorder. Typically a diagnostic moiety allows for determining the presence, absence, or level of a molecule, for example, a target peptide, protein, or proteins, that is associated with a disease or disorder. Such diagnostics are also suitable for prognosing and/or diagnosing a disease or disorder and its progression.

Examples of therapeutic moieties include, for example, anti-inflammatory agents, anti-cancer agents, anti-neurodegenerative agents, anti-infective agents, or generally a therapeutic. The functional moiety may also have one or more of the above-mentioned functions.

Exemplary therapeutic moieties include radionuclides with high-energy ionizing radiation that are capable of causing multiple strand breaks in nuclear DNA, and therefore suitable for inducing cell death (e.g., of a cancer). Exemplary high-energy radionuclides include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re.

Exemplary therapeutic moieties also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogenesis agents, and the like.

Techniques for conjugating such therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

To increase the half-life of the antibodies or polypeptides containing the amino acid sequences described herein, one can attach a salvage receptor binding epitope to the anti-JCV antibody or antigen-binding fragment thereof (especially an antibody fragment), as described, e.g., in U.S. Pat. No. 5,739,277. The term "salvage receptor binding epitope" may refer to an epitope of the Fc region of an IgG molecule (e.g., IgG1, IgG2, IgG3, or IgG4) that is responsible for increasing the in vivo serum half-life of the IgG molecule (e.g., Ghetie et al., 18 Ann. Rev. Immunol. 739 (2000). Antibodies with substitutions in an Fc region thereof and increased serum half-lives are also described in WO 00/42072, WO 02/060919; Shields et al., 276 J. Biol. Chem. 6591 (2001); Hinton, 279 J. Biol. Chem. 6213-6216 (2004). For example, a nucleic acid molecule encoding the salvage receptor binding epitope can be linked in frame to a nucleic acid encoding a polypeptide sequence described herein so that the fusion protein expressed by the engineered nucleic acid molecule comprises the salvage receptor binding epitope and a polypeptide sequence described herein. In another embodiment, the serum half-life can also be increased, for example, by attaching other polypeptide sequences.

Other types of functional moieties are known in the art and can be readily used in the methods and compositions of the present disclosure based on the teachings contained herein.

Nucleic Acids

Also provided herein are nucleic acids encoding anti-JCV antibodies and antigen-binding fragments thereof, as well as vectors, host cells, and expression systems. The term "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

In some embodiments, provided is a nucleic acid sequence comprising one or more of SEQ ID NO:105-140.

The nucleic acids encoding anti-JCV antibodies and antigen-binding fragments thereof may be, e.g., DNA, cDNA, RNA, synthetically produced DNA or RNA, or a recombinantly produced chimeric nucleic acid molecule comprising any of those polynucleotides either alone or in combination. For example, provided is an expression vector or set of expression vectors comprising a polynucleotide sequence encoding an anti-JCV antibody or antigen-binding fragment thereof described herein operably linked to expression control sequences suitable for expression in a eukaryotic and/or prokaryotic host cell.

The term "vector" refers to a nucleic acid molecule capable of transporting another nucleic acid to which it has been linked. A "vector" includes, but is not limited to, a viral vector, a plasmid, a RNA vector or a linear or circular DNA or RNA molecule which may consists of a chromosomal, non-chromosomal, semi-synthetic or synthetic nucleic acids. In some embodiments, the employed vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e.g., adeno associated viruses, AAV), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, and spumavirus.

A variety of expression vectors have been developed for the efficient synthesis of anti-JCV antibodies and antigen-binding fragments thereof in prokaryotic cells such as bacteria and in eukaryotic systems, including but not limited to yeast and mammalian cell culture systems have been developed. The vectors can comprise segments of chromosomal, non-chromosomal and synthetic DNA sequences. Also provided are cells comprising expression vectors for the expression of the contemplated anti-JCV antibodies or antigen-binding fragments thereof.

Antibody Preparation and Expression Systems

The anti-JCV antibodies or antigen-binding fragments thereof of the disclosure are typically produced by recombinant expression. Nucleic acids encoding light and heavy chain variable regions, optionally linked to constant regions, may be inserted into expression vectors. The light and heavy chains can be cloned in the same or different expression vectors. The DNA segments encoding immunoglobulin chains may be operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

The expression of the anti-JCV antibodies and antigen-binding fragments contemplated by the disclosure can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used.

*E. coli* is one prokaryotic host particularly useful for cloning the polynucleotides (e.g., DNA sequences) of the present disclosure. Other microbial hosts suitable for use include bacilli, such as *Bacillus subtilis*, and other enterobacteriaceae, such as *Salmonella, Serratia*, and various *Pseudomonas* species.

Other microbes, such as yeast, are also useful for expression. *Saccharomyces* and *Pichia* are exemplary yeast hosts, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an anti-JCV antibody or antigen-binding fragment thereof of the present disclosure with a specified amino terminus sequence. Moreover, problems associated with retention of initiation codon-derived methionine residues in direct yeast (or bacterial) expression may be avoided. Sabin et al., 7 Bio/Technol. 705 (1989); Miller et al., 7 Bio/Technol. 698 (1989).

Any of a series of yeast gene expression systems incorporating promoter and termination elements from the actively expressed genes coding for glycolytic enzymes produced in large quantities when yeast are grown in mediums rich in glucose can be utilized to obtain recombinant anti-JCV antibodies or antigen-binding fragments thereof of the present disclosure. Known glycolytic genes can also provide very efficient transcriptional control signals. For example, the promoter and terminator signals of the phosphoglycerate kinase gene can be utilized.

Production of anti-JCV antibodies or antigen-binding fragments thereof in insects can be achieved. For example, by infecting the insect host with a baculovirus engineered to express a transmembrane polypeptide by methods known to those of skill. See Ausubel et al., 1987, 1993.

In addition to microorganisms, mammalian tissue culture may also be used to express and produce the anti-JCV antibodies or antigen-binding fragments thereof of the present disclosure (e.g., polynucleotides encoding immunoglobulins or fragments thereof). See Winnacker, From Genes to Clones, VCH Publishers, N.Y., N.Y. (1987). Eukaryotic cells are preferred, because a number of suitable host cell lines capable of secreting heterologous proteins (e.g., intact immunoglobulins) have been developed in the art, and include CHO cell lines, various COS cell lines, HeLa cells, 293 cells, myeloma cell lines, transformed B-cells, and hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., J. Immunol. 148:1149 (1992).

Alternatively, nucleotide sequences encoding anti-JCV antibodies or antigen-binding fragments thereof can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Additionally, plants have emerged as a convenient, safe and economical alternative main-stream expression systems for recombinant antibody production, which are based on large scale culture of microbes or animal cells. Anti-JCV antibodies or antigen-binding fragments thereof can be expressed in plant cell culture, or plants grown conventionally. The expression in plants may be systemic, limited to sub-cellular plastids, or limited to seeds (endosperms). See, e.g., U.S. Patent Pub. No. 2003/0167531; U.S. Pat. Nos. 6,080,560 and 6,512,162; and WO 0129242. Several plant-derived antibodies have reached advanced stages of development, including clinical trials (see, e.g., Biolex, NC).

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., Molecular Cloning: A Laboratory Manual (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

The anti-JCV antibodies and antigen-binding fragments thereof of the disclosure can be expressed using a single vector or set of vectors. When the antibody heavy and light chains are cloned on separate expression vectors, the vectors may be co-transfected to obtain expression and assembly of intact immunoglobulins. Once expressed, the whole antibodies, their dimers, individual light and heavy chains, or other immunoglobulin forms of the present disclosure can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

Antibody Binding

In one embodiment, the disclosure provides anti-JCV antibodies and antigen-binding fragments thereof that bind to JCV. As used herein, "binding" of an anti-JCV antibody or antigen binding fragment thereof includes the selective interaction of the antibody or antigen binding fragment thereof with JCV. Binding therefore includes, e.g., primary and secondary interactions including hydrogen bonds, ionic interactions, salt bridges, as well as hydrophilic and hydrophobic interactions.

In certain embodiments, the anti-JCV antibodies or antigen-binding fragments thereof described herein bind to JCV with a $K_D$ of $10^{-5}$ to $10^{-12}$ mol/l, $10^{-6}$ to $10^{-12}$ mol/l, $10^{-7}$ to $10^{-12}$ mol/l, $10^{-8}$ to $10^{-12}$ mol/l, $10^{-9}$ to $10^{-12}$ mol/l, $10^{-10}$ to $10^{-12}$ mol/l, or $10^{-11}$ to $10^{-12}$ mol/l.

In other embodiments, the anti-JCV antibodies or antigen-binding fragments thereof described herein bind to JCV with a $K_D$ of $10^{-5}$ to $10^{11}$ mol/l, $10^{-6}$ to $10^{11}$ mol/l, $10^{-7}$ to $10^{11}$ mol/l, $10^{-8}$ to $10^{-11}$ mol/l, $10^{-9}$ to $10^{-11}$ mol/l, or $10^{-10}$ to $10^{-11}$ mol/l.

In other embodiments, the anti-JCV antibodies or antigen-binding fragments thereof described herein bind to JCV with a $K_D$ of $10^{-5}$ to $10^{-10}$ mol/l, $10^{-6}$ to $10^{-10}$ mol/l, $10^{-7}$ to $10^{-10}$ mol/l, $10^{-8}$ to $10^{-10}$ mol/l, or $10^{-9}$ to $10^{-10}$ mol/l.

In other embodiments, the anti-JCV antibodies or antigen-binding fragments thereof described herein bind to JCV with a $K_D$ of $10^{-5}$ to $10^{-9}$ mol/l, $10^{-6}$ to $10^{-9}$ mol/l, $10^{-7}$ to $10^{9}$ mol/l, or $10^{-8}$ to $10^{-9}$ mol/l.

In other embodiments, the anti-JCV antibodies or antigen-binding fragments thereof described herein bind to JCV with a $K_D$ of $10^{-5}$ to $10^{-8}$ mol/l, $10^{-6}$ to $10^{-8}$ mol/l, or $10^{-7}$ to $10^{-8}$ mol/l.

Neutralizing Antibodies

In one embodiment, the disclosure provide antibodies and antigen-binding fragments thereof that bind to JCV. In some embodiments, the anti-JCV antibodies and antigen-binding fragments thereof disclosed herein are neutralizing antibodies. As used herein, a "JCV neutralizing antibody or antigen-binding fragment thereof" is an antibody or antigen-binding fragment thereof that reduces or inhibits one or more JCV functions, including, but not limited to, inhibiting JCV replication, proliferation, and/or infectivity. In some embodiments, a JCV neutralizing antibody or antigen-binding fragment thereof induces JCV clearance by the immune system, blocks JCV/receptor interactions, and/or disrupts JCV capsids. In one embodiment, a JCV neutralizing antibody or antigen-binding fragment thereof prevents or reduces interaction of JCV with a cellular surface sialic acid-linked carbohydrate receptor and/or a cellular surface serotonin receptor, such as $5HT_{2A}R$. In one embodiment, a JCV neutralizing antibody or antigen-binding fragment thereof prevents or reduces clathrin-dependent endocytosis of JCV. A reduction in JCV replication, proliferation, infectivity, and/or any other function caused by an anti-JCV antibody or fragment thereof can be a measured (e.g., using an in vitro and/or in vivo assay) by comparing one or more JCV functions in the presence versus the absence of the antibody. In some embodiments, a neutralizing antibody can result in a reduction in one or more virus functions by about 5%, about 10%, about 20%, about 30%, about 40%, about 50%, about 60%, about 70%, about 80%, about 90%, about 95%, or more. By "reducing" is meant the ability to cause an overall decrease of about 20% or greater, 30% or greater, 40% or greater, 45% or greater, 50% or greater, of 55% or greater, of 60% or greater, of 65% or greater, of 70% or greater, or 75%, 80%, 85%, 90%, 95%, or greater, as compared to a control that is not treated.

In one embodiment, the disclosure provides anti-JCV antibodies and antigen-binding fragments thereof that bind to JCV major capsid protein VP1. In some embodiments, the anti-JCV antibody or antigen-binding fragment thereof disclosed herein binds to wild type JCV comprising wild type VP1. The sequence of wild type VP1 is provided as SEQ ID NO:141 (NCBI AAA82101.1 Mad1; also NP_043511.1 (NC_001699).

In some embodiments, the anti-JCV antibody or antigen-binding fragment thereof disclosed herein binds to a mutated or otherwise altered version of JCV. In some embodiments, the anti-JCV antibody or antigen-binding fragment thereof binds to a JCV comprising a VP1 protein that is mutated at positions 55, 60, 122, 265, 267, 269, 271, and/or 283 of the VP1 sequence of SEQ ID NO:141. In some embodiments, the mutations are L55F, S267F and/or S269F. In some embodiments, the anti-JCV antibody or antigen-binding fragment thereof binds to a JCV comprising a VP1 protein that carries a deletion and/or an insertion. In some embodiments, residues 50 and 51 and/or residues 123-125 of the VP1 sequence of SEQ ID NO:141 are deleted.

In one embodiment, the disclosure provides anti-JCV antibodies and antigen-binding fragments thereof that bind to more than one JCV variant. For instance, anti-JCV antibodies and antigen-binding fragments thereof disclosed herein may bind to wild type JCV, a JCV variant comprising a VP1 L55F mutant, a JCV variant comprising a VP1 S267F mutant, and/or a JCV variant comprising a VP1 S269F mutant, or any combination of JCV variants.

In one embodiment, the anti-JCV antibody and antigen-binding fragment thereof is able to cross the blood-brain barrier.

Methods of Use

In one embodiment, the disclosure also provides methods of using the anti-JCV antibodies and antigen-binding fragments thereof disclosed herein.

In one aspect, the disclosure provides a method of neutralizing JCV, the method comprising contacting the virus with one or more of the anti-JCV antibodies or antigen-binding fragments disclosed herein.

In one aspect, the disclosure provides a method of reducing replication, proliferation and/or infectivity of JCV, the methods comprising contacting the virus with one or more of the anti-JCV antibodies or antigen-binding fragments disclosed herein.

In one aspect, the disclosure provides a method of reducing binding of JCV to a cell, reducing infection of a cell by JCV, and/or reducing internalization of a JCV by a cell, the methods comprising contacting the virus with one or more of the anti-JCV antibodies or antigen-binding fragments disclosed herein. In one aspect, the disclosure provides a method of reducing clathrin-dependent endocytosis of JCV, the method comprising contacting the virus with one or more of the anti-JCV antibodies or antigen-binding fragments disclosed herein. In some embodiments, the cell is a kidney epithelial cell, a tonsillar stromal cell, a bone marrow-derived cell, a lymphocyte, a leukocyte, an oligodendrocyte, or an astrocyte.

In one aspect, the disclosure provides a method of blocking of interactions between JCV and a cellular receptor, the method comprising contacting the virus with one or more of the anti-JCV antibodies or antigen-binding fragments disclosed herein. In some embodiments, the receptor is a sialic acid-linked carbohydrate receptor or a cellular surface serotonin receptor, such as 5HT2AR.

Methods of Treatment and Prevention

In one aspect, the disclosure provides anti-JCV antibodies and antigen-binding fragments thereof that are useful for the treatment of subjects in need thereof. The disclosure particularly provides methods and composition for the treatment, for the prevention of PML, and/or for reducing the likelihood of developing PML, the methods comprising administering to the subject an effective amount of one or more of the anti-JCV antibodies or antigen-binding fragments thereof disclosed herein. The administration of the one or more of the anti-JCV antibodies or antigen-binding fragments thereof disclosed herein can occur before, during, or after a diagnosis of PML has been made.

By "subject" is meant a mammal, including, but not limited to, a human or non-human mammal. The mammal may be a commercially farmed animal (such as a horse, a cow, a sheep or a pig), a laboratory animal (such as a mouse or a rat), or a pet (such as a cat, a dog, a rabbit or a guinea pig). The subject is preferably a human. The subject may be male or female. Individuals and patients are also subjects herein.

The terms "treat," "treated," "treating," or "treatment" as used herein refer to a therapeutic treatment, wherein the object is to slow down (lessen) an undesired physiological condition, disorder or disease, or to obtain beneficial or desired clinical results. For the purposes of this disclosure, beneficial or desired clinical results include, but are not limited to, alleviation of symptoms, diminishment of the extent of the condition, disorder or disease, stabilization (i.e., not worsening) of the state of the condition, disorder or disease, slowing of the progression of the condition, disorder or disease, amelioration of the condition, disorder or disease state, remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A treatment of PML can be beneficial even if the administration of one or more anti-JCV antibodies or antigen-binding fragments thereof does not clear all JCV from the subject. In some embodiments, the treatment results in a reduction in viral load, an improved expanded disability status scale score, an improved Karnofsky performance sale index, an improved magnetic resonance imaging (MRI) scan, or an improvement in cognition.

In some embodiments, the disclosure provides therapeutic methods, wherein a therapeutically effective amount of an anti-JCV antibody or antigen-binding fragment thereof is administered to a subject in need thereof. "Therapeutically effective amount" means an amount of an antibody or antigen-binding fragment thereof set forth herein that, when administered to a subject, is effective in producing the desired therapeutic effect. A therapeutically effective amount may also refer to a combination of more than one anti-JCV antibodies or antigen-binding fragments thereof, which in combination lead to the desired therapeutic effect.

The patient may be asymptomatic and/or may have a predisposition to the disease. As such, in one embodiment the disclosure provides methods of reducing the reducing the likelihood, delaying, or preventing the onset of developing PML. The disclosure also provides prophylactic methods, wherein a prophylactically effective amount of an anti-JVC antibody or antigen-binding fragment thereof is be administered to a subject in need thereof. A "prophylactically effective amount" is an amount that prevents, reduces, and/or delays the onset of one or more symptoms of the disease. A prophylactically effective amount may also refer to a combination of more than one anti-JCV antibodies or antigen-binding fragments thereof, which in combination lead to the desired prophylactic effect. Prophylactic and preventive are used interchangeably herein.

In one embodiment, the disclosure provides methods of using one or more of the anti-JCV antibodies and antigen-binding fragments thereof disclosed herein for the treatment of a subject that is infected with JCV or is at risk of being infected with JCV. In some embodiments, the CNS, including the brain, of the subject is infected with JCV or is at risk of being infected with JCV.

In one aspect, the disclosure provides a method of neutralizing JCV in a subject in need thereof, the method comprising administering to the subject an effective amount of one or more anti-JCV antibodies or antigen-binding fragments disclosed herein.

In one aspect, the disclosure provides method of reducing replication, proliferation and/or infectivity of JCV in a subject in need thereof, the methods comprising administering to the subject an effective amount of one or more anti-JCV antibodies or antigen-binding fragments disclosed herein. In one aspect, the disclosure provides a method of reducing JCV titers in a subject in need thereof, the method comprising administering to the subject an effective amount of one or more anti-JCV antibodies or antigen-binding fragments disclosed herein. In one aspect, the disclosure provides a method of reducing dissemination of JCV to the CNS in a subject in need thereof, the method comprising administering to the subject an effective amount of one or more anti-JCV antibodies or antigen-binding fragments disclosed herein.

In one aspect, the disclosure provides a method of reducing binding of JCV to a cell, reducing infection of a cell by JCV, and/or reducing internalization of a JCV by a cell in a subject in need thereof, the methods comprising administering to the subject an effective amount of one or more anti-JCV antibodies or antigen-binding fragments disclosed herein. In one aspect, the disclosure provides a method of reducing clathrin-dependent endocytosis of JCV in a subject in need thereof, the method comprising administering to the subject an effective amount of one or more anti-JCV antibodies or antigen-binding fragments disclosed herein. In some embodiments, the cell is a kidney epithelial cell, a tonsillar stromal cell, a bone marrow-derived cell, a lymphocyte, a leukocyte, an oligodendrocyte, or an astrocyte. In one aspect, the disclosure provides a method of blocking of interactions between JCV and a cellular receptor in a subject in need thereof, the method comprising administering to the subject an effective amount of one or more anti-JCV antibodies or antigen-binding fragments disclosed herein. In some embodiments, the receptor is a sialic acid-linked carbohydrate receptor or a cellular surface serotonin receptor, such as 5HT2AR.

In one aspect, the disclosure provides a method of reducing or preventing the occurrence, duration, and/or severity of IRIS in a subject in need thereof, the method comprising administering to the subject an effective amount of one or more anti-JCV antibodies or antigen-binding fragments disclosed herein. In some embodiments, the one or more anti-JCV antibodies or antigen-binding fragments are administered before and/or after the subject has developed IRIS. IRIS can occur when a subject infected with HIV receives anti-retroviral therapy, which unmasks a JCV infection previously not identified in the patient. IRIS can also occur in patients after discontinuation of treatment with an immunosuppressing and/or immunomodulatory agent.

In one embodiment, the disclosure provides a method of treating PML in a subject in need thereof, the method comprising administering to the subject an effective amount of an anti-JCV antibody or antigen-binding fragment thereof disclosed herein. In some embodiments, the method further comprises administering one or more additional anti-JCV antibodies or antigen-binding fragments thereof disclosed herein.

In some embodiments, the subject has previously received, is currently receiving and/or will subsequently receive treatment with an anti-retroviral agent. In some embodiments, the retroviral agent is a nucleoside and nucleotide reverse transcriptase inhibitor, a non-nucleoside reverse transcriptase inhibitor, a protease inhibitor, or and a drugs that interferes with retroviral entry, such as a fusion inhibitor and CCR5 antagonist.

In some embodiments, the subject has previously received and/or is currently receiving treatment with an immunosuppressing agent and/or an immunomodulatory agent. In some embodiments, the immunosuppressing and/or immunomodulatory agent is a modulator of TNF-α, BLys, α4-integrin, CTLA-4, CD11a, CD20, CD30, CD52, sphingosine 1-phosphate receptor, inosine monophosphate dehydrogenase, janus kinase, and/or dihydroorotate dehydrogenase. In some embodiments, the immunosuppressing and/or immunomodulatory agent is Natalizumab, Efalizumab, Belimumab, Rituximab, Fingolimod, Dimethylfumarate, Alemtuzumab, Adalimumab, Etanercept, Ofatumumab, Mycophenolate mofetil, Betalacept, Brentuximab, Fludarabine, Ruxolitinib, Leflunomide, and/or Infliximab. In one embodiment, the central nervous system of the subject is infected with JCV. In one embodiment, the subject has MS and has previously received and/or is currently receiving treatment with a modulator of α4-integrin.

In one embodiment, the disclosure provides a method of treating PML in a subject in need thereof, the method comprising administering to the subject an effective amount of one or more anti-JCV antibodies or antigen-binding fragments thereof disclosed herein, wherein the subject has an immune deficiency. In one embodiment, the immune deficiency is a hereditary immune deficiency, including, but not limited to, adenosine deaminase deficiency, CD40 ligand deficiency, combined immune deficiency, common variable immune deficiency, dedicator of cytokinesis 8 protein (DOCK8) deficiency, gamma heavy chain disease, hyper-IgM syndrome, immunodeficiency-centromeric instability-facial dysmorphism syndrome, purine nucleoside phosphorylase deficiency, severe combined immune deficiency, signal transducer and activator of transcription 1 gain-of-function immune deficiency, Wiskott-Aldrich syndrome, X-linked agammaglobulinaemia, idiopathic CD4+ lymphopenia, and sarcoidosis. In one embodiment, the immune deficiency is an acquired immune deficiency. In one embodiment, the subject is infected with HIV and/or has AIDS.

In one embodiment, the disclosure provides a method of treating PML in a subject in need thereof, the method comprising administering to the subject an effective amount of one or more anti-JCV antibodies or antigen-binding fragments thereof disclosed herein, wherein the subject has cancer, including, but not limited to glioma, glioblastoma, thymoma, mesothelioma, sarcoma, uterine carcinosarcoma, chromophobe renal cell carcinoma, adenoid cystic carcinoma, acute myeloid leukemia, melanoma, uveal melanoma, papillary renal cell carcinoma, clear cell renal cell carcinoma, chloangiocarcinoma, lung adenocarcinoma, diffuse large B-cell lymphoma, pheochromocytoma and paraganglioma, pancreatic cancer, thyroid cancer, lung cancer, colorectal cancer, squamous cancer, breast cancer, prostate cancer, bladder cancer, gastric cancer, testicular germ cell cancer, ovarian cancer, head and neck cancer, uterine cancer, cervical cancer, or liver cancer.

In one embodiment, the disclosure provides a method of treating PML in a subject in need thereof, the method comprising administering to the subject an effective amount of one or more anti-JCV antibodies or antigen-binding fragments thereof disclosed herein, wherein the subject has an autoimmune disease, including, but not limited to, rheumatoid arthritis, psoriatic arthritis, psoriasis, juvenile idiopathic arthritis, inflammatory bowel disease, ankylosing spondylitis, and multiple sclerosis. In a preferred embodiment, the autoimmune disease is multiple sclerosis or Chron's disease.

In one embodiment, the disclosure provides a method of treating PML in a subject in need thereof, the method comprising administering to the subject an effective amount of one or more anti-JCV antibodies or antigen-binding fragments thereof disclosed herein, wherein the subject has received, is receiving, or will receive a transplant. In some embodiments, the transplant is a haematopoietic stem cell transplant, a bone marrow transplant, and/or an organ transplant.

In some embodiments, the disclosure provides a method of preventing and/or reducing the likelihood of developing PML, and/or preventing or reducing the likelihood of a JCV infection in a subject in need thereof, the method comprising administering to the subject an effective amount of an anti-JCV antibody or antigen-binding fragment thereof disclosed herein. In some embodiments, the method further comprises administering one or more additional anti-JCV antibodies or antigen-binding fragments thereof disclosed herein. In one embodiment, the central nervous system of the subject is infected with JCV.

In one embodiment, the disclosure provides a method of preventing and/or reducing the likelihood of developing PML, and/or preventing or reducing the likelihood of a JCV infection in a subject in need thereof, the method comprising administering to the subject an effective amount of one or more anti-JCV antibodies or antigen-binding fragments thereof disclosed herein, wherein the subject has an immune deficiency. In one embodiment, the immune deficiency is a hereditary immune deficiency, including, but not limited to, adenosine deaminase deficiency, CD40 ligand deficiency, combined immune deficiency, common variable immune deficiency, dedicator of cytokinesis 8 protein (DOCK8) deficiency, gamma heavy chain disease, hyper-IgM syndrome, immunodeficiency-centromeric instability-facial dysmorphism syndrome, purine nucleoside phosphorylase deficiency, severe combined immune deficiency, signal transducer and activator of transcription 1 gain-of-function immune deficiency, Wiskott-Aldrich syndrome, X-linked agammaglobulinaemia, idiopathic CD4+ lymphopenia, and sarcoidosis. In one embodiment, the immune deficiency is an acquired immune deficiency. In one embodiment, the subject is infected with HIV and/or has AIDS.

In one embodiment, the disclosure provides a method of preventing and/or reducing the likelihood of developing PML, and/or preventing or reducing the likelihood of a JCV infection in a subject in need thereof, the method comprising administering to the subject an effective amount of one or more anti-JCV antibodies or antigen-binding fragments thereof disclosed herein, wherein the subject has cancer, including, but not limited to glioma, glioblastoma, thymoma, mesothelioma, sarcoma, uterine carcinosarcoma, chromophobe renal cell carcinoma, adenoid cystic carcinoma, acute myeloid leukemia, melanoma, uveal melanoma, papillary renal cell carcinoma, clear cell renal cell carcinoma, chloangiocarcinoma, lung adenocarcinoma, diffuse large B-cell lymphoma, pheochromocytoma and paraganglioma, pancreatic cancer, thyroid cancer, lung cancer, colorectal cancer, squamous cancer, breast cancer, prostate cancer, bladder cancer, gastric cancer, testicular germ cell cancer, ovarian cancer, head and neck cancer, uterine cancer, cervical cancer, or liver cancer.

In one embodiment, the disclosure provides a method of preventing and/or reducing the likelihood of developing PML, and/or preventing or reducing the likelihood of a JCV infection in a subject in need thereof, the method comprising administering to the subject an effective amount of one or more anti-JCV antibodies or antigen-binding fragments thereof disclosed herein, wherein the subject has an autoimmune disease, including, but not limited to, rheumatoid arthritis, psoriatic arthritis, psoriasis, juvenile idiopathic arthritis, inflammatory bowel disease, ankylosing spondylitis, and multiple sclerosis. In a preferred embodiment, the autoimmune disease is multiple sclerosis or Chron's disease.

In one embodiment, the disclosure provides a method of preventing and/or reducing the likelihood of developing PML, and/or preventing or reducing the likelihood of a JCV infection in a subject in need thereof, the method comprising administering to the subject an effective amount of one or more anti-JCV antibodies or antigen-binding fragments thereof disclosed herein, wherein the subject has received, is receiving, or will receive a transplant. In some embodiments, the transplant is a haematopoietic stem cell transplant, a bone marrow transplant, and/or an organ transplant.

In one embodiment, the disclosure provides a method of preventing and/or reducing the likelihood of developing PML, and/or preventing or reducing the likelihood of a JCV infection in a subject in need thereof, the method comprising administering to the subject an effective amount of one or more anti-JCV antibodies or antigen-binding fragments thereof disclosed herein, wherein the administration of the antibody or antigen-binding fragment occurs before administering an immunosuppressing agent and/or an immunomodulatory agent to the subject. In some embodiments, one or more anti-JCV antibodies or antigen-binding fragments thereof are further administered during and/or after administration of the immunosuppressing agent and/or immunomodulatory agent. In some embodiment, the immunosuppressing and/or immunomodulatory agent is a modulator of TNF-α, BLys, α4-integrin, CTLA-4, CD11a, CD20, CD30, CD52, sphingosine 1-phosphate receptor, inosine monophosphate dehydrogenase, janus kinase, and/or dihydroorotate dehydrogenase. In some embodiment, the immunosuppressing and/or immunomodulatory agent is Natalizumab, Efalizumab, Belimumab, Rituximab, Fingolimod, Dimethylfumarate, Alemtuzumab, Adalimumab, Etanercept, Ofatumumab, Mycophenolate mofetil, Betalacept, Brentuximab, Fludarabine, Ruxolitinib, Leflunomide, and/or Infliximab. In one embodiment, the subject has multiple sclerosis and has previously received, is currently receiving, and/or will subsequently receive treatment with a modulator of α4-integrin.

In one embodiment, the disclosure provides a method of preventing and/or reducing the likelihood of developing PML, and/or preventing or reducing the likelihood of a JCV infection in a subject in need thereof, the method comprising administering to the subject an effective amount of one or more anti-JCV antibodies or antigen-binding fragments thereof disclosed herein, wherein the administration of one or more anti-JCV antibodies or antigen-binding fragments thereof occurs before administering an anti-retroviral agent to the subject. In some embodiments, the one or more anti-JCV antibodies or antigen-binding fragments thereof are further administered during and/or after administration of the anti-retroviral agent. In some embodiments, the retroviral agent is a nucleoside and nucleotide reverse transcriptase inhibitor, a non-nucleoside reverse transcriptase inhibitor, a protease inhibitor, or and a drugs that interferes with retroviral entry, such as a fusion inhibitor and CCR5 antagonist.

In one embodiment, the disclosure provides a method of preventing and/or reducing the likelihood of developing PML, and/or preventing or reducing the likelihood of a JCV infection in a subject in need thereof, the method comprising administering to the subject an effective amount of one or more anti-JCV antibodies or antigen-binding fragments thereof disclosed herein, wherein the administration of the antibody or antigen-binding fragment occurs before subjecting the subject to a cell or organ transplantation. In some embodiments, the one or more anti-JCV antibodies or antigen-binding fragments thereof are further administered during and/or after subjecting the subject to the cell or organ transplantation.

In one embodiment, the disclosure provides a method of treating PML, the method comprising administering to the subject an effective amount of a vector or set of vectors encoding one or more anti-JCV antibodies or antigen-binding fragments thereof disclosed herein.

In one embodiment, the disclosure provides a method of preventing and/or reducing the likelihood of developing PML, and/or preventing or reducing the likelihood of a JCV infection, the method comprising administering to the subject an effective amount of a vector or set of vectors encoding one or more anti-JCV antibodies or antigen-binding fragments thereof disclosed herein.

Methods of Monitoring Patients

The disclosure also provides a method comprising a step of identifying whether or not a subject is at risk of developing or has an infection with JCV. The disclosure also provides a method comprising a step of identifying whether or not a subject is at risk of developing or has PML. In some embodiments, the JCV status of a subject may be determined and/or monitored. Also provided herein are also methods of identifying patient populations that are likely to respond to treatment with the anti-JCV antibodies or antigen-binding fragments disclosed herein.

In some embodiments, a patient that is receiving treatment with an immunosuppressing agent and/or immunomodulatory agent is monitored for one or more signs or symptoms of a JCV-associated condition (e.g., PML). In one embodiment, if a sign or symptom is detected, one or more anti-JCV antibodies or antigen-binding fragments thereof disclosed herein are administered. In some embodiments, the treatment with the immunosuppressing agent and/or immunomodulatory agent is suspended or reduced to allow the patient's immune system to recover and counter a JCV infection.

Combination Therapy

The anti-JCV antibodies and antigen-binding fragments thereof disclosed herein may be administered in combination with other therapeutic agents for the treatment of PML and/or infection with JCV. If one or more agents are administered to the patient—such as one or more anti-JCV antibodies or antigen-binding fragments disclosed herein, one or more additional therapeutic agents for the treatment of PML and/or infection with JCV, immunosuppressing agents, immunomodulatory agents, and/or anti-retroviral agents, or any combination thereof—the administration may occur concurrently or consecutively. The administration of one or more anti-JCV antibodies or antigen-binding fragments disclosed herein and the additional therapeutic agent or agents may be separately or as a mixture.

Pharmaceutical Compositions

In another aspect, the disclosure provides pharmaceutically acceptable compositions that comprise a therapeutically effective amount of an anti-JCV antibody or antigen-binding fragment thereof is described herein formulated together with one or more pharmaceutically acceptable excipients.

The dosage of active agent(s) may vary, depending on the reason for use, the individual subject, and the mode of administration. The dosage may be adjusted based on the subject's weight, the age and health of the subject, and tolerance for the compound(s) or composition. For example, depending on the disease, for an antibody or antigen-binding fragment thereof, this may require 0.1, 1.0, 3.0, 6.0, or 10.0 mg/kg. For an IgG having a molecular mass of 150,000 g/mole (two binding sites), these doses correspond to approximately 18 nM, 180 nM, 540 nM, 1.08 µM, and 1.8 µM of binding sites for a 5 liter blood volume.

The active agent and excipient(s) may be formulated into compositions and dosage forms according to methods known in the art. The pharmaceutical compositions of the disclosure may be specially formulated in solid or liquid form, including those adapted for parenteral administration, for example, by subcutaneous, intratumoral, intramuscular or intravenous injection as, for example, a sterile solution or suspension.

Therapeutic compositions comprising anti-JCV antibodies or antigen-binding fragments thereof may formulated with one or more pharmaceutically-acceptable excipients, which can be a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject, bulking agent, salt, surfactant and/or a preservative. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations.

A bulking agent is a compound which adds mass to a pharmaceutical formulation and contributes to the physical structure of the formulation in lyophilized form. Suitable bulking agents according to the disclosure include mannitol, glycine, polyethylene glycol and sorbitol.

The use of a surfactant can reduce aggregation of the reconstituted protein and/or reduce the formation of particulates in the reconstituted formulation. The amount of surfactant added is such that it reduces aggregation of the reconstituted protein and minimizes the formation of particulates after reconstitution. Suitable surfactants according to the disclosure include polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and polyethyl glycol, polypropyl glycol, and copolymers of ethylene and propylene glycol (e.g. Pluronics, PF68, etc.).

Preservatives may be used in formulations of disclosure. Suitable preservatives for use in the formulation of the disclosure include octadecyldimethylbenzyl ammonium chloride, hexamethonium chloride, benzalkonium chloride (a mixture of alkylbenzyl-dimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

The compositions described herein may comprise one or more of the anti-JCV antibodies or antigen-binding portions thereof disclosed herein at various concentrations. For example, the compositions may comprise one or more antibodies or antigen-binding fragments thereof at 10 mg/ml to 200 mg/ml, 25 mg/ml to 130 mg/ml, 50 mg/ml to 125 mg/ml, 75 mg/ml to 110 mg/ml, or 80 mg/ml to 100 mg/ml. The compositions also may comprise one or more antibodies or antigen-binding fragments thereof at about 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, or 150 mg/ml.

In some embodiments, the compositions comprising the one or more anti-JCV antibodies or antigen-binding fragments thereof and the pharmaceutically acceptable carrier are lyophilized and provided in a composition for reconstitution prior to administration.

Methods of Administration

Therapeutic compositions comprising the contemplated antibody or antigen-binding fragment thereof may be administered in any convenient manner, including by injection, transfusion, implantation or transplantation. The compositions described herein may be administered to a patient subcutaneously, intradermally, intratumorally, intranodally, intramedullary, intramuscularly, intracranially, by intravenous or intralymphatic injection, or intraperitoneally. In one embodiment, the cell compositions of the disclosure are preferably administered by intravenous injection.

In certain embodiments, the anti-JCV antibody or antigen-binding fragment thereof is administered to the mammal by intravenous infusion, i.e., introduction of the antibody or antigen-binding fragment thereof into the vein of a mammal over a certain period of time. In certain embodiments, the period of time is about 5 minutes, about 10 minutes, about 30 minutes, about 1 hour, about 2 hours, about 4 hours, or about 8 hours.

In certain embodiments, a dose of a compound or a composition is administered to a subject every day, every other day, every couple of days, every third day, once a week, twice a week, three times a week, once every two weeks, or once a month. In other embodiments, two, three or four doses of a compound or a composition is administered to a subject every day, every couple of days, every third day, once a week, once every two weeks or once a month. In some embodiments, a dose(s) of a compound or a composition is administered for 2 days, 3 days, 5 days, 7 days, 14 days, 21 days or 28 days. In certain embodiments, a dose of a compound or a composition is administered for 1 month, 1.5 months, 2 months, 2.5 months, 3 months, 4 months, 5 months, 6 months or more.

Assays

The anti-JCV antibodies and antigen-binding fragments disclosed herein can further be used for the detection of wild type and mutant JCV in a subject or in a sample derived from a subject. In some embodiments, the sample is a blood, plasma, urine, saliva, feces, or tissue sample derived from the subject. For instance, the anti-JCV antibodies and antigen-binding fragments disclosed herein may be used in an enzyme-linked immunosorbent assay, for antibody staining, or for flow cytometry.

It is to be understood that this disclosure is not limited to the particular molecules, compositions, methodologies, or protocols described, as these may vary. Any methods and materials similar or equivalent to those described herein can be used in the practice or testing of embodiments of the disclosure. It is further to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes those possibilities).

All other referenced patents and applications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

To facilitate a better understanding of the disclosure, the following examples of specific embodiments are given. The following examples should not be read to limit or define the entire scope of the invention.

EXAMPLES

Example 1: Production of Monoclonal Antibodies Specific for JCV

JCV is a small DNA virus that contains six open reading frames and a non-coding control region (NCCR). The major capsid protein, VP1, is responsible for host cell binding and is associated with VP2 and VP3 in form of 72 pentamers that form the viral capsid. JC viruses isolated from the CNS of infected patients often exhibit mutations in the binding site of VP1. These mutant/PML viruses exhibit a changed viral tropism away from the kidney cells and towards glial cells. Frequently observed JCV mutations include mutations in VP1 residues L55, and S259 (e.g. mutations L55F and S269F). Other mutations include ones at VP1 residues 60, 66, 122, 265, 267, 271, and 283, and deletion of VP1 residues 50, 51 and/or residues 123-125.

Patients will frequently generate antibodies against both wild type as well as a mutant/PML virus. However, a recent study demonstrated that only patients producing antibodies against the mutant/PML virus (found in the CNS) recovered from developing PML. Conversely, patients that only produced antibodies against wild type JCV succumbed to an infection of the CNS with mutant JCV and progressed to full PML (Ray et al., Sci Transl Med 2015; 7(306):306ra151). This suggests that PML results from the appearance of mutant viruses with altered tropism that are not neutralized by a patient's available antibody repertoire. As such, antibodies able to effectively neutralize mutant JCV are urgently needed for the treatment of these patients.

A. Immunizations

For the generation of monoclonal antibodies specific for JCV, Velocimmune® mice (Regeneron) were used. In these mice, six megabases of mouse immune genes are replaced in situ with the corresponding human immune genes, allowing for the generation of human antibodies. Immunization was performed either by electroporation of VP1, VP2, and/or VP3 expression plasmids, or by using pseudovirus preparations produced in 293TT cells, which had been transfected with vectors expressing VP1, VP2 and VP3 as immunogens. 293TT cells are derived from an embryonal kidney cell line transformed with sheared adenovirus type 5 DNA and simian virus-40 (SV40).

B. Screening of Hybridomas and Identification of Monoclonal Antibodies Specific for JCV Individual clones of monoclonal antibodies were selected using the Hamilton ClonaCell EasyPick STAR Robotic System. Hybridomas producing antibodies specific to JCV were identified using at least two of the following three methods:

1. ELISA Screen

Plates coated with virus like particles (VLP) were used to identify monoclonal antibodies that bound to JCV major capsid protein VP1.

2. Flow Cytometry Screen

293TT cells were transfected individually with plasmids coding for wild type JCV VP1, JCV VP1 mutant L55F, or JCV VP1 mutant S269F, respectively. Afterwards, the cells were mixed, permeabilized, and incubated with hybridoma culture supernatants. Binding of the antibodies in the hybridoma culture supernatants to the VP1 variants was determined by the addition of fluorescent-labeled secondary antibody specific for mouse IgG heavy chain of the antibodies.

3. Neutralization Screen

Hybridoma supernatants were added to pre-titrated pseudovirus (expressing wild type VP1 as well as the reporter proteins green fluorescent protein (GFP) and luciferase) and inoculated onto pre-plated ART cells. These cells are derived from an ovarian cancer line transformed with the SV40 large T antigen (LT) expression plasmid pTIH. Delivery of the respective reporter protein (luciferase or GFP) packaged in the pseudovirus was measured as an indicator for the inhibition of JCV infectivity.

Using the above-cited methods, more than 200 antibodies that bound to JCV were identified. 40 clones, which all neutralized wild type JCV pseudovirus, were selected for further characterization (see Table 1).

Example 2: Characterization of Monoclonal Anti-JCV Antibodies

Viral Neutralization Assays

Hybridomas producing monoclonal anti-JCV antibodies were further characterized using a neutralization assay with pseudoviruses (containing GFP or luciferase) or native viruses as outlined below. Assays were performed by mixing anti-JCV-antibody containing hybridoma supernatant or purified antibodies with virus or pseudovirus for a 30-minute incubation. The mixture was then pipetted onto the respective cell lines indicated below. Infection was determined by measuring either GFP fluorescence in infected host cells using flow cytometry (for pseudoviruses expressing GFP), luciferase activity in the culture medium (for pseudoviruses expressing luciferase) or by quantitative real time PCR (qRT-PCR) using RNA isolated from the infected cells (for native virus infection). Assays were read five to seven days after infection.

Virus neutralization was assessed as follows:
1. Wild type pseudovirus neutralization assays were performed in ART cells with GFP fluorescence or luciferase activity as readout.
2. Mutant/PML pseudovirus (e.g. VP1 L55F and S269F mutants) neutralization was performed in solitary fibrous tumor (SFT) cells, with GFP fluorescence or luciferase activity as readout. SFT cells are derived from a gliosarcoma cell line that has been shown to support infectious entry of PML mutant JCV.
3. Native (i.e. not pseudovirus), wild type virus infection was performed in ART cells and qRT-PCR for VP1 and VP2 was used as a readout.
4. Infection with native (i.e. not pseudovirus) mutant/PML virus (e.g. VP1 L55F and S269F) was attempted in SFT cells, using qRT-PCR for VP1 and VP2 was used as the readout. However, the generation of native, mutant/PML virus was inefficient and no infection could be shown.

Table 1 summarizes the ability of anti-JCV antibodies to neutralize the wild type JC virus/pseudovirus and mutant/PML viruses/pseudoviruses L55F and S269F. All of the presented antibodies have heavy chain isotypes IgG1, IgG2a, or IgG2b, and show neutralization of wild type JCV in a pseudovirus assay. Many of the anti-JCV antibodies also neutralize the mutant/PML viruses L55F and/or S269F in a pseudovirus assay.

TABLE 1

Characterization of monoclonal anti-JCV antibodies.

| Hybridoma name | Isotype (heavy/light chain) | Neutralization of wild type JCV | EC50 [pM] | Neutralization of JCV mutant L55F | Neutralization of JCV mutant S269F |
|---|---|---|---|---|---|
| 2A6 | IgG2A/κ | + | 2,710 | + | n/d |
| 5H10 | IgG2A/κ | + | n/d | n/d | n/d |
| 3C3 | IgG3/κ | + | 2,070 | n/d | n/d |
| 3D2 | IgG2A/κ | + | 2,250 | n/d | n/d |
| 6C3 | IgG2A/κ | + | n/d | n/d | n/d |
| 6E3 | IgG2A/κ | + | n/d | n/d | n/d |
| 4F8 | IgG2A/κ | + | 3,700 | n/d | + |
| 2H10 | IgG2A/κ | + | n/d | n/d | n/d |
| 4B7 | IgG2A/κ | + | n/d | n/d | + |
| 3D6 | IgG2A/κ | + | 5,130 | n/d | + |
| 1G9 | IgG2A/k | + | n/d | n/d | n/d |
| 4D4 | n/d | + | n/d | n/d | n/d |
| 1A12 | IgG2A/κ | + | n/d | n/d | n/d |
| 14E9 | IgG2B/κ | + | n/d | n/d | n/d |
| 12G3 | IgG2B/κ | + | n/d | n/d | n/d |
| 12C3 | IgG2B/κ | + | n/d | n/d | n/d |
| 11D6 | IgG2B/κ | + | n/d | n/d | n/d |
| 6A4 | IgG2B/κ | + | 21 | + | + |
| 5H7 | IgG2B/κ | + | n/d | + | + |
| 5F7 | IgG2B/κ | + | n/d | + | + |
| 3H4 | IgG2B/κ | + | 103 | n/d | n/d |
| 3G9 | IgG2B/κ | + | n/d | n/d | n/d |
| 1C4 | IgG2B/κ | + | n/d | n/d | n/d |
| 8A7 | IgG2B/κ | + | 17 | + | + |
| 1A7 | IgG2A/κ | + | 180 | n/d | + |
| 1A10 | IgG3/κ | + | 23 | + | + |
| 1C12 | IgG2A/κ | + | 1170 | n/d | + |
| 1F11 | IgG1/κ | + | 111 | + | + |
| 1G7 | IgG2A/κ | + | >10,000 | + | + |
| 1H10 | IgG2A/κ | + | 155 | +/− | + |
| 2A11 | IgG1/κ | + | 146 | + | + |
| 1E12 | IgG2B/κ | + | 16 | + | + |
| 1G8 | IgG2A/κ | + | 144 | + | n/d |
| 1A3 | IgG2A/κ | + | 301 | + | n/d |
| 1H1 | IgG2A/κ | + | 182 | + | + |
| 4D11 | IgG1/κ | + | 124 | + | + |

TABLE 1-continued

Characterization of monoclonal anti-JCV antibodies.

| Hybridoma name | Isotype (heavy/light chain) | Neutralization of wild type JCV | EC50 [pM] | Neutralization of JCV mutant L55F | Neutralization of JCV mutant S269F |
|---|---|---|---|---|---|
| 4E2 | IgG2A/κ | + | 160 | + | n/d |
| 3D12 | IgG2A/κ | + | 134 | +/− | +/− |
| 1E8 | IgG2A/κ | + | 127 | − | + |

Indicated are isotypes of heavy and light chains of the presented anti-JCV antibodies, as well as the ability of the individual antibodies to neutralize wild type JCV, JCV mutant L55F, and JCV mutant S269F, respectively.
κ = kappa light chain, λ = lambda light chain, n/d = not determined.

A detailed description of the methods employed for the neutralization assays mentioned above can be found below:

1. Production of Pseudovirus Particles

The production of pseudovirus particles containing wild type VP1, VP1 mutant S269F, or VP1 mutant L55F, respectively was performed as previously described (Buck Thompson Curr Protoc Cell Biol 2007, Unit 26.1). Briefly, plasmids expressing VP1, VP2, VP2, and GFP/luciferase were transfected into ITEK-293TT cells (ratio 2:1:1:2) and harvested 48 hours post-transfection. The cells were washed with phosphate-buffered saline (PBS) and suspended in maturation buffer (Dulbecco's phosphate-buffered saline, DPBS, 9.5 mM $MgCl_2$, 0.500 Brij 58, 50 mM ammonia sulfate (pH 9.0), 100 units neuraminidase) for 16 h at 37 TC. The intact cells and insoluble material were removed by centrifugation (16,000×g, 10 min, 4° C.). The supernatant was loaded onto an Opti-prep step-gradient (390%:33%:27%) and centrifuged at 234,000×g for 3.5 h at 16° C. Fractions (~0.5 ml) from the centrifugation tube were collected from the bottom and analyzed for both protein content (SDS-PAGE) and the presence of infectious particles. The latter was done by transducing ART cells.

2. Neutralization of Wild Type Pseudovirus

To measure the inhibition of infection with wild type pseudovirus, ART cells were trypsonized and plated at 10,000 cells/well in a 96 well plate overnight, avoiding the outer wells. The next day, the cells were gently washed once with PBS with a multi-channel pipette. Next, 50 µl of hybridoma supernatants or purified antibody was diluted in ART cell growth media were added to the cells. Next, 50 µl of pseudovirus diluted in ART growth media was added to the cells. Cells were then incubated overnight in a 37° C. incubator. The next day, all media was removed from wells, cells were gently washed once with PBS, and 100 µl fresh ART cell growth media as added to each well. Assay were read after four days. For pseudovirus constructs containing GFP, transduced cells were GFP positive as measured by flow cytometry. Alternatively, the cell culture supernatant was used for a luciferase assay.

3. Luciferase Assay

Four to six days after initial transduction, cell culture supernatants were collected and spun down at 1,000×g to pellet debris. 40 µl supernatant were mixed with 40 µl of 2× renilla luciferase lysis buffer. 50 µl of the supernatant/lysis buffer mixture were transferred to a white bottom plate and the plate was read.

4. Neutralization of Mutant Pseudovirus

For mutant/PML pseudoviruses, SFT cells were treated with 200 µM of the sialyltransferase inhibitor 3Fax-Peracetyl Neu5Ac for 48 h prior to plating. Cells were trypsonized and plated at 5,000 cells/well in a 96 well plate for 6-8 h or until the cells attached. The media was removed and 50 µl antibody supernatant or purified Abs was diluted in SFT growth media was added to the cells. Next, 50 µl of pseudovirus diluted in SFT growth media was added to the cells. 24 h later, all media was removed from wells, cells were washed once with PBS, and 100 µl fresh SFT cell growth media was added to each well. Six days from the start of experiment, the assay was ready for GFP or luciferase analysis.

5. Production of Native Virus

Plasmid VRMC-1™, encoding the native JC virus, was digested with BamH1 restriction enzyme to linearize. Digested DNA was purified using the Qiagen purification kit, religated and concentrated by ethanol precipitation. $1\times10^6$ 293TT cells were transfected with 5 µg of religated plasmid using the lipofectamine 2000 reagent in a 6 well plate. After three days, cells were transferred into T75 flasks and cells collected for DNA. After day six, cells were split into four T175 flasks; fourteen days later the cultures were spun down. Supernatant (containing the viral particles) and cells were saved. DNA was extracted from cells and assayed for expression of VP1 and VP2 by quantitative PCR.

6. Measurement of Wild Type Native Virus Infection by One-Step qRT-PCR

ART cells were trypsinized, washed with R5 medium and counted. Cells were then pre-plated in 6 well plates the day before infection at 80,000 cell/well (500 µl/well). The following day, cells were washed with RPMI (without fetal bovine serum (FBS) and penicillin/streptomycin). Cells were infected with 300 µl mixture of native wild type JCV supernatant+hybridoma supernatant (150 µl virus+150 µl hybridoma supernatant) and incubated for 4 h. The virus was removed, 500 µl/well R5 medium added and the cells incubated for five days. On day six, the cells were trypsinized, washed with PBS, and the total RNA was extracted using the RNEasy Mini kit from QIAGEN. Expression of VP1 and VP2 genes was measured by one-step qRT-PCR using the qScript One-Step SYBR green kit.

Example 3: Characterization of Monoclonal Anti-JCV Antibodies Using Purified Antibodies A. Binding of Anti-JCV Antibodies to Pseudovirus, as Determined by ELISA A lead group of 17 anti-JCV antibodies was selected for further analysis, and the relative affinity of the lead anti-JCV antibodies to each of the pseudoviruses was determined. As shown in Table 2, all 17 antibodies bound to wild type JCV, with the majority of antibodies also binding to JCV mutants L55F and S269F.

To measure the binding affinities of the anti-JCV antibodies, an ELISA was set up using pseudovirus preparations containing VP1 WT, VP1 mutant L55F, or VP1 mutant S269F, respectively (capsid proteins VP2 and VP3 were unmutated in all pseudoviruses). Plates were coated with 400 ng/ml of pseudovirus in PBS incubated overnight and subsequently blocked with PBS containing bovine serum albumin (PBS-BSA). Dilutions of purified antibodies ranging from 2.5 ng/ml to 200 ng/ml were added to the plate and incubated. Binding of the antibodies to the respective virus variant was determined by adding horseradish peroxidase (HIRP) substrate and an HIRP-linked goat antibody targeting the anti-mouse heavy chain of the anti-JCV antibodies.

TABLE 2

Binding of purified anti-JCV antibodies to JCV variants.

| mAB name | Binding to WT VP1: AB conc. [ng/ml] | Binding to WT VP1: EC50 [ng/ml] | Binding to VP1 L55F: AB conc. [ng/ml] | Binding to VP1 L55F: EC50 [ng/ml] | Binding to VP1 S269F: AB conc. [ng/ml] | Binding to VP1 S269F: EC50 [ng/ml] |
|---|---|---|---|---|---|---|
| 1E12 | <7.4 | 8.4 | <2.5 | 7.7 | <7.4 | 8.5 |
| 1F11 | <7.4 | 9.4 | <7.4 | 14.3 | <2.5 | 7.6 |
| 2A11 | <7.4 | 7.4 | <7.4 | 13.6 | <2.5 | 6.8 |
| 1A7 | <22 | 24.7 | NB | NB | <2.5 | 7.4 |
| 1H10 | <22 | 19.3 | NB | NB | <7.4 | 18.5 |
| 8A7 | <7.4 | 8.5 | <67 | 32.4 | <7.4 | 19.3 |
| 6A4 | <7.4 | 10 | ND | ND | ND | ND |
| 2A6 | <200 | 1300 | NB | NB | <22 | 147 |
| 3D2 | <67 | 393 | NB | NB | <22 | 121 |
| 1G8 | <2.5 | 7 | <2.5 | 16.7 | <2.5 | 7.7 |
| 1A3 | <2.5 | 7.1 | <2.5 | 14.3 | <2.5 | 8 |
| 1H1 | <2.5 | 6.5 | <2.5 | 14.7 | <2.5 | 7.5 |
| 4D11 | <2.5 | 1.9 | <2.5 | 7.7 | <2.5 | 6.9 |
| 4E2 | <7.4 | 11.7 | <2.5 | 13.2 | <2.5 | 7.1 |
| 3D12 | <7.4 | 351 | NB | NB | <2.5 | 6 |
| 1E8 | <2.5 | 8 | <22 | 46.5 | <2.5 | 22 |

Shown is the lowest concentration of anti-JCV antibody that gave a clear signal above background ("AB conc."), as well as the corresponding EC50 values ("EC 50") for each antibody. mAB = monoclonal antibody. WT = wild type. ND = not determined. NB = no binding.

B. Binding of Purified Anti-JCV Antibodies to Cells Expressing Different VP1 Variants, as Determined by Flow Cytometry Binding of anti-JCV antibodies to different VP1 variants expressed in transfected 293TT cells (i.e. wild type VP1, and VP1 mutants L55F, S267F, and S269F, respectively) was assessed by flow cytometry, see FIG. 1. All 17 lead anti-JCV antibodies bind to wild type VP1, and a majority of the antibodies bind to the different VP1 mutants tested, including the S267F variant, for which no pseudovirus was available to be used in a neutralization assay.

To determine binding of the anti-JCV antibodies to different VP1 variants, 293TT cells were transfected with VP1 constructs (wild type and VP1 mutants L55F, S267F, and S269F) or mock, using Lipofectamine 2000 as per manufacturers' protocol. 48 h later, cells were trypsinized, washed and permeabilized using BD Biosciences' fixation/permeabilization solution ("cytoperm") as per manufacturer's protocol. After two washes in BD Biosciences' wash buffer "Perm/Wash", cells were blocked for 20 min using goat antisera. After one wash, cells were stained with primary antibody (25 µl supernatant/25 µl cytoperm) for 1 h. After incubation, cells were washed twice with cytoperm and incubated with allophycocyanin (APC)-linked, goat, antibody specific for the mouse IgG gamma chain for 30 min. Cells were washed once before analysis by flow cytometry.

C. Neutralization of Pseudovirus by Anti-JCV Antibodies, as Determined by an Luciferase Assay or Flow Cytometry The ability of purified anti-JCV antibodies to prevent infection by pseudoviruses containing wild type VP1 or VP1 mutants L55F or S269F, respectively, was determined. As shown in Table 3, the majority of anti-JCV antibodies in the panel neutralizes both wild type and mutant S269F virus. A number of the anti-JCV antibodies neutralize the JCV mutant L55F as well. Antibodies binding to wild type VP1, VP1 L55F, and VP1 S269F are highlighted in bold in Table 3. Binding assays for VP1 mutant S267F, which are also included in Table 3, suggest that some of the shown anti-JCV antibodies will neutralize viruses containing the S267F mutation in VP1 as well.

Neutralization assays were performed as described above, and infection with pseudoviruses was measured by luciferase assay or by measuring GFP fluorescence. No pseudovirus neutralization was performed with VP1 mutant S267F, for which the binding of the anti-JCV antibodies was determined by flow cytometry (data are included in Table 3). The pseudovirus assay for VP1 mutant L55F was compromised to some degree due to the poor infection of the pseudovirus prep. A possible explanation is that this virus produces large amounts of non-infectious particles, which also bind the anti-JCV antibody, but are not detected in the neutralization assay, leading to an inflation of the EC50 values shown in Table 3.

TABLE 3

Neutralization of pseudovirus by anti-JCV antibodies.

| mAb name | Neutralization of WT JCV | Neutralization of WT JCV: EC50 [pM] | Neutralization of JCV S269F: EC50 [pM] | Neutralization of JCV L55F: EC50 [pM] | Binding to VP1 S269F |
|---|---|---|---|---|---|
| 2A6 | + | 2710 | NB | NB | + |
| 3D2 | + | 2250 | 733 | NB | + |
| 6A4 | + | 21 | +ND | 171 | + |
| 8A7 | + | 17 | 10.7 | 1040 | + |
| 1A7 | + | 180 | 7 | NB* | − |
| 1F11 | + | 111 | 53 | 76 | + |
| 1H10 | + | 155 | 20.9 | 251 | +/− |
| 2A11 | + | 146 | 250 | 45.5 | + |
| 1E12 | + | 16 | 104.7 | 56.7 | + |

TABLE 3-continued

Neutralization of pseudovirus by anti-JCV antibodies.

| mAb name | Neutralization of WT JCV | Neutralization of WT JCV: EC50 [pM] | Neutralization of JCV S269F: EC50 [pM] | Neutralization of JCV L55F: EC50 [pM] | Binding to VP1 S269F |
|---|---|---|---|---|---|
| 1G8 | + | 144 | 22.7 | 511 | + |
| 1A3 | + | 301 | 37.3 | 6600 | + |
| 1H1 | + | 182 | 55.3 | +ND | + |
| 4D11 | + | 124 | 12.7 | 245 | + |
| 4E2 | + | 160 | 30 | +ND | + |
| 3D12 | + | 134 | 10.7 | 304 | − |
| 1E8 | + | 127 | 55.3 | 3380 | +/− |
| 6G5 | | 3.1 | | | |
| 6H7 | | 0.5 | | | |
| 5G5 | | 0.4 | | | |
| 8C3 | | 14.0 | | | |

Antibodies binding to wild type VP1, VP1 L55F, and VP1 S269F are highlighted in bold.
WT = wild type.
+ND = Antibody neutralizes the indicated JCV, but the EC50 value was not determined.

Figure 2:
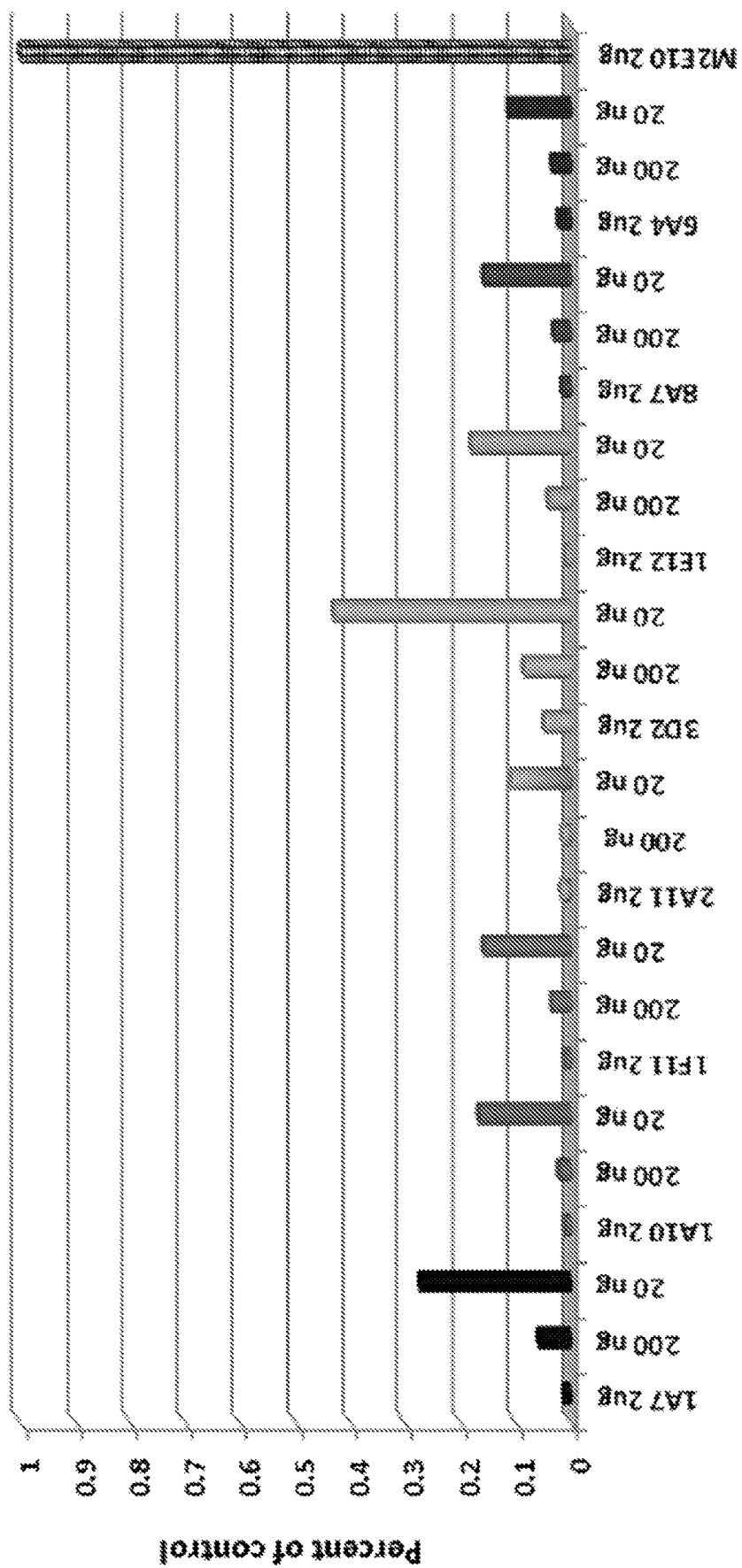

D. Neutralization of Native JC Virus by Anti-JCV Antibodies, as Determined by One-Step RT-PCR Two bacterial clones of wild type and mutant/PML JCV isolated from patients were propagated and viruses tested in a neutralization assay with purified antibody. The mutant/PML JCV virus was not infectious and could not be tested for neutralization. FIG. 2 shows that the anti-JCV antibodies effectively neutralize the wild type virus at very low concentration.

Native JC virus (not pseudovirus) was produced from plasmid encoding the native viral genome. The virus infection was performed by inoculation of ART cells with infectious supernatant collected from transfected 293TT cells. After five days, the cells were lysed and one-step RT-PCR was performed using primer pairs specific for VP1 and VP2. All anti-JCV antibodies that neutralized WT pseudovirus also neutralized the native virus as shown in FIG. 2.

Example 4: Sequencing of Heavy and Light Chain Sequences of Isolated Anti-JCV Antibodies Heavy and light chains of the lead group of antibodies were sequenced and several antibody groups were identified based on similarities in the antibodies' CDR sequences. Some of the CDRs show amino acid variations in at certain positions while retaining specificity for JCV. These observed CDR variations are summarized in form of CDR motifs, see Table 4 and Table 5. The amino acid and nucleic acid sequences for the heavy and light variable chains of the lead antibodies are shown in Table 6.

Heavy and light chains were sequenced by performing total RNA extractions on hybridoma cells, followed by single stand cDNA conversion and 5' RACE PCR for $V_H$ and $V_\kappa$ amplification. Briefly, total RNA was extracted using an Rneasy Mini Kit (Qiagen), following the manufacturer's protocol. The RNA was then used as a template for single strand cDNA conversion and 5'RACE utilizing the SMART 5'RACE kit (Clontech/Takara), following the manufacturer's protocol, allowing complete amplification of the 5' end of the genes. To facilitate both single strand cDNA conversion and the accompanying 5'RACE PCR, isotype specific 3' primers were developed in conserved regions of the CH1 of each of the major mouse antibody isotypes: G1, G2a (G2c), G2b, G3, κ, and λ. Total RNA from each of the hybridomas were paired with the unique heavy and light isotype 3' primers based on isotyping data of hybridoma supernatants. Following 5' RACE PCR, products were cleaned using a PCR Purification Kit (Qiagen). At least 20 ng of PCR product was submitted for Sanger sequencing with a nested isotype specific 3' primer (GeneWiz, South Plainfield, N.J.). Sequencing results were blasted against the IMGT human database and junction analysis was performed using IMGT V-Quest (www.imgt.org).

TABLE 4

Heavy chain CDR sequences of anti-JCV antibodies. SEQ ID NOs are indicated.

| mAb clone | CDR1H SEQ | Sequence | CDR2H SEQ | Sequence | CR3H SEQ | Sequence |
|---|---|---|---|---|---|---|
| 1F11 | 1 | GFTFSDLY | 12 | ISTSGRTI | 23 | AGDYYDNSGWDY |
| 1A3 | 2 | EITFSDYY | 12 | ISTSGRTI | 24 | ASDFYDNSGWEY |
| 4D11 | 3 | GFTFSDHY | 12 | ISTSGRTI | 25 | ASDYYDNSGWYY |
| 2A11/6H7 | 3 | GFTFSDHY | 12 | ISTSGRTI | 26 | ASDYYDNVGWNY |
| 1E8 | 3 | GFTFSDHY | 13 | ISTSGSTI | 27 | ASDYYDNSGWNY |
| 1E12 | 3 | GFTFSDHY | 14 | ISTGGRTI | 28 | ASDYYDNVGWDY |
| 1G8/ | 4 | GFTFSDFY | 15 | ISFSGRAI | 28 | ASDYYDNVGWDY |

TABLE 4-continued

Heavy chain CDR sequences of anti-JCV antibodies. SEQ ID NOs are indicated.

| mAb clone | CDR1H SEQ | CDR1H Sequence | CDR2H SEQ | CDR2H Sequence | CR3H SEQ | CR3H Sequence |
|---|---|---|---|---|---|---|
| 1H1/ 4E2 | | | | | | |
| 8C3 | 3 | GFTFSDHY | 12 | ISTSGRTI | 28 | ASDYYDNVGWDY |
| 5G5 | 5 | GITFSDLY | 12 | ISTSGRTI | 23 | AGDYYDNSGWDY |
| CDR motif | 56 | $X_1X_2TFSDX_3Y$ wherein $X_1$ is G or E; wherein $X_2$ is F or 1; and wherein $X_3$ is H, L, Y, or F | 58 | $ISX_4X_5GX_6X_7I$ wherein $X_4$ is T or F; wherein $X_5$ is S or G; wherein $X_6$ is R or S; wherein $X_7$ is T or A | 61 | $AX_8DX_9YDNX_{10}GWX_{11}Y$ wherein $X_8$ is G or S; wherein $X_9$ is Y or F; wherein $X_{10}$ is S or V; wherein $X_{11}$ is D, E, Y, or N |
| 8A7 | 6 | GGSISSNY | 16 | IYYSGST | 29 | ARRGFEQQLSYYYYYGLDV |
| 6A4 | 6 | GGSISSNY | 16 | IYYSGST | 30 | ARRGFEQQLSYYYYYGMDV |
| CDR motif | | | | | 62 | ARRGFEQQLSYYYYYG$X_{14}$DV wherein $X_{14}$ is L or M |
| 1A7 | 7 | GYTFTFYD | 17 | MNPNSGNT | 31 | ARKIWVGHTTFDR |
| 3D12 | 8 | GYTFTNYD | 18 | VNPNSGNS | 32 | ARKIWVGTTIFDY |
| 6G5 | 8 | GYTFTNYD | 19 | TNPNSGNS | 32 | ARKIWVGTTIFDY |
| CDR motif | 57 | GYTFT$X_{17}$YD wherein $X_{17}$ is F or N | 59 | $X_{18}$NPNSGN$X_{19}$ wherein $X_{18}$ is M or V; wherein $X_{19}$ is T or S | 63 | ARKIWVG$X_{20}$T$X_{21}$FD$X_{22}$ wherein $X_{20}$ is H or T; wherein $X_{21}$ is T or 1; wherein $X_{22}$ is R or Y |
| CDR motif | | | 60 | $X_{23}$NPNSGN$X_{24}$ wherein $X_{23}$ is M, V or T; wherein $X_{24}$ is T or S | | |
| 2A6 | 9 | GGSFSGYY | 20 | INHGGST | 33 | ARGWGGQVAHWFDP |
| 3D2 | 10 | GGSFSSYY | 21 | INHSGST | 34 | ARWGIAADYGMDV |
| 1H10 | 11 | GFTLSTYA | 22 | ISGTGLST | 35 | AKGLELFYFYYGMDV |

TABLE 5

Light chain CDR sequences of anti-JCV antibodies. SEQ ID NOs are indicated for amino acid sequences longer than three amino acids.

| mAb clone | CDR1L SEQ ID NO: | CDR1L Sequence | CDR2L SEQ ID NO: | CDR2L Sequence | CR3L SEQ ID NO: | CR3L Sequence |
|---|---|---|---|---|---|---|
| 1F11/ 1A3/ 4D11/ 2A11/ 6H7/ 1G8/ 1H1/ 4E2/ 5G5 | 36 | QSLVYSDGNTY | n/a | KVS | 45 | MQGTHWPRT |
| 1E8 | 36 | QSLVYSDGNTY | n/a | KVS | 46 | MQGSHWPRT |
| 1E12 | 37 | QSLIYSDGNTY | n/a | KVS | 45 | MQGTHWPRT |

TABLE 5-continued

Light chain CDR sequences of anti-JCV antibodies. SEQ ID NOs are indicated for amino acid sequences longer than three amino acids.

| mAb clone | CDR1L SEQ ID NO: | Sequence | CDR2L SEQ ID NO: | Sequence | CR3L SEQ ID NO: | Sequence |
|---|---|---|---|---|---|---|
| 8C3 | 38 | QSLLYSDGNTY | | KVS | 47 | MQGAHWPRT |
| CDR motif | 64 | QSLX$_{12}$YSDGNTY wherein X$_{12}$ is V or I | | | 66 | MQGX$_{13}$HWPRT wherein X$_{13}$ is T or S |
| CDR motif | 65 | QSLX$_{25}$YSDGNTY wherein X$_{25}$ is V or I or L | | | 67 | MQGX$_{26}$HWPRT wherein X$_{26}$ is T or S or A |
| 8A7 | 39 | QSVLYSSNNKNY | n/a | WAS | 48 | QQYYTFPWT |
| 6A4 | 39 | QSVLYSSNNKNY | n/a | WAS | 49 | QQYYSTPWT |
| CDR motif | | | | | 68 | QQYYX$_{15}$X$_{16}$PWT wherein X$_{15}$ is T or S; and wherein X$_{16}$ is T or F |
| 1A7 | 40 | QSISGY | n/a | AAS | 50 | QQTYNIPFT |
| 3D12 | 41 | QSIYRF | n/a | AAS | 51 | QQSDGPPLT |
| 6G5 | 41 | QSIYRF | n/a | AVS | 52 | QQSDSPPLT |
| 2A6 | 42 | QSVLFSSNNQNY | n/a | WAS | 53 | QQYYSLPYT |
| 3D2 | 43 | QSVSSSY | n/a | GAS | 54 | QQYGTSPWT |
| 1H10 | 44 | QSVSSTY | n/a | GTS | 55 | QQYGRSLI |

TABLE 6

Heavy and light variable chain amino acid and nucleic acid sequences sequences of anti-JCV antibodies.

| mAb clone | Chain | Amino acid sequence (SEQ ID NO) | Nucleic acid sequence (SEQ ID NO) |
|---|---|---|---|
| 1F11 | H | 69 | 105 |
| 1F11 | L | 70 | 106 |
| 1A3 | H | 71 | 107 |
| 1A3 | L | 72 | 108 |
| 4D11 | H | 73 | 109 |
| 4D11 | L | 74 | 110 |
| 2A11 | H | 75 | 111 |
| 2A11 | L | 76 | 112 |
| 1E8 | H | 77 | 113 |
| 1E8 | L | 78 | 114 |
| 1E12 | H | 79 | 115 |
| 1E12 | L | 80 | 116 |
| 6H7 | H | 81 | 117 |
| 6H7 | L | 82 | 118 |
| 1G8/1H1/4E2 | H | 83 | 119 |
| 1G8/1H1/4E2 | L | 84 | 120 |
| 8A7 | H | 85 | 121 |
| 8A7 | L | 86 | 122 |
| 6A4 | H | 87 | 123 |
| 6A4 | L | 88 | 124 |
| 1A7 | H | 89 | 125 |
| 1A7 | L | 90 | 126 |
| 3D12 | H | 91 | 127 |
| 3D12 | L | 92 | 128 |
| 2A6 | H | 93 | 129 |
| 2A6 | L | 94 | 130 |
| 3D2 | H | 95 | 131 |
| 3D2 | L | 96 | 132 |
| 1H10 | H | 97 | 133 |
| 1H10 | L | 98 | 134 |
| 8C3 | H | 99 | 135 |
| 8C3 | L | 100 | 136 |
| 5G5 | H | 101 | 137 |
| 5G5 | L | 102 | 138 |
| 6G5 | H | 103 | 139 |
| 6G5 | L | 104 | 140 |

H = Heavy variable chain.
L = light variable chain.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:

1. An antibody or antigen-binding fragment thereof which binds to the John Cunningham virus (JCV), the antibody or antigen-binding fragment thereof comprising a heavy chain variable region and a light chain variable region;
wherein each of the heavy chain and the light chain variable regions comprises a CDR1, CDR2, and CDR3; and wherein:
(a) CDR1H of the antibody or antigen-binding fragment thereof comprises SEQ ID NO:5, CDR2H comprises SEQ ID NO:12, CDR3H comprises SEQ ID NO:23, CDR1L comprises SEQ ID NO:36, CDR2L comprises the sequence KVS, and CDR3L comprises SEQ ID NO:45;
(b) CDR1H of the antibody or antigen-binding fragment thereof comprises SEQ ID NO:1, CDR2H comprises SEQ ID NO:12, CDR3H comprises SEQ ID NO:23, CDR1L comprises SEQ ID NO:36, CDR2L comprises the sequence KVS, and CDR3L comprises SEQ ID NO:45;
(c) CDR1H of the antibody or antigen-binding fragment thereof comprises SEQ ID NO:3, CDR2H comprises SEQ ID NO:12, CDR3H comprises SEQ ID NO:25, CDR1L comprises SEQ ID NO:36, CDR2L comprises the sequence KVS, and CDR3L comprises SEQ ID NO:45;
(d) CDR1H of the antibody or antigen-binding fragment thereof comprises SEQ ID NO:3, CDR2H comprises SEQ ID NO:12, CDR3H comprises SEQ ID NO:26, CDR1L comprises SEQ ID NO:36, CDR2L comprises the sequence KVS, and CDR3L comprises SEQ ID NO:45;
(e) CDR1H of the antibody or antigen-binding fragment thereof comprises SEQ ID NO:3, CDR2H comprises SEQ ID NO:14, CDR3H comprises SEQ ID NO:28, CDR1L comprises SEQ ID NO:37, CDR2L comprises the sequence KVS, and CDR3L comprises SEQ ID NO:45;
(f) CDR1H of the antibody or antigen-binding fragment thereof comprises SEQ ID NO:4, CDR2H comprises SEQ ID NO:15, CDR3H comprises SEQ ID NO:28, CDR1L comprises SEQ ID NO:36, CDR2L comprises the sequence KVS, and CDR3L comprises SEQ ID NO:45;
(g) CDR1H of the antibody or antigen-binding fragment thereof comprises SEQ ID NO:6, CDR2H comprises SEQ ID NO:16, CDR3H comprises SEQ ID NO:29, CDR1L comprises SEQ ID NO:39, CDR2L comprises the sequence WAS, CDR3L comprises SEQ ID NO: 48;

(h) CDR1H of the antibody or antigen-binding fragment thereof comprises SEQ ID NO:6, CDR2H comprises SEQ ID NO:16, CDR3H comprises SEQ ID NO:30, CDR1L comprises SEQ ID NO:39, CDR2L comprises the sequence WAS, CDR3L comprises SEQ ID NO: 49;
(i) CDR1H of the antibody or antigen-binding fragment thereof comprises SEQ ID NO:8, CDR2H comprises SEQ ID NO:18, CDR3H comprises SEQ ID NO:32, CDR1L comprises SEQ ID NO:41, CDR2L comprises the sequence AAS, and CDR3L comprises SEQ ID NO:51;
(j) CDR1H of the antibody or antigen-binding fragment thereof comprises SEQ ID NO:8, CDR2H comprises SEQ ID NO:19, CDR3H comprises SEQ ID NO:32, CDR1L comprises SEQ ID NO:41, CDR2L comprises the sequence AVS, and CDR3L comprises SEQ ID NO:52;
(k) CDR1H of the antibody or antigen-binding fragment thereof comprises SEQ ID NO:11, CDR2H comprises SEQ ID NO:22, CDR3H comprises SEQ ID NO:35, CDR1L comprises SEQ ID NO:44, CDR2L comprises the sequence GTS, and CDR3L comprises SEQ ID NO:55;
(l) CDR1H of the antibody or antigen-binding fragment thereof comprises SEQ ID NO:9, CDR2H comprises SEQ ID NO:20, CDR3H comprises SEQ ID NO:33, CDR1L comprises SEQ ID NO:42, CDR2L comprises the sequence WAS, and CDR3L comprises SEQ ID NO:53; or
(m) CDR1H of the antibody or antigen-binding fragment thereof comprises SEQ ID NO:10, CDR2H comprises SEQ ID NO:21, CDR3H comprises SEQ ID NO:34, CDR1L comprises SEQ ID NO:43, CDR2L comprises the sequence GAS, and CDR3L comprises SEQ ID NO:54.

2. The antibody or antigen-binding fragment thereof according to claim 1, wherein:
(a) the heavy chain variable region comprises a sequence that is at least 90% identical to SEQ ID NO: 101, and wherein the light chain variable region comprises a sequence that is at least 90% identical to SEQ ID NO:102;
(b) the heavy chain variable region comprises a sequence that is at least 90% identical to SEQ ID NO: 69, and wherein the light chain variable region comprises a sequence that is at least 90% identical to SEQ ID NO:70;
(c) the heavy chain variable region comprises a sequence that is at least 90% identical to SEQ ID NO: 73, and wherein the light chain variable region comprises a sequence that is at least 90% identical to SEQ ID NO:74;
(d) the heavy chain variable region comprises a sequence that is at least 90% identical to SEQ ID NO: 75, and wherein the light chain variable region comprises a sequence that is at least 90% identical to SEQ ID NO:76;
(e) the heavy chain variable region comprises a sequence that is at least 90% identical to SEQ ID NO: 81, and wherein the light chain variable region comprises a sequence that is at least 90% identical to SEQ ID NO:82;
(f) the heavy chain variable region comprises a sequence that is at least 90% identical to SEQ ID NO: 79, and wherein the light chain variable region comprises a sequence that is at least 90% identical to SEQ ID NO: 80;
(g) the heavy chain variable region comprises a sequence that is at least 90% identical to SEQ ID NO: 83, and wherein the light chain variable region comprises a sequence that is at least 90% identical to SEQ ID NO:84;
(h) the heavy chain variable region comprises a sequence that is at least 90% identical to SEQ ID NO: 85, and wherein the light chain variable region comprises a sequence that is at least 90% identical to SEQ ID NO:86;
(i) the heavy chain variable region comprises a sequence that is at least 90% identical to SEQ ID NO: 87, and wherein the light chain variable region comprises a sequence that is at least 90% identical to SEQ ID NO:88;
(j) the heavy chain variable region comprises a sequence that is at least 90% identical to SEQ ID NO: 91, and wherein the light chain variable region comprises a sequence that is at least 90% identical to SEQ ID NO:92;
(k) the heavy chain variable region comprises a sequence that is at least 90% identical to SEQ ID NO: 103, and wherein the light chain variable region comprises a sequence that is at least 90% identical to SEQ ID NO:104;
(l) the heavy chain variable region comprises a sequence that is at least 90% identical to SEQ ID NO: 97, and wherein the light chain variable region comprises a sequence that is at least 90% identical to SEQ ID NO:98;
(m) the heavy chain variable region comprises a sequence that is at least 90% identical to SEQ ID NO: 93, and wherein the light chain variable region comprises a sequence that is at least 90% identical to SEQ ID NO:94; or
(n) the heavy chain variable region comprises a sequence that is at least 90% identical to SEQ ID NO: 95, and wherein the light chain variable region comprises a sequence that is at least 90% identical to SEQ ID NO:96.

3. The antibody or antigen-binding fragment thereof according to claim 2, wherein:
(a) the heavy chain variable region comprises SEQ ID NO:101 and the light chain variable region comprises SEQ ID NO:102;
(b) the heavy chain variable region comprises SEQ ID NO:69 and the light chain variable region comprises SEQ ID NO:70;
(c) the heavy chain variable region comprises SEQ ID NO:73 and the light chain variable region comprises SEQ ID NO:74;
(d) the heavy chain variable region comprises SEQ ID NO:75 and the light chain variable region comprises SEQ ID NO:76;
(e) the heavy chain variable region comprises SEQ ID NO:81 and the light chain variable region comprises SEQ ID NO:82;
(f) the heavy chain variable region comprises SEQ ID NO:79 and the light chain variable region comprises SEQ ID NO:80;
(g) the heavy chain variable region comprises SEQ ID NO:83 and the light chain variable region comprises SEQ ID NO:84;
(h) the heavy chain variable region comprises SEQ ID NO:85 and the light chain variable region comprises SEQ ID NO:86;

(i) the heavy chain variable region comprises SEQ ID NO:87 and the light chain variable region comprises SEQ ID NO:88;
(j) the heavy chain variable region comprises SEQ ID NO:91 and the light chain variable region comprises SEQ ID NO:92;
(k) the heavy chain variable region comprises SEQ ID NO:103 and the light chain variable region comprises SEQ ID NO:104;
(l) the heavy chain variable region comprises SEQ ID NO:97 and the light chain variable region comprises SEQ ID NO:98;
(m) the heavy chain variable region comprises SEQ ID NO:93 and the light chain variable region comprises SEQ ID NO:94; or
(n) the heavy chain variable region comprises SEQ ID NO:95 and the light chain variable region comprises SEQ ID NO:96.

4. The antibody or antigen-binding fragment thereof of claim 1, wherein the antibody or antigen-binding fragment thereof is a multispecific or a bispecific antibody, or an antigen-binding fragment thereof.

5. The antibody or antigen-binding fragment thereof of claim 1, wherein the antibody or antigen-binding fragment thereof is an scFv, Fv, Fab', Fab,F(ab') 2, or a diabody.

6. The antibody or antigen-binding fragment thereof of claim 1, wherein the antibody or antigen-binding fragment thereof is an IgG1, IgG2a, or IgG2b isotype.

7. The antibody or antigen-binding fragment thereof of claim 1, wherein the antibody or antigen-binding fragment thereof is conjugated to one or more of a cytotoxin, a fluorescent label, and an imaging agent.

8. A pharmaceutical composition comprising the antibody or antigen-binding fragment thereof of claim 1, and a pharmaceutically acceptable excipient.

9. A method of reducing replication of JCV in a subject in need thereof, the method comprising administering to the subject an effective amount of the antibody or antigen-binding fragment thereof of claim 1.

10. A method of reducing the occurrence, duration, or severity of immune reconstitution inflammatory syndrome (IRIS) in a subject in need thereof, the method comprising administering to the subject an effective amount of the antibody or antigen-binding fragment thereof of claim 1.

11. A method of treating progressive multifocal leukoencephalopathy (PML) in a subject in need thereof, the method comprising administering to the subject an effective amount of the antibody or antigen-binding fragment thereof of claim 1.

12. The method according to claim 11, wherein the subject has previously received or is currently receiving:
(a) treatment with an anti-retroviral agent; or
(b) treatment with an immunosuppressing agent or an immunomodulatory agent.

13. The method according to claim 11, wherein the central nervous system of the subject is infected with JCV.

14. The method according to claim 11, wherein the subject has an immune deficiency.

15. The method according to claim 14, wherein the immune deficiency is hereditary.

16. The method according to claim 15, wherein the subject has a condition selected from the group consisting of adenosine deaminase deficiency, CD40 ligand deficiency, combined immune deficiency, common variable immune deficiency, DOCK8 (dedicator of cytokinesis 8 protein) deficiency, gamma heavy chain disease, hyper-IgM syndrome, immunodeficiency-centromeric instability-facial dysmorphism syndrome, purine nucleoside phosphorylase deficiency, severe combined immune deficiency, signal transducer and activator of transcription 1 gain-of-function immune deficiency, Wiskott-Aldrich syndrome, X-linked agammaglobulinaemia, idiopathic CD4$^+$ lymphopenia, and Sarcoidosis sarcoidosis.

17. The method according to claim 14, wherein the immune deficiency is acquired.

18. The method according to claim 17, wherein the subject is infected with a human immunodeficiency virus (HIV) or has acquired immunodeficiency syndrome (AIDS).

19. The method according to claim 11, wherein the subject has cancer.

20. The method according to claim 19, wherein the cancer is selected from the group consisting of glioma, glioblastoma, thymoma, mesothelioma, sarcoma, chromophobe renal cell carcinoma, adenoid cystic carcinoma, acute myeloid leukemia, melanoma, papillary renal cell carcinoma, clear cell renal cell carcinoma, diffuse large B-cell lymphoma, pheochromocytoma, paraganglioma, pancreatic cancer, thyroid cancer, lung cancer, colorectal cancer, squamous cancer, breast cancer, prostate cancer, bladder cancer, gastric cancer, testicular germ cell cancer, ovarian cancer, head and neck cancer, uterine cancer, cervical cancer, and liver cancer.

21. The method according to claim 11, wherein the subject has an autoimmune disease.

22. The method according to claim 21, wherein the autoimmune disease is selected from the group consisting of rheumatoid arthritis, psoriatic arthritis, psoriasis, juvenile idiopathic arthritis, inflammatory bowel disease, Crohn's disease, ankylosing spondylitis, and multiple sclerosis.

23. The method according to claim 22, wherein the autoimmune disease is multiple sclerosis or Crohn's disease.

24. The method according to claim 11, wherein the subject has received a transplant.

25. The method according to claim 24, wherein the transplant is a hematopoietic stem cell transplant, a bone marrow transplant, or an organ transplant.

26. The method according to claim 24, wherein the administration of the antibody or antigen-binding fragment thereof occurs:
(a) before administering an immunosuppressing agent or an immunomodulatory agent to the subject; or
(b) after administration of the immunosuppressing agent or immunomodulatory agent.

27. The method according to claim 26, wherein the immunosuppressing agent or an immunomodulatory agent is a modulator of TNF-α, BLys, α4-integrin, CTLA-4, CD11a, CD20, CD30, CD52, sphingosine 1-phosphate receptor, inosine monophosphate dehydrogenase, janus kinase, or dihydroorotate dehydrogenase.

28. The method according to claim 26, wherein the immunosuppressing agent or an immunomodulatory agent is selected from the group consisting of Natalizumab, efalizumab, belimumab, rituximab, fingolimod, dimethylfumarate, alemtuzumab, adalimumab, etanercept, ofatumumab, mycophenolate mofetil, betalacept, brentuximab, fludarabine, ruxolitinib, leflunomide, and infliximab.

* * * * *

SEQUENCE LISTING

<160> NUMBER OF SEQ ID NOS: 141

<210> SEQ ID NO 1
<211> LENGTH: 8
<212> TYPE: PRT
<213> ORGANISM: Artificial Sequence
<220> FEATURE:
<223> OTHER INFORMATION: synthetic peptide

<400> SEQUENCE: 1

Gly Phe Thr Phe Ser Asp Leu Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic peptide

<400> SEQUENCE: 2

Glu Ile Thr Phe Ser Asp Tyr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Gly Phe Thr Phe Ser Asp His Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Gly Phe Thr Phe Ser Asp Phe Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic peptide

<400> SEQUENCE: 5

Gly Ile Thr Phe Ser Asp Leu Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic peptide

<400> SEQUENCE: 6

Gly Gly Ser Ile Ser Ser Asn Tyr
1               5

```
<210> SEQ ID NO 7
<211> LENGTH: 8
<212> TYPE: PRT
<213> ORGANISM: Artificial Sequence
<220> FEATURE:
<223> OTHER INFORMATION: synthetic peptide

<400> SEQUENCE: 7

Gly Tyr Thr Phe Thr Phe Tyr Asp
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic peptide

<400> SEQUENCE: 8

Gly Tyr Thr Phe Thr Asn Tyr Asp
1               5

<210> SEQ ID NO 9
<211> LENGTH: 8
<212> TYPE: PRT
<213> ORGANISM: Artificial Sequence
<220> FEATURE:
<223> OTHER INFORMATION: synthetic peptide

<400> SEQUENCE: 9

Gly Gly Ser Phe Ser Gly Tyr Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: synthetic peptide

<400> SEQUENCE: 10

Gly Gly Ser Phe Ser Ser Tyr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic peptide

<400> SEQUENCE: 11

Gly Phe Thr Leu Ser Thr Tyr Ala
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic peptide

<400> SEQUENCE: 12

Ile Ser Thr Ser Gly Arg Thr Ile
1               5
```

```
<210> SEQ ID NO 13
<211> LENGTH: 8
<212> TYPE: PRT
<213> ORGANISM: Artificial Sequence
<220> FEATURE:
<223> OTHER INFORMATION: synthetic peptide

<400> SEQUENCE: 13

Ile Ser Thr Ser Gly Ser Thr Ile
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic peptide

<400> SEQUENCE: 14

Ile Ser Thr Gly Gly Arg Thr Ile
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic peptide

<400> SEQUENCE: 15

Ile Ser Phe Ser Gly Arg Ala Ile
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic peptide

<400> SEQUENCE: 16

Ile Tyr Tyr Ser Gly Ser Thr
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic peptide

<400> SEQUENCE: 17

Met Asn Pro Asn Ser Gly Asn Thr
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic peptide

<400> SEQUENCE: 18

Val Asn Pro Asn Ser Gly Asn Ser
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: synthetic peptide

<400> SEQUENCE: 19

Thr Asn Pro Asn Ser Gly Asn Ser
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Ile Asn His Gly Gly Ser Thr
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic peptide

<400> SEQUENCE: 21

Ile Asn His Ser Gly Ser Thr
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic peptide

<400> SEQUENCE: 22

Ile Ser Gly Thr Gly Leu Ser Thr
1               5

<210> SEQ ID NO 23
<211> LENGTH: 12
<212> TYPE: PRT
<213> ORGANISM: Artificial Sequence
<220> FEATURE:
<223> OTHER INFORMATION: synthetic peptide

<400> SEQUENCE: 23

Ala Gly Asp Tyr Tyr Asp Asn Ser Gly Trp Asp Tyr
1               5                   10

<210> SEQ ID NO 24
<211> LENGTH: 12
<212> TYPE: PRT
<213> ORGANISM: Artificial Sequence
<220> FEATURE:
<223> OTHER INFORMATION: synthetic peptide

<400> SEQUENCE: 24

Ala Ser Asp Phe Tyr Asp Asn Ser Gly Trp Glu Tyr
1               5                   10

<210> SEQ ID NO 25
```

```
<211> LENGTH: 12
<212> TYPE: PRT
<213> ORGANISM: Artificial Sequence
<220> FEATURE:
<223> OTHER INFORMATION: synthetic peptide

<400> SEQUENCE: 25

Ala Ser Asp Tyr Tyr Asp Asn Ser Gly Trp Tyr Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: synthetic peptide

<400> SEQUENCE: 26

Ala Ser Asp Tyr Tyr Asp Asn Val Gly Trp Asn Tyr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic peptide

<400> SEQUENCE: 27

Ala Ser Asp Tyr Tyr Asp Asn Ser Gly Trp Asn Tyr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: synthetic peptide

<400> SEQUENCE: 28

Ala Ser Asp Tyr Tyr Asp Asn Val Gly Trp Asp Tyr
1               5                   10

<210> SEQ ID NO 29
<211> LENGTH: 19
<212> TYPE: PRT
<213> ORGANISM: Artificial Sequence
<220> FEATURE:
<223> OTHER INFORMATION: synthetic peptide

<400> SEQUENCE: 29

Ala Arg Arg Gly Phe Glu Gln Gln Leu Ser Tyr Tyr Tyr Tyr Gly
1               5                   10                  15

Leu Asp Val

<210> SEQ ID NO 30
<211> LENGTH: 19
<212> TYPE: PRT
<213> ORGANISM: Artificial Sequence
<220> FEATURE:
<223> OTHER INFORMATION: synthetic peptide

<400> SEQUENCE: 30

Ala Arg Arg Gly Phe Glu Gln Gln Leu Ser Tyr Tyr Tyr Tyr Gly
1               5                   10                  15

Met Asp Val
```

<210> SEQ ID NO 31
<211> LENGTH: 13
<212> TYPE: PRT
<213> ORGANISM: Artificial Sequence
<220> FEATURE:
<223> OTHER INFORMATION: synthetic peptide

<400> SEQUENCE: 31

Ala Arg Lys Ile Trp Val Gly His Thr Thr Phe Asp Arg
1               5                   10

<210> SEQ ID NO 32
<211> LENGTH: 13
<212> TYPE: PRT
<213> ORGANISM: Artificial Sequence
<220> FEATURE:
<223> OTHER INFORMATION: synthetic peptide

<400> SEQUENCE: 32

Ala Arg Lys Ile Trp Val Gly Thr Thr Ile Phe Asp Tyr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic peptide

<400> SEQUENCE: 33

Ala Arg Gly Trp Gly Gly Gln Val Ala His Trp Phe Asp Pro
1               5                   10

<210> SEQ ID NO 34
<211> LENGTH: 13
<212> TYPE: PRT
<213> ORGANISM: Artificial Sequence
<220> FEATURE:
<223> OTHER INFORMATION: synthetic peptide

<400> SEQUENCE: 34

Ala Arg Trp Gly Ile Ala Ala Asp Tyr Gly Met Asp Val
1               5                   10

<210> SEQ ID NO 35
<211> LENGTH: 15
<212> TYPE: PRT
<213> ORGANISM: Artificial Sequence
<220> FEATURE:
<223> OTHER INFORMATION: synthetic peptide

<400> SEQUENCE: 35

Ala Lys Gly Leu Glu Leu Phe Tyr Phe Tyr Tyr Gly Met Asp Val
1               5                   10                  15

<210> SEQ ID NO 36
<211> LENGTH: 11
<212> TYPE: PRT
<213> ORGANISM: Artificial Sequence
<220> FEATURE:
<223> OTHER INFORMATION: synthetic peptide

<400> SEQUENCE: 36

Gln Ser Leu Val Tyr Ser Asp Gly Asn Thr Tyr
1               5                   10

```
<210> SEQ ID NO 37
<211> LENGTH: 11
<212> TYPE: PRT
<213> ORGANISM: Artificial Sequence
<220> FEATURE:
<223> OTHER INFORMATION: synthetic peptide

<400> SEQUENCE: 37

Gln Ser Leu Ile Tyr Ser Asp Gly Asn Thr Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: synthetic peptide

<400> SEQUENCE: 38

Gln Ser Leu Leu Tyr Ser Asp Gly Asn Thr Tyr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: synthetic peptide

<400> SEQUENCE: 39

Gln Ser Val Leu Tyr Ser Ser Asn Asn Lys Asn Tyr
1               5                   10

<210> SEQ ID NO 40
<211> LENGTH: 6
<212> TYPE: PRT
<213> ORGANISM: Artificial Sequence
<220> FEATURE:
<223> OTHER INFORMATION: synthetic peptide

<400> SEQUENCE: 40

Gln Ser Ile Ser Gly Tyr
1               5

<210> SEQ ID NO 41
<211> LENGTH: 6
<212> TYPE: PRT
<213> ORGANISM: Artificial Sequence
<220> FEATURE:
<223> OTHER INFORMATION: synthetic peptide

<400> SEQUENCE: 41

Gln Ser Ile Tyr Arg Phe
1               5

<210> SEQ ID NO 42
<211> LENGTH: 12
<212> TYPE: PRT
<213> ORGANISM: Artificial Sequence
<220> FEATURE:
<223> OTHER INFORMATION: synthetic peptide

<400> SEQUENCE: 42

Gln Ser Val Leu Phe Ser Ser Asn Asn Gln Asn Tyr
1               5                   10
```

```
<210> SEQ ID NO 43
<211> LENGTH: 7
<212> TYPE: PRT
<213> ORGANISM: Artificial Sequence
<220> FEATURE:
<223> OTHER INFORMATION: synthetic peptide

<400> SEQUENCE: 43

Gln Ser Val Ser Ser Ser Tyr
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic peptide

<400> SEQUENCE: 44

Gln Ser Val Ser Ser Thr Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: synthetic peptide

<400> SEQUENCE: 45

Met Gln Gly Thr His Trp Pro Arg Thr
1               5

<210> SEQ ID NO 46
<211> LENGTH: 9
<212> TYPE: PRT
<213> ORGANISM: Artificial Sequence
<220> FEATURE:
<223> OTHER INFORMATION: synthetic peptide

<400> SEQUENCE: 46

Met Gln Gly Ser His Trp Pro Arg Thr
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic peptide

<400> SEQUENCE: 47

Met Gln Gly Ala His Trp Pro Arg Thr
1               5

<210> SEQ ID NO 48
<211> LENGTH: 9
<212> TYPE: PRT
<213> ORGANISM: Artificial Sequence
<220> FEATURE:
<223> OTHER INFORMATION: synthetic peptide

<400> SEQUENCE: 48

Gln Gln Tyr Tyr Thr Phe Pro Trp Thr
1               5

<210> SEQ ID NO 49
```

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 49

Gln Gln Tyr Tyr Ser Thr Pro Trp Thr
1               5

<210> SEQ ID NO 50
<211> LENGTH: 9
<212> TYPE: PRT
<213> ORGANISM: Artificial Sequence
<220> FEATURE:
<223> OTHER INFORMATION: synthetic peptide

<400> SEQUENCE: 50

Gln Gln Thr Tyr Asn Ile Pro Phe Thr
1               5

<210> SEQ ID NO 51
<211> LENGTH: 9
<212> TYPE: PRT
<213> ORGANISM: Artificial Sequence
<220> FEATURE:
<223> OTHER INFORMATION: synthetic peptide

<400> SEQUENCE: 51

Gln Gln Ser Asp Gly Pro Pro Leu Thr
1               5

<210> SEQ ID NO 52
<211> LENGTH: 9
<212> TYPE: PRT
<213> ORGANISM: Artificial Sequence
<220> FEATURE:
<223> OTHER INFORMATION: synthetic peptide

<400> SEQUENCE: 52

Gln Gln Ser Asp Ser Pro Pro Leu Thr
1               5

<210> SEQ ID NO 53
<211> LENGTH: 9
<212> TYPE: PRT
<213> ORGANISM: Artificial Sequence
<220> FEATURE:
<223> OTHER INFORMATION: synthetic peptide

<400> SEQUENCE: 53

Gln Gln Tyr Tyr Ser Leu Pro Tyr Thr
1               5

<210> SEQ ID NO 54
<211> LENGTH: 9
<212> TYPE: PRT
<213> ORGANISM: Artificial Sequence
<220> FEATURE:
<223> OTHER INFORMATION: synthetic peptide

<400> SEQUENCE: 54

Gln Gln Tyr Gly Thr Ser Pro Trp Thr
1               5

<210> SEQ ID NO 55
<211> LENGTH: 8
```

```
<212> TYPE: PRT
<213> ORGANISM: Artificial Sequence
<220> FEATURE:
<223> OTHER INFORMATION: synthetic peptide

<400> SEQUENCE: 55

Gln Gln Tyr Gly Arg Ser Leu Ile
1               5

<210> SEQ ID NO 56
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X = G or E
<220> FEATURE:
<221> NAME/KEY: MISC_FEATURE
<222> LOCATION: (2)..(2)
<223> OTHER INFORMATION: X = F or I
<220> FEATURE:
<221> NAME/KEY: MISC_FEATURE
<222> LOCATION: (7)..(7)
<223> OTHER INFORMATION: X = H, L, Y, or F

<400> SEQUENCE: 56

Xaa Xaa Thr Phe Ser Asp Xaa Tyr
1               5

<210> SEQ ID NO 57
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: X = F or N

<400> SEQUENCE: 57

Gly Tyr Thr Phe Thr Xaa Tyr Asp
1               5

<210> SEQ ID NO 58
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: X = T or F
<220> FEATURE:
<221> NAME/KEY: MISC_FEATURE
<222> LOCATION: (4)..(4)
<223> OTHER INFORMATION: X = S or G
<220> FEATURE:
<221> NAME/KEY: MISC_FEATURE
<222> LOCATION: (6)..(6)
<223> OTHER INFORMATION: X = R or S
<220> FEATURE:
<221> NAME/KEY: MISC_FEATURE
<222> LOCATION: (7)..(7)
<223> OTHER INFORMATION: X = T or A

<400> SEQUENCE: 58

Ile Ser Xaa Xaa Gly Xaa Xaa Ile
```

-continued

```
1               5

<210> SEQ ID NO 59
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X = M or V
<220> FEATURE:
<221> NAME/KEY: MISC_FEATURE
<222> LOCATION: (8)..(8)
<223> OTHER INFORMATION: X = T or S

<400> SEQUENCE: 59

Xaa Asn Pro Asn Ser Gly Asn Xaa
1               5

<210> SEQ ID NO 60
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X = M or V or T
<220> FEATURE:
<221> NAME/KEY: MISC_FEATURE
<222> LOCATION: (8)..(8)
<223> OTHER INFORMATION: X = T or S

<400> SEQUENCE: 60

Xaa Asn Pro Asn Ser Gly Asn Xaa
1               5

<210> SEQ ID NO 61
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: X = G or S
<220> FEATURE:
<221> NAME/KEY: MISC_FEATURE
<222> LOCATION: (4)..(4)
<223> OTHER INFORMATION: X = Y or F
<220> FEATURE:
<221> NAME/KEY: MISC_FEATURE
<222> LOCATION: (8)..(8)
<223> OTHER INFORMATION: X = S or V
<220> FEATURE:
<221> NAME/KEY: MISC_FEATURE
<222> LOCATION: (11)..(11)
<223> OTHER INFORMATION: X = D, E, Y, or N

<400> SEQUENCE: 61

Ala Xaa Asp Xaa Tyr Asp Asn Xaa Gly Trp Xaa Tyr
1               5                   10

<210> SEQ ID NO 62
<211> LENGTH: 19
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MISC_FEATURE
<222> LOCATION: (17)..(17)
<223> OTHER INFORMATION: X = L or M

<400> SEQUENCE: 62

Ala Arg Arg Gly Phe Glu Gln Gln Leu Ser Tyr Tyr Tyr Tyr Tyr Gly
1               5                   10                  15

Xaa Asp Val

<210> SEQ ID NO 63
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: X = H or T
<220> FEATURE:
<221> NAME/KEY: MISC_FEATURE
<222> LOCATION: (10)..(10)
<223> OTHER INFORMATION: X = T or I
<220> FEATURE:
<221> NAME/KEY: MISC_FEATURE
<222> LOCATION: (13)..(13)
<223> OTHER INFORMATION: X = R or Y

<400> SEQUENCE: 63

Ala Arg Lys Ile Trp Val Gly Xaa Thr Xaa Phe Asp Xaa
1               5                   10

<210> SEQ ID NO 64
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: X = V or I

<400> SEQUENCE: 64

Gln Ser Leu Xaa Tyr Ser Asp Gly Asn Thr Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: X = V or I or L

<400> SEQUENCE: 65

Gln Ser Leu Xaa Tyr Ser Asp Gly Asn Thr Tyr
1               5                   10

<210> SEQ ID NO 66
<211> LENGTH: 9
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MISC_FEATURE
<222> LOCATION: (4)..(4)
<223> OTHER INFORMATION: X = T or S

<400> SEQUENCE: 66

Met Gln Gly Xaa His Trp Pro Arg Thr
1               5

<210> SEQ ID NO 67
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: X = T or S or A

<400> SEQUENCE: 67

Met Gln Gly Xaa His Trp Pro Arg Thr
1               5

<210> SEQ ID NO 68
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: X = T or S
<220> FEATURE:
<221> NAME/KEY: MISC_FEATURE
<222> LOCATION: (6)..(6)
<223> OTHER INFORMATION: X = T or F

<400> SEQUENCE: 68

Gln Gln Tyr Tyr Xaa Xaa Pro Trp Thr
1               5

<210> SEQ ID NO 69
<211> LENGTH: 119
<212> TYPE: PRT
<213> ORGANISM: Artificial Sequence
<220> FEATURE:
<223> OTHER INFORMATION: synthetic peptide

<400> SEQUENCE: 69

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Leu
            20                  25                  30

Tyr Met Ser Trp Ile Arg Gln Ala Pro Gly Lys Gly Leu Glu Trp Val
        35                  40                  45

Ser Tyr Ile Ser Thr Ser Gly Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Asp Tyr Tyr Asp Asn Ser Gly Trp Asp Tyr Trp Gly Arg Gly
            100                 105                 110
```

Thr Leu Val Thr Val Ser Ser
          115

<210> SEQ ID NO 70
<211> LENGTH: 112
<212> TYPE: PRT
<213> ORGANISM: Artificial Sequence
<220> FEATURE:
<223> OTHER INFORMATION: synthetic peptide

<400> SEQUENCE: 70

Asp Val Val Met Thr Gln Ser Pro Leu Ser Leu Pro Val Thr Leu Gly
1               5                   10                  15

Gln Pro Ala Ser Ile Ser Cys Arg Ser Gly Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asp Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys Val Glu Ile Lys
            100                 105                 110

<210> SEQ ID NO 71
<211> LENGTH: 119
<212> TYPE: PRT
<213> ORGANISM: Artificial Sequence
<220> FEATURE:
<223> OTHER INFORMATION: synthetic peptide

<400> SEQUENCE: 71

Gln Val Gln Leu Val Glu Ser Gly Gly Gly Leu Val Lys Pro Gly Gly
1               5                   10                  15

Ser Leu Arg Leu Ser Cys Ala Ala Ser Glu Ile Thr Phe Ser Asp Tyr
            20                  25                  30

Tyr Met Ser Trp Ile Arg Gln Ala Pro Gly Lys Gly Leu Glu Trp Ile
        35                  40                  45

Ser Tyr Ile Ser Thr Ser Gly Arg Thr Ile Tyr Phe Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Thr Ala Val Tyr Tyr Cys
                85                  90                  95

Ala Ser Asp Phe Tyr Asp Asn Ser Gly Trp Glu Tyr Trp Gly Gln Gly
            100                 105                 110

Thr Leu Val Thr Val Ser Ser
          115

<210> SEQ ID NO 72
<211> LENGTH: 112
<212> TYPE: PRT
<213> ORGANISM: Artificial Sequence
<220> FEATURE:
<223> OTHER INFORMATION: synthetic peptide

<400> SEQUENCE: 72

Asp Val Val Met Thr Gln Ser Pro Leu Ser Leu Ser Val Thr Leu Gly

```
1               5                   10                  15
Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Leu Ile Tyr Lys Val Ser Asp Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gly
                85                  90                  95

Thr His Trp Pro Arg Thr Phe Gly Gln Gly Thr Lys Val Glu Ile Lys
                100                 105                 110
```

<210> SEQ ID NO 73
<211> LENGTH: 119
<212> TYPE: PRT
<213> ORGANISM: Artificial Sequence
<220> FEATURE:
<223> OTHER INFORMATION: synthetic peptide

<400> SEQUENCE: 73

```
Gln Val Gln Leu Val Glu Ser Gly Gly Gly Leu Val Lys Pro Gly Gly
1               5                   10                  15

Ser Leu Arg Leu Ser Cys Ala Gly Ser Gly Phe Thr Phe Ser Asp His
                20                  25                  30

Tyr Met Ser Trp Ile Arg Gln Ala Pro Gly Lys Gly Leu Glu Trp Val
            35                  40                  45

Ser Tyr Ile Ser Thr Ser Gly Arg Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Asp Tyr Tyr Asp Asn Ser Gly Trp Tyr Tyr Trp Gly Gln Gly
                100                 105                 110

Thr Leu Val Thr Val Ser Ser
        115
```

<210> SEQ ID NO 74
<211> LENGTH: 112
<212> TYPE: PRT
<213> ORGANISM: Artificial Sequence
<220> FEATURE:
<223> OTHER INFORMATION: synthetic peptide

<400> SEQUENCE: 74

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asp Arg Asp Ser Gly Val Pro
        50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Gly
                85                  90                  95

Thr His Trp Pro Arg Thr Phe Gly Gln Gly Thr Val Glu Ile Lys
            100                 105                 110
```

<210> SEQ ID NO 75
<211> LENGTH: 119
<212> TYPE: PRT
<213> ORGANISM: Artificial Sequence
<220> FEATURE:
<223> OTHER INFORMATION: synthetic peptide

<400> SEQUENCE: 75

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
                20                  25                  30

Tyr Met Ser Trp Ile Arg Gln Ala Pro Gly Lys Gly Leu Glu Trp Val
            35                  40                  45

Ser Tyr Ile Ser Thr Ser Gly Arg Thr Ile Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Ser Asp Tyr Tyr Asp Asn Val Gly Trp Asn Tyr Trp Gly Gln Gly
            100                 105                 110

Ala Leu Val Thr Val Ser Ser
        115
```

<210> SEQ ID NO 76
<211> LENGTH: 112
<212> TYPE: PRT
<213> ORGANISM: Artificial Sequence
<220> FEATURE:
<223> OTHER INFORMATION: synthetic peptide

<400> SEQUENCE: 76

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asp Arg Asp Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Arg Thr Phe Gly Gln Gly Thr Lys Val Glu Ile Lys
            100                 105                 110
```

<210> SEQ ID NO 77
<211> LENGTH: 119
<212> TYPE: PRT
<213> ORGANISM: Artificial Sequence
<220> FEATURE:
<223> OTHER INFORMATION: synthetic peptide

<400> SEQUENCE: 77

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Ser Thr Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Asp Tyr Tyr Asp Asn Ser Gly Trp Asn Tyr Trp Gly Gln Gly
            100                 105                 110

Thr Leu Val Thr Val Ser Ser
            115

<210> SEQ ID NO 78
<211> LENGTH: 112
<212> TYPE: PRT
<213> ORGANISM: Artificial Sequence
<220> FEATURE:
<223> OTHER INFORMATION: synthetic peptide

<400> SEQUENCE: 78

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asp Arg Asp Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Ser His Trp Pro Arg Thr Phe Gly Gln Gly Thr Lys Val Glu Ile Lys
            100                 105                 110

<210> SEQ ID NO 79
<211> LENGTH: 119
<212> TYPE: PRT
<213> ORGANISM: Artificial Sequence
<220> FEATURE:
<223> OTHER INFORMATION: synthetic peptide

<400> SEQUENCE: 79

Gln Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Ser Thr Gly Gly Arg Thr Ile Tyr Ala Asp Ser Val
    50                  55                  60

-continued

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Asp Tyr Tyr Asp Asn Val Gly Trp Asp Tyr Trp Gly Gln Gly
            100                 105                 110

Thr Leu Val Thr Val Ser Ser
            115

<210> SEQ ID NO 80
<211> LENGTH: 112
<212> TYPE: PRT
<213> ORGANISM: Artificial Sequence
<220> FEATURE:
<223> OTHER INFORMATION: synthetic peptide

<400> SEQUENCE: 80

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asp Arg Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys Val Glu Ile Lys
            100                 105                 110

<210> SEQ ID NO 81
<211> LENGTH: 119
<212> TYPE: PRT
<213> ORGANISM: Artificial Sequence
<220> FEATURE:
<223> OTHER INFORMATION: synthetic peptide

<400> SEQUENCE: 81

Gln Val Gln Leu Val Glu Ser Gly Gly Gly Leu Val Lys Pro Gly Gly
1               5                   10                  15

Ser Leu Arg Leu Ser Cys Ala Gly Ser Gly Phe Thr Phe Ser Asp His
                20                  25                  30

Tyr Met Ser Trp Ile Arg Gln Ala Pro Gly Lys Gly Leu Glu Trp Val
            35                  40                  45

Ser Tyr Ile Ser Thr Ser Gly Arg Thr Ile Phe Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Ser Asp Tyr Tyr Asp Asn Val Gly Trp Tyr Trp Gly Gln Gly
            100                 105                 110

Ala Leu Val Ile Val Ser Ser
            115

<210> SEQ ID NO 82

```
<211> LENGTH: 112
<212> TYPE: PRT
<213> ORGANISM: Artificial Sequence
<220> FEATURE:
<223> OTHER INFORMATION: synthetic peptide

<400> SEQUENCE: 82

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asp Arg Asp Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Arg Thr Phe Gly Gln Gly Thr Lys Val Glu Ile Lys
            100                 105                 110

<210> SEQ ID NO 83
<211> LENGTH: 119
<212> TYPE: PRT
<213> ORGANISM: Artificial Sequence
<220> FEATURE:
<223> OTHER INFORMATION: synthetic peptide

<400> SEQUENCE: 83

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Tyr Met Ser Trp Ile Arg Gln Ala Pro Gly Met Gly Leu Glu Trp Val
        35                  40                  45

Ser Tyr Ile Ser Phe Ser Gly Arg Ala Ile Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Ser Ala Glu Asp Thr Ala Val Tyr Tyr Cys
                85                  90                  95

Ala Ser Asp Tyr Tyr Asp Asn Val Gly Trp Asp Tyr Trp Gly Pro Gly
            100                 105                 110

Thr Leu Val Thr Val Ser Ser
        115

<210> SEQ ID NO 84
<211> LENGTH: 112
<212> TYPE: PRT
<213> ORGANISM: Artificial Sequence
<220> FEATURE:
<223> OTHER INFORMATION: synthetic peptide

<400> SEQUENCE: 84

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30
```

```
Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
65                   70                  75                  80

Ser Arg Val Glu Ala Glu Asp Ile Gly Val Tyr Tyr Cys Met Gln Gly
                85                  90                  95

Thr His Trp Pro Arg Thr Phe Gly Gln Gly Thr Lys Val Glu Ile Lys
            100                 105                 110
```

<210> SEQ ID NO 85
<211> LENGTH: 125
<212> TYPE: PRT
<213> ORGANISM: Artificial Sequence
<220> FEATURE:
<223> OTHER INFORMATION: synthetic peptide

<400> SEQUENCE: 85

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Tyr Trp Asn Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Phe Glu Gln Gln Leu Ser Tyr Tyr Tyr Tyr Gly Leu
            100                 105                 110

Asp Val Trp Gly Gln Gly Thr Thr Val Thr Val Ser Ser
        115                 120                 125
```

<210> SEQ ID NO 86
<211> LENGTH: 113
<212> TYPE: PRT
<213> ORGANISM: Artificial Sequence
<220> FEATURE:
<223> OTHER INFORMATION: synthetic peptide

<400> SEQUENCE: 86

```
Asp Ile Val Met Thr Gln Ser Pro Asp Ser Leu Ala Val Ser Leu Gly
1               5                   10                  15

Glu Arg Ala Thr Val Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asp Tyr Tyr Cys Gln Gln
                85                  90                  95

Tyr Tyr Thr Phe Pro Trp Thr Phe Gly Gln Gly Thr Lys Val Glu Ile
            100                 105                 110
```

Lys

<210> SEQ ID NO 87
<211> LENGTH: 125
<212> TYPE: PRT
<213> ORGANISM: Artificial Sequence
<220> FEATURE:
<223> OTHER INFORMATION: synthetic peptide

<400> SEQUENCE: 87

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Phe Glu Gln Gln Leu Ser Tyr Tyr Tyr Tyr Gly Met
            100                 105                 110

Asp Val Trp Gly Gln Gly Thr Thr Val Thr Val Ser Ser
        115                 120                 125
```

<210> SEQ ID NO 88
<211> LENGTH: 113
<212> TYPE: PRT
<213> ORGANISM: Artificial Sequence
<220> FEATURE:
<223> OTHER INFORMATION: synthetic peptide

<400> SEQUENCE: 88

```
Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110
```

Lys

<210> SEQ ID NO 89
<211> LENGTH: 120
<212> TYPE: PRT
<213> ORGANISM: Artificial Sequence
<220> FEATURE:
<223> OTHER INFORMATION: synthetic peptide

<400> SEQUENCE: 89

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Phe Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Asn Phe
50                  55                  60

Gln Gly Arg Val Thr Met Thr Arg Asn Thr Ser Ile Asn Thr Ala Tyr
65                  70                  75                  80

Leu Glu Leu Ser Ser Leu Arg Ser Glu Asp Thr Ala Val Tyr Tyr Cys
                85                  90                  95

Ala Arg Lys Ile Trp Val Gly His Thr Thr Phe Asp Arg Trp Gly Gln
            100                 105                 110

Gly Thr Leu Val Thr Val Ser Ser
        115                 120

<210> SEQ ID NO 90
<211> LENGTH: 107
<212> TYPE: PRT
<213> ORGANISM: Artificial Sequence
<220> FEATURE:
<223> OTHER INFORMATION: synthetic peptide

<400> SEQUENCE: 90

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Asn Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Arg
65                  70                  75                  80

Glu Asp Phe Ala Pro Tyr Tyr Cys Gln Gln Thr Tyr Asn Ile Pro Phe
                85                  90                  95

Thr Phe Gly Gly Gly Thr Lys Val Glu Ile Lys
            100                 105

<210> SEQ ID NO 91
<211> LENGTH: 120
<212> TYPE: PRT
<213> ORGANISM: Artificial Sequence
<220> FEATURE:
<223> OTHER INFORMATION: synthetic peptide

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Thr Gly Gln Gly Leu Glu Trp Met
        35                  40                  45

Gly Trp Val Asn Pro Asn Ser Gly Asn Ser Gly Tyr Ala Gln Lys Phe
50                  55                  60

Gln Gly Arg Val Thr Met Thr Arg Asp Thr Ser Ile Ser Thr Ile Tyr
```

```
                65                  70                  75                  80
Met Glu Leu Ser Ser Leu Lys Ser Glu Asp Thr Ala Val Tyr Phe Cys
                    85                  90                  95

Ala Arg Lys Ile Trp Val Gly Thr Thr Ile Phe Asp Tyr Trp Gly Gln
                100                 105                 110

Gly Thr Leu Val Thr Val Ser Ser
            115                 120

<210> SEQ ID NO 92
<211> LENGTH: 107
<212> TYPE: PRT
<213> ORGANISM: Artificial Sequence
<220> FEATURE:
<223> OTHER INFORMATION: synthetic peptide

<400> SEQUENCE: 92

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Ser Ile Tyr Arg Phe
                20                  25                  30

Leu Ser Trp Tyr Gln Gln Lys Pro Gly Thr Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Gly Pro Pro Leu
                85                  90                  95

Thr Phe Gly Gly Gly Thr Lys Val Gly Ile Arg
                100                 105

<210> SEQ ID NO 93
<211> LENGTH: 120
<212> TYPE: PRT
<213> ORGANISM: Artificial Sequence
<220> FEATURE:
<223> OTHER INFORMATION: synthetic peptide

<400> SEQUENCE: 93

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Asp Ile Asn His Gly Gly Ser Thr Asn Tyr Asn Pro Ser Leu Lys
        50                  55                  60

Ser Arg Val Ile Ile Ser Val Asp Thr Ser Lys Asn Gln Phe Ser Leu
65                  70                  75                  80

Lys Leu Ser Ser Val Thr Ala Ala Asp Thr Ala Leu Tyr Tyr Cys Ala
                85                  90                  95

Arg Gly Trp Gly Gly Gln Val Ala His Trp Phe Asp Pro Trp Gly Gln
                100                 105                 110

Gly Thr Leu Gly Thr Val Ser Ser
            115                 120

<210> SEQ ID NO 94
<211> LENGTH: 113
```

```
<212> TYPE: PRT
<213> ORGANISM: Artificial Sequence
<220> FEATURE:
<223> OTHER INFORMATION: synthetic peptide

<400> SEQUENCE: 94

Asp Ile Val Met Thr Gln Ser Pro Asp Ser Leu Ala Leu Ser Leu Gly
1               5                   10                  15

Glu Arg Ala Thr Ile Asn Cys Lys Ser Ser Gln Ser Val Leu Phe Ser
            20                  25                  30

Ser Asn Asn Gln Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Val Ser Ser Leu Gln Ala Glu Asp Val Ala Val Tyr Phe Cys Gln Gln
                85                  90                  95

Tyr Tyr Ser Leu Pro Tyr Thr Phe Gly Gln Gly Thr Lys Leu Glu Ile
            100                 105                 110

Lys

<210> SEQ ID NO 95
<211> LENGTH: 119
<212> TYPE: PRT
<213> ORGANISM: Artificial Sequence
<220> FEATURE:
<223> OTHER INFORMATION: synthetic peptide

<400> SEQUENCE: 95

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Ser Tyr
            20                  25                  30

Tyr Trp Ser Trp Ile Arg His Pro Pro Gly Lys Gly Leu Glu Trp Ile
        35                  40                  45

Gly Asp Ile Asn His Ser Gly Ser Thr Asn Tyr Asn Pro Ser Leu Lys
    50                  55                  60

Ser Arg Val Thr Leu Ser Val Asp Thr Ser Lys Asn Gln Phe Ser Leu
65                  70                  75                  80

Lys Val Thr Ser Val Thr Ala Ala Asp Thr Ala Val Tyr Tyr Cys Ala
                85                  90                  95

Arg Trp Gly Ile Ala Ala Asp Tyr Gly Met Asp Val Trp Gly Gln Gly
            100                 105                 110

Thr Thr Val Thr Val Ser Ser
        115

<210> SEQ ID NO 96
<211> LENGTH: 108
<212> TYPE: PRT
<213> ORGANISM: Artificial Sequence
<220> FEATURE:
<223> OTHER INFORMATION: synthetic peptide

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Asp Ser Gly Ser Gly Thr Asp Phe Thr Leu Thr Ile Ser Arg Leu Glu
 65                  70                  75                  80

Pro Glu Asp Phe Ala Leu Tyr Tyr Cys Gln Gln Tyr Gly Thr Ser Pro
                 85                  90                  95

Trp Thr Phe Gly Gln Gly Thr Lys Val Glu Ile Lys
            100                 105

<210> SEQ ID NO 97
<211> LENGTH: 122
<212> TYPE: PRT
<213> ORGANISM: Artificial Sequence
<220> FEATURE:
<223> OTHER INFORMATION: synthetic peptide

<400> SEQUENCE: 97

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Leu Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Thr Gly Leu Ser Thr Tyr Tyr Ala Asp Ser Leu
 50                  55                  60

Lys Gly Arg Phe Thr Ile Ser Arg Asp Ile Ser Lys Asn Thr Leu Tyr
 65                  70                  75                  80

Leu Gln Met Ser Ser Leu Lys Ala Glu Asp Thr Ala Val Tyr Tyr Cys
                 85                  90                  95

Ala Lys Gly Leu Glu Leu Phe Tyr Phe Tyr Tyr Gly Met Asp Val Trp
            100                 105                 110

Gly Gln Gly Thr Thr Val Thr Val Ser Ser
            115                 120

<210> SEQ ID NO 98
<211> LENGTH: 107
<212> TYPE: PRT
<213> ORGANISM: Artificial Sequence
<220> FEATURE:
<223> OTHER INFORMATION: synthetic peptide

<400> SEQUENCE: 98

Glu Ile Val Leu Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Leu Ala Val Tyr Tyr Cys Gln Gln Tyr Gly Arg Ser Leu
                 85                  90                  95

Ile Phe Gly Gln Gly Thr Arg Leu Glu Ile Lys
```

<210> SEQ ID NO 99
<211> LENGTH: 119
<212> TYPE: PRT
<213> ORGANISM: Artificial Sequence
<220> FEATURE:
<223> OTHER INFORMATION: synthetic peptide

<400> SEQUENCE: 99

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Ser Thr Ser Gly Arg Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Met Ala Val Tyr Tyr Cys
                85                  90                  95

Ala Ser Asp Tyr Tyr Asp Asn Val Gly Trp Asp Tyr Trp Gly Gln Gly
            100                 105                 110

Thr Leu Val Thr Val Ser Ser
        115

<210> SEQ ID NO 100
<211> LENGTH: 112
<212> TYPE: PRT
<213> ORGANISM: Artificial Sequence
<220> FEATURE:
<223> OTHER INFORMATION: synthetic peptide

<400> SEQUENCE: 100

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asp Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Ala His Trp Pro Arg Thr Phe Gly Gln Gly Thr Lys Val Glu Ile Lys
            100                 105                 110

<210> SEQ ID NO 101
<211> LENGTH: 119
<212> TYPE: PRT
<213> ORGANISM: Artificial Sequence
<220> FEATURE:
<223> OTHER INFORMATION: synthetic peptide

<400> SEQUENCE: 101

Leu Val Gln Leu Val Glu Ser Gly Gly Gly Leu Val Lys Pro Gly Gly
1               5                   10                  15

```
Ser Leu Arg Leu Ser Cys Thr Ala Ser Gly Ile Thr Phe Ser Asp Leu
            20                  25                  30

Tyr Met Ser Trp Ile Arg Gln Ser Pro Gly Lys Gly Leu Glu Trp Ile
        35                  40                  45

Ser Tyr Ile Ser Thr Ser Gly Arg Thr Ile Tyr Tyr Thr Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Arg Leu Arg Ala Asp Asp Thr Ala Val Tyr Tyr Cys
                85                  90                  95

Ala Gly Asp Tyr Tyr Asp Asn Ser Gly Trp Asp Tyr Trp Gly Arg Gly
            100                 105                 110

Thr Leu Val Thr Val Ser Ser
            115

<210> SEQ ID NO 102
<211> LENGTH: 112
<212> TYPE: PRT
<213> ORGANISM: Artificial Sequence
<220> FEATURE:
<223> OTHER INFORMATION: synthetic peptide

<400> SEQUENCE: 102

Asn Val Val Met Thr Gln Ser Pro Leu Ser Leu Pro Val Ala Leu Gly
1               5                   10                  15

Gln Pro Ala Ser Ile Ser Cys Arg Ser Gly Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asp Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Arg Thr Phe Gly Gln Gly Thr Lys Val Glu Ile Lys
            100                 105                 110

<210> SEQ ID NO 103
<211> LENGTH: 120
<212> TYPE: PRT
<213> ORGANISM: Artificial Sequence
<220> FEATURE:
<223> OTHER INFORMATION: synthetic peptide

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile His Trp Val Arg Gln Ala Ala Gly Gln Gly Leu Glu Trp Met
        35                  40                  45

Gly Trp Thr Asn Pro Asn Ser Gly Asn Ser Asp Tyr Ala Gln Lys Phe
    50                  55                  60

Gln Gly Arg Val Ser Met Thr Arg Asp Thr Ser Met Arg Thr Met Tyr
65                  70                  75                  80

Met Glu Leu Asn Ser Leu Arg Ser Glu Asp Thr Ala Val Tyr Phe Cys
```

```
                    85                  90                  95
Ala Arg Lys Ile Trp Val Gly Thr Thr Ile Phe Asp Tyr Trp Gly Gln
                100                 105                 110

Gly Thr Leu Val Thr Val Ser Ser
        115                 120

<210> SEQ ID NO 104
<211> LENGTH: 107
<212> TYPE: PRT
<213> ORGANISM: Artificial Sequence
<220> FEATURE:
<223> OTHER INFORMATION: synthetic peptide

<400> SEQUENCE: 104

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Ser Ile Tyr Arg Phe
            20                  25                  30

Leu Ser Trp Tyr Gln Gln Lys Pro Gly Thr Ala Pro Lys Leu Leu Ile
        35                  40                  45

Phe Ala Val Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu His Pro
65                  70                  75                  80

Glu Asp Phe Ala Ile Tyr Tyr Cys Gln Gln Ser Asp Ser Pro Pro Leu
                85                  90                  95

Thr Phe Gly Gly Gly Thr Lys Val Gly Ile Lys
                100                 105

<210> SEQ ID NO 105
<211> LENGTH: 357
<212> TYPE: DNA
<213> ORGANISM: Artificial Sequence
<220> FEATURE:
<223> OTHER INFORMATION: synthetic sequence

<400> SEQUENCE: 105
caggtgcagc tggtggagtc tgggggaggc ttggtcaagc ctggagggtc cctgagactc      60
tcctgtgcag cctctggatt caccttcagt gacctctaca tgagctggat ccgccaggct     120
ccagggaagg gactggagtg ggtttcatac attagtacta gtggtcgtac catatactac     180
gcagactctg tgaagggccg attcaccatc tccagggaca acgccaagaa ctcactgtat     240
ctacaaatga acagcctgag agccgaggac acggccgtgt attactgtgc gggcgactac     300
tatgacaata gtggttggga ctactggggc cggggaaccc tggtcaccgt ctcctca       357

<210> SEQ ID NO 106
<211> LENGTH: 337
<212> TYPE: DNA
<213> ORGANISM: Artificial Sequence
<220> FEATURE:
<223> OTHER INFORMATION: synthetic sequence

<400> SEQUENCE: 106
gatgttgtga tgactcagtc tccactctcc ctgcccgtca cccttggaca gccggcctcc      60
atctcctgca ggtctggtca aagcctcgta tacagtgatg gaaacaccta cttgaattgg     120
tttcagcaga ggccaggcca atctccaagg cgcctaattt ataaggtttc tgaccgggac     180
tctggggtcc cagacagatt cagcggcagc gggtcaggca ctgatttcac actgaaaatc     240
```

```
agcagggtgg aggctgagga tgttggggtt tattactgca tgcaaggtac acactggcct    300
cggacgttcg gccaagggac caaggtggaa atcaaac                             337

<210> SEQ ID NO 107
<211> LENGTH: 357
<212> TYPE: DNA
<213> ORGANISM: Artificial Sequence
<220> FEATURE:
<223> OTHER INFORMATION: synthetic sequence

<400> SEQUENCE: 107
caggtgcaac tggtggagtc tggggggaggc ttggtcaagc ctggagggtc cctgagactc   60
tcctgtgcag cctctgaaat caccttcagt gactactaca tgagctggat ccgccaggct   120
ccagggaagg gactggagtg gatttcatac attagtacta gtggtcgaac catatatttc   180
gcagactctg tgaagggccg attcaccatc tccagagaca acgccaagaa ttcactgtat   240
ctgcaaatga acagcctgag agccgatgac acggccgtgt attactgtgc gagcgatttt   300
tatgataata gtggttggga atactggggc caggaaccc tggtcaccgt ctcctca       357

<210> SEQ ID NO 108
<211> LENGTH: 337
<212> TYPE: DNA
<213> ORGANISM: Artificial Sequence
<220> FEATURE:
<223> OTHER INFORMATION: synthetic sequence

<400> SEQUENCE: 108
gatgttgtga tgactcagtc tccactctcc ctgtccgtca cccttggaca gccggcctcc    60
atctcctgca ggtctagtca aagcctcgta tacagtgatg gaaacaccta cttgaattgg    120
tttcagcaga ggccaggcca atctccaagg cgcctaattt ataaggtttc tgaccgggac    180
tctggggtcc cagacagatt cagcggcagt gggtcaggca ctgatttcac actgaaaatc    240
agcagggcgg aggctgagga tgttggggtt tattactgca tgcaaggtac acactggcct    300
cggacgttcg gccaagggac caaggtggaa atcaaac                             337

<210> SEQ ID NO 109
<211> LENGTH: 357
<212> TYPE: DNA
<213> ORGANISM: Artificial Sequence
<220> FEATURE:
<223> OTHER INFORMATION: synthetic sequence

<400> SEQUENCE: 109
caggtgcagt tggtggagtc tggggggaggc ttggtcaagc ctggagggtc cctgagactc   60
tcctgtgcag gctctggatt caccttcagt gaccactaca tgagctggat ccgccaggct   120
ccagggaagg ggctggagtg ggtttcatac attagtacta gtggtagaac catatactac   180
gcagactctg tgaagggccg attcaccatc tccaggaca acgccaagaa ctcactgtat    240
ctgcaaatga acagcctgag agccgaggac acggccgtgt attactgtgc gagcgattac   300
tatgataata gtggttggta ctactggggc cagggaaccc tggtcaccgt ctcctca      357

<210> SEQ ID NO 110
<211> LENGTH: 337
<212> TYPE: DNA
<213> ORGANISM: Artificial Sequence
<220> FEATURE:
<223> OTHER INFORMATION: synthetic sequence

<400> SEQUENCE: 110
```

```
gatgttgtga tgactcagtc tccactctcc ctgcccgtca cccttggaca gccggcctcc    60
atctcctgca ggtctagtca aagcctcgta tacagtgatg aaacaccta cttgaattgg   120 tttcagcaga ggccaggcca atctccaagg cgcctaattt ataaggtttc tgaccgggac   180
tctggggtcc cagacagatt cagcggcagt gggtcaggca ctgatttcac actgaaaatc   240
agtagggtgg aggctgagga tgttggggtt tattactgca tgcaaggtac acactggcct   300
cggacgttcg gccaagggac cacggtggaa atcaaac                            337
```

<210> SEQ ID NO 111
<211> LENGTH: 357
<212> TYPE: DNA
<213> ORGANISM: Artificial Sequence
<220> FEATURE:
<223> OTHER INFORMATION: synthetic sequence

<400> SEQUENCE: 111

```
caggtgcagt tggtggagtc tgggggaggc ttggtcaagc ctggagggtc cctgagactc    60
tcctgcgcag cctctggatt caccttcagt gaccactaca tgagttggat ccgccaggct   120
ccagggaagg ggctggagtg ggtgtcatac attagtacta gtggtagaac catatattat   180
gtagactctg tgaagggccg attcaccatc tccagggaca acgccaagaa ttcgttgtat   240
ctgcaaatga acagcctgag agccgaggac atggccgttt attactgtgc gagcgattac   300
tatgataatg ttggttggaa ctactgggc cagggagccc tggtcaccgt ctcctca       357
```

<210> SEQ ID NO 112
<211> LENGTH: 336
<212> TYPE: DNA
<213> ORGANISM: Artificial Sequence
<220> FEATURE:
<223> OTHER INFORMATION: synthetic sequence

<400> SEQUENCE: 112

```
gatgttgtgt tgactcagtc tccactctcc ctgcccgtca cccttggaca gccggcctcc    60
atctcctgca ggtctagtca aagcctcgta tacagtgatg aaacaccta cttgaattgg   120 tttcagcaga ggccaggcca atctccaagg cgcctaattt ataaggtttc tgaccgggac   180
tttggggtcc cagacagatt cagcggcagc ggatcaggca ctgatttcac actgaaaatc   240
agcagggtgg aggctgagga tgttgggatt tattactgca tgcaaggtac acactggccc   300
cggacgttcg gccaagggac caaggtggaa atcaaa                             336
```

<210> SEQ ID NO 113
<211> LENGTH: 357
<212> TYPE: DNA
<213> ORGANISM: Artificial Sequence
<220> FEATURE:
<223> OTHER INFORMATION: synthetic sequence

<400> SEQUENCE: 113

```
caggtgcagc tggtggagtc tgggggaggc ttggtcaagc ctggagggtc cctgagactc    60
tcctgtgcag cctctggatt caccttcagt gaccactaca tgagctggat ccgccaggct   120
ccagggaagg ggctggagtg ggtttcatac attagtacta gtggtagtac catatactac   180
gcagactctg tgaagggccg attcaccatc tccagggaca acgccaagaa ctcactgtat   240
ctacaaatga acagcctgag agccgaggac acggccgtgt attactgtgc gagcgattac   300
tatgataata gtggttggaa ctactgggc cagggaaccc tggtcaccgt ctcctca       357
```

<210> SEQ ID NO 114
<211> LENGTH: 337
<212> TYPE: DNA
<213> ORGANISM: Artificial Sequence
<220> FEATURE:
<223> OTHER INFORMATION: synthetic sequence

<400> SEQUENCE: 114

```
gatgttgtga tgactcagtc tccactctcc ctgcccgtca cccttggaca gccggcctcc      60
atctcctgca ggtctagtca aagcctcgta tacagtgatg gaaacaccta cttgaattgg     120
tttcagcaga ggccaggcca atctccaagg cgcctaattt ataaggtttc tgaccgggac     180
tctggggtcc cagacagatt cagcggcagc gggtcaggca ctgatttcac actgagaatc     240
agcagggtgg aagctgagga tgttggggtt tattactgca tgcaaggttc acactggcct     300
cggacgttcg gccaagggac caaggtggaa atcaaac                              337
```

<210> SEQ ID NO 115
<211> LENGTH: 357
<212> TYPE: DNA
<213> ORGANISM: Artificial Sequence
<220> FEATURE:
<223> OTHER INFORMATION: synthetic sequence

<400> SEQUENCE: 115

```
caggtgcagc tggtggagtc tgggggaggc ttggtcaagc ctggagggtc cctgagactc      60
tcctgtacag cctctggatt caccttcagt gaccactaca tgagttggat ccgccaggct     120
ccagggaagg ggctggagtg ggtttcatac attagtactg gtgtagaaac catatactac     180
gcagactctg tgaagggccg attcaccatc tccagggaca acgccaagaa ctcgctgtat     240
ctgcaaatga acagcctgag agccgaggac acggccgtat attactgtgc gagcgattac     300
tatgataatg ttggttggga ctactgggc cagggaaccc tggtcaccgt ctcctca        357
```

<210> SEQ ID NO 116
<211> LENGTH: 336
<212> TYPE: DNA
<213> ORGANISM: Artificial Sequence
<220> FEATURE:
<223> OTHER INFORMATION: synthetic sequence

<400> SEQUENCE: 116

```
gatgttgtgc tgactcagtc tccactctcc ctgcccgtca cccttggaca gccggcctcc      60
atctcctgca ggtctagtca aagcctcata tacagtgatg gaaacaccta cttgaattgg     120
tttcagcaga ggccaggcca atctccaagg cgcctaattt ataaggtttc tgaccgggac     180
tctggggtcc cagacagatt cagcggcagc gggtcaggca ctgatttcac actgaaaatc     240
agcagggtgg aggctgagga tgttggggtt tattactgca tgcaaggtac acactggcct     300
cggacgttcg gccaagggac caaggtggaa atcaaa                               336
```

<210> SEQ ID NO 117
<211> LENGTH: 357
<212> TYPE: DNA
<213> ORGANISM: Artificial Sequence
<220> FEATURE:
<223> OTHER INFORMATION: synthetic sequence

<400> SEQUENCE: 117

```
caggtgcagt tggtggagtc tgggggaggc ttggtcaagc ctggagggtc cctgagactc      60
tcctgcgcag gctctggatt caccttcagt gaccactata tgagttggat ccgccaggct    120
```

```
ccagggaagg ggctggagtg ggtgtcatat attagtacta gtggtagaac catattttat    180
gtagactctg tgaagggccg attcaccatc tccagggaca cgccaagaa ttcgttgtat     240 ctgcaaatga acagcctgag agccgaggac atggccgttt attactgtgc gagcgattat    300
tatgataatg ttggttggaa ttactggggc cagggagccc tggtcatcgt ctcctca      357
```

<210> SEQ ID NO 118
<211> LENGTH: 336
<212> TYPE: DNA
<213> ORGANISM: Artificial Sequence
<220> FEATURE:
<223> OTHER INFORMATION: synthetic sequence

<400> SEQUENCE: 118

```
gatgttgtgt tgactcagtc tccactctca ctgcccgtca cccttggaca gccggcctcc    60
atctcctgca ggtctagtca aagcctcgta tacagtgatg aaacaccta cttgaattgg    120 tttcagcaga ggccaggcca atctccaagg cgcctaattt ataaggtttc tgaccgggac   180
tttggggtcc cagacagatt cagcggcagc gggtcaggca ctgatttcac actgaaaatc   240
agcagggtgg aggctgagga tgttggggatt tattactgca tgcaaggtac acactggcct   300
cggacgttcg gccaagggac caaggtggaa atcaaa                              336
```

<210> SEQ ID NO 119
<211> LENGTH: 357
<212> TYPE: DNA
<213> ORGANISM: Artificial Sequence
<220> FEATURE:
<223> OTHER INFORMATION: synthetic sequence

<400> SEQUENCE: 119

```
caggtgcagc tggtggagtc tgggggaggc ttggtcaagc ctggagggtc cctgagactc    60
tcctgtgcag cctctggatt caccttcagt gacttctaca tgagttggat ccgccaggct   120
ccagggatgg gcctggagtg ggtttcatac attagtttta gtggtagggc catatactac   180
gcagactctg tgaggggccg attcaccatc tccagggaca cgccaagaa ttcactgtat   240 ctgcaaatga acagtctgag tgccgaggac acggccgtgt attactgtgc gagcgattac   300
tatgataatg ttggttggga ctactggggc ccgggaaccc tggtcaccgt ctcctca      357
```

<210> SEQ ID NO 120
<211> LENGTH: 336
<212> TYPE: DNA
<213> ORGANISM: Artificial Sequence
<220> FEATURE:
<223> OTHER INFORMATION: synthetic sequence

<400> SEQUENCE: 120

```
gatgttgtga tgactcagtc tccactctcc ctgcccgtca cccttggaca gccggcctcc    60
atctcctgca ggtctagtca aagcctcgtc tacagtgatg aaacaccta cttgaattgg   120 tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tattggggtt tattactgca tgcaaggtac acactggcct   300
cggacgttcg gccaagggac caaggtggaa atcaaa                              336
```

<210> SEQ ID NO 121
<211> LENGTH: 375
<212> TYPE: DNA

<213> ORGANISM: Artificial Sequence
<220> FEATURE:
<223> OTHER INFORMATION: synthetic sequence

<400> SEQUENCE: 121

| caggtgcagc | tgcaggagtc | gggcccagga | ctggtgaagc | cttcggagac | cctgtccctc | 60 |
| acctgcactg | tctctggtgg | ctccatcagt | agtaactact | ggaactggat | ccggcagccc | 120 |
| ccagggaagg | gactggagtg | gattggatat | atctattaca | gtgggagcac | caactacaac | 180 |
| ccctccctca | agagtcgagt | caccatatca | gtagacacgt | ccaagaacca | gttctccctg | 240 |
| aagctgagct | ctgtgaccgc | cgcagacacg | gccgtttatt | actgtgcgag | acggggttt | 300 |
| gagcagcagc | tgtcatacta | ctactactac | ggtttggacg | tctggggcca | agggaccacg | 360 |
| gtcaccgtct | cctca | | | | | 375 |

<210> SEQ ID NO 122
<211> LENGTH: 340
<212> TYPE: DNA
<213> ORGANISM: Artificial Sequence
<220> FEATURE:
<223> OTHER INFORMATION: synthetic sequence

<400> SEQUENCE: 122

| gacatcgtga | tgacccagtc | tccagactcc | ctggctgtgt | ctctgggcga | gagggccacc | 60 |
| gtcaactgca | agtccagcca | gagtgtttta | tacagctcca | acaataagaa | ctacttagct | 120 |
| tggtaccagc | agaaaccagg | acagcctcct | aaactactca | tttactgggc | atctacccgg | 180 |
| gaatccgggg | tccctgaccg | attcagtggc | agcgggtctg | ggacagattt | cactctcacc | 240 |
| atcagcagcc | tgcaggctga | agatgtggca | gattattact | gtcagcaata | ttatactttt | 300 |
| ccgtggacgt | tcggccaagg | gaccaaggtg | gaaatcaaac | | | 340 |

<210> SEQ ID NO 123
<211> LENGTH: 375
<212> TYPE: DNA
<213> ORGANISM: Artificial Sequence
<220> FEATURE:
<223> OTHER INFORMATION: synthetic sequence

<400> SEQUENCE: 123

| caggtgcagc | tgcaggagtc | gggcccagga | ctggtgaagc | cttcggagac | cctgtccctc | 60 |
| acctgcactg | tctctggtgg | ctccatcagt | agtaactact | ggagctggat | ccggcagccc | 120 |
| ccagggaagg | gactggagtg | gattgggtat | atctattaca | gtgggagcac | caactacaac | 180 |
| ccctccctca | agagtcgagt | caccatatca | gtagacacgt | ccaagaacca | gttctccctg | 240 |
| aagctgagct | ctgtgaccgc | cgcagacacg | gccgtgtatt | actgtgcgag | acggggttt | 300 |
| gagcagcagc | tgtcatacta | ctactactac | ggtatggacg | tctggggcca | agggaccacg | 360 |
| gtcaccgtct | cctca | | | | | 375 |

<210> SEQ ID NO 124
<211> LENGTH: 340
<212> TYPE: DNA
<213> ORGANISM: Artificial Sequence
<220> FEATURE:
<223> OTHER INFORMATION: synthetic sequence

<400> SEQUENCE: 124

| gacttcgtga | tgacccagtc | tccagactcc | ctggctgtgt | ctctgggcga | gagggccacc | 60 |
| atcaactgca | agtccagcca | gagtgtttta | tacagctcca | acaataagaa | ctacttagct | 120 |

```
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgtggacgt tcggccaagg gaccaaggtg gaaatcaagc                          340

<210> SEQ ID NO 125
<211> LENGTH: 361
<212> TYPE: DNA
<213> ORGANISM: Artificial Sequence
<220> FEATURE:
<223> OTHER INFORMATION: synthetic sequence

<400> SEQUENCE: 125
caggtgcagc tggtgcagtc tggggctgag gtgaagaagc ctggggcctc agtgaaggtc     60
tcctgcaagg cttctggata caccttcacc ttttatgata tcaactgggt gcgacaggcc    120
actggacaag gcttgagtg gatgggatgg atgaaccccta acagtggtaa cacaggctat    180
gcacagaact tccagggcag agtcaccatg accaggaaca cctccataaa cacagcctac    240
ttggaactga gcagcctgag atctgaggac acggccgttt attactgtgc gaggaaaatc    300
tgggtgggac atacgacctt tgaccgctgg ggccagggaa ccctggtcac cgtctcctca    360
g                                                                    361

<210> SEQ ID NO 126
<211> LENGTH: 322
<212> TYPE: DNA
<213> ORGANISM: Artificial Sequence
<220> FEATURE:
<223> OTHER INFORMATION: synthetic sequence

<400> SEQUENCE: 126
gccatccaga tgacccagtc tccatcctcc ctgtctgcat ctgtaggaga cagagtcacc     60
atcacctgcc gggcaagtca gagcattagt ggctatttaa attggtatca gcagaaacca    120
gggaaagccc ctaacctcct gatctatgct gcatccaatt tgcaaagtgg ggtcccatca    180
aggttcagtg gcagtggatc tgggacagat ttcactctca ccattagcag tctgcaacgt    240
gaagattttg caccttacta ctgtcaacag acttacaata ttccgttcac tttcggcgga    300
gggaccaagg tggagatcaa ac                                             322

<210> SEQ ID NO 127
<211> LENGTH: 360
<212> TYPE: DNA
<213> ORGANISM: Artificial Sequence
<220> FEATURE:
<223> OTHER INFORMATION: synthetic sequence

<400> SEQUENCE: 127
caggttcagc tggtgcaatc tggggctgag gtgaagaagc ctggggcctc agtgaaggtc     60
tcctgcaagg cttctggata caccttcacc aattatgata tcaactgggt gcgacaggcc    120
actggacaag gacttgagtg gatgggatgg gtgaacccta acagtggtaa ctcaggctat    180
gcacagaagt tccagggcag agtcaccatg accaggaca  cctccataag cacaatctac    240
atggagctga gcagcctgaa atctgaggac acggccgtct atttctgtgc gaggaagatc    300
tgggtgggaa ctacgatctt tgactactgg ggccagggaa ccctggtcac cgtctcctca    360

<210> SEQ ID NO 128
```

```
<211> LENGTH: 322
<212> TYPE: DNA
<213> ORGANISM: Artificial Sequence
<220> FEATURE:
<223> OTHER INFORMATION: synthetic sequence

<400> SEQUENCE: 128
gacatccaga tgacccagtc tccatcctcc ctgtctgcat ctgtgggaga cagagtcacc    60
atcgcttgcc gggcaagtca gagcatttac aggtttttaa gttggtatca gcagaaacca   120
gggacagccc ctaagctcct gatttatgct gcatccagtt tgcagagtgg ggtcccatca   180
aggttcagtg gcagtggatc tgggacagat tcactctca ccatcagcag tctgcaacct    240
gaagattttg caacttacta ctgtcaacag agtgacggtc ccccgctcac tttcggcgga   300
gggacaaagg tggggatcag gc                                            322

<210> SEQ ID NO 129
<211> LENGTH: 361
<212> TYPE: DNA
<213> ORGANISM: Artificial Sequence
<220> FEATURE:
<223> OTHER INFORMATION: synthetic sequence

<400> SEQUENCE: 129
caggtgcagc tacagcagtg gggcgcagga ctgttgaagc cttcggagac cctgtccctc    60
acctgcgctg tctatggtgg gtctttcagt ggttactact ggagctggat ccgccagccc   120
ccagggaagg ggctggagtg gattgggat atcaatcatg gtggaagcac caactacaac    180
ccgtccctca gagccgagt catcatttca gtagacacgt ccaagaacca gttctccctg    240
aagttgagtt ctgtgaccgc cgcggacacg gctttgtatt actgtgcgag aggctggggg   300
gggcaggtcg cccactggtt cgaccctgg ggccagggaa ccctgggcac cgtctcctca    360
g                                                                   361

<210> SEQ ID NO 130
<211> LENGTH: 340
<212> TYPE: DNA
<213> ORGANISM: Artificial Sequence
<220> FEATURE:
<223> OTHER INFORMATION: synthetic sequence

<400> SEQUENCE: 130
gacatcgtga tgacccagtc tccagactcc ctggctctgt ctctgggcga gagggccacc    60
atcaactgca gtccagcca gagtgttttta ttcagctcca ataatcagaa ctacttagct    120
tggtaccagc agaaaccagg acagcctcct aagctgctca tttactgggc atctacccgg   180
gaatccgggg tccctgaccg attcagtggc agcgggtctg ggacagattt cactctcacc    240
gtcagcagcc tgcaggctga agatgtggca gtttatttct gtcagcaata ttatagtctt   300
ccgtacactt ttggccaggg gaccaaactg gagatcaaac                         340

<210> SEQ ID NO 131
<211> LENGTH: 357
<212> TYPE: DNA
<213> ORGANISM: Artificial Sequence
<220> FEATURE:
<223> OTHER INFORMATION: synthetic sequence

<400> SEQUENCE: 131
caggtgcagc tacagcagtg gggcgcagga ctgttgaagc cttcggagac cctgtccctc    60
acctgcgctg tctttggtgg gtccttcagt agttactact ggagttggat ccgccacccc   120
```

```
ccagggaagg ggctggagtg gattggggac atcaatcata gtggaagcac caactacaac    180
ccgtccctca agagtcgcgt caccctatca gtagacacgt ccaagaatca gttctccctg    240
aaggtgacct ctgtgaccgc cgcggacacg gctgtgtatt actgtgcgag atggggaata    300
gcagcagact acgtatggga cgtctggggc caagggacca cggtcaccgt ctcctca       357
```

<210> SEQ ID NO 132
<211> LENGTH: 324
<212> TYPE: DNA
<213> ORGANISM: Artificial Sequence
<220> FEATURE:
<223> OTHER INFORMATION: synthetic sequence

<400> SEQUENCE: 132

```
gaaattgtat tgacgcagtc tccaggcacc ctgtctttgt ctccagggga aagagccacc    60
ctctcctgca gggccagtca gagtgttagc agcagctact tagcctggta tcagcaaaaa   120
cctggccagg ctcccaggct cctcatctat ggtgcatcca gcagggccac tggcatccca   180
gacaggttca gtgacagtgg gtctgggaca gacttcactc tcaccatcag tagactggag   240
ccggaagatt ttgcactata ttactgtcag cagtatggta cctcaccgtg gacgttcggc   300
caagggacca aggtggaaat caaa                                          324
```

<210> SEQ ID NO 133
<211> LENGTH: 366
<212> TYPE: DNA
<213> ORGANISM: Artificial Sequence
<220> FEATURE:
<223> OTHER INFORMATION: synthetic sequence

<400> SEQUENCE: 133

```
gaggtgcagt tgttggagtc tgggggaggc ttggtacagc ctggggggtc cctgagactc    60
tcctgtgcag cctctggatt cacccttagc acctatgcca tgagctgggt ccgccaggct   120
ccagggaagg ggctggagtg ggtctcagct attagtggta ctggtcttag cacatactac   180
gcagactccc tgaagggccg gttcaccatc tccagagaca tttccaagaa cacgctgtat   240
ctgcaaatga gcagcctgaa agccgaggac acggccgtat attactgtgc gaaaggtctg   300
gaacttttct acttctatta cggtatggac gtctggggcc aagggaccac ggtcaccgtc   360
tcctca                                                              366
```

<210> SEQ ID NO 134
<211> LENGTH: 321
<212> TYPE: DNA
<213> ORGANISM: Artificial Sequence
<220> FEATURE:
<223> OTHER INFORMATION: synthetic sequence

<400> SEQUENCE: 134

```
gagattgtgt tgacgcagtc tccaggcacc ctgtctttgt ctccagggga gagagccacc    60
ctctcctgca gggccagtca gagtgttagc agcacctact tagcctggta ccagcagaaa   120
cctggccagg ctcccaggct cctcatctat ggtacatcca gcagggccac tggcatccca   180
gacaggttca gtggcagtgg gtctgggaca gacttcactc tcaccatcag cagactggag   240
cctgaagatc ttgcagtgta ttactgtcag cagtatggta ggtcactcat cttcggccaa   300
gggacacgac tggagattaa a                                             321
```

<210> SEQ ID NO 135

<211> LENGTH: 357
<212> TYPE: DNA
<213> ORGANISM: Artificial Sequence
<220> FEATURE:
<223> OTHER INFORMATION: synthetic sequence

<400> SEQUENCE: 135

```
caggtgcagc tggtggagtc tgggggaggc ttggtcaagc ctggagggtc cctgagactc    60
tcctgtgcag cctctggatt caccttcagt gaccactaca tgagttggat ccgccaggct   120
ccagggaagg ggctggagtg ggtttcatac atcagtacta gtggtagaac catacactac   180
gcagactctg tgaagggccg attcaccatc tccaggaca acgccaagaa ttcgctttat    240
ctgcaaatga acagcctgag agccgaggac atggccgtat attactgtgc gagcgattac   300
tatgataatg ttggttggga ctactggggc cagggaaccc tggtcaccgt ctcctca      357
```

<210> SEQ ID NO 136
<211> LENGTH: 336
<212> TYPE: DNA
<213> ORGANISM: Artificial Sequence
<220> FEATURE:
<223> OTHER INFORMATION: synthetic sequence

<400> SEQUENCE: 136

```
gatgttgtga tgactcagtc tccactctcc ctgcccgtca cccttggaca gccggcctcc    60
atctcctgca ggtctagtca aagcctccta tacagtgatg aaacaccta cttgaattgg    120
tttcagcaga ggccaggcca atctccaagg cgcctaattt ataaggtttc tgaccgggac   180
tctggggtcc cagacagatt cagcggcagc gggtcaggca ctgatttcac actgaaaatc   240
agcagggtgg aggctgacga tgttggggtt tattactgca tgcaaggtgc acactggcct   300
cggacgttcg gccaagggac caaggtggaa atcaaa                             336
```

<210> SEQ ID NO 137
<211> LENGTH: 357
<212> TYPE: DNA
<213> ORGANISM: Artificial Sequence
<220> FEATURE:
<223> OTHER INFORMATION: synthetic sequence

<400> SEQUENCE: 137

```
ctggtgcagc tggtggagtc tgggggaggc ttggtcaagc ctggagggtc cctgagactc    60
tcctgtacag cctctggaat caccttcagt gacctctaca tgagctggat ccgccagtct   120
ccagggaaag gactggaatg gatttcatac attagtacta gtggtcgtac catatactac   180
acagactctg tgaagggccg attcaccatc tccaggaca acgccaagaa ctcactgttt    240
ctgcaaatga accgcctgag agccgacgac acggccgtgt attactgcgc gggcgactat   300
tatgataata gtggttggga ctactggggc cggggaaccc tggtcaccgt ctcctca      357
```

<210> SEQ ID NO 138
<211> LENGTH: 336
<212> TYPE: DNA
<213> ORGANISM: Artificial Sequence
<220> FEATURE:
<223> OTHER INFORMATION: synthetic sequence

<400> SEQUENCE: 138

```
aatgttgtga tgactcagtc tccactctcc ctgcccgtcg cccttggaca gccggcctcc    60
atctcctgca ggtctggtca aagcctcgta tacagtgatg aaacaccta cttgaattgg    120
tttcagcaga ggccaggcca atctccaagg cgcctaattt ataaggtctc tgaccgggac   180
```
tctggggtcc cagacagatt cagcggcagc gggtcaggca ctgatttcac actgaaaatc    240
agcagggtgg aggctgaaga tgttggaatt tattactgca tgcaaggtac acactggcct    300
cggacgttcg gccaagggac caaggtggaa atcaaa                              336

<210> SEQ ID NO 139
<211> LENGTH: 360
<212> TYPE: DNA
<213> ORGANISM: Artificial Sequence
<220> FEATURE:
<223> OTHER INFORMATION: synthetic sequence

<400> SEQUENCE: 139
caggttcagt tggtgcagtc tggggctgag gtgaagaagc ctggggcctc agtgaaggtc     60
tcctgcaagg cttctggata caccttcacc aattatgata tccactgggt gcgacaggcc    120
gctggacagg gacttgagtg gatgggatgg acgaacccga acagtggaaa ctcagactat    180
gcacagaaat tccagggcag agtcagtatg accaggdaca cctccatgag aacaatgtac    240
atggagctga acagcctgag atctgaggac acggccgtct atttctgtgc gcggaagatc    300
tgggtgggaa ctacgatctt tgactactgg ggccagggaa ccctggtcac cgtctcctca    360

<210> SEQ ID NO 140
<211> LENGTH: 321
<212> TYPE: DNA
<213> ORGANISM: Artificial Sequence
<220> FEATURE:
<223> OTHER INFORMATION: synthetic sequence

<400> SEQUENCE: 140
gacatccaga tgacccagtc tccatcctcc ctgtctgcat ctgtgggaga cagagtcacc     60
atcgcttgcc gggcaagtca gagtatttac aggtttttga gttggtatca gcagaaacca    120
gggacagccc ctaaactcct gatctttgct gtatccagtt tgcagagtgg ggtcccatca    180
aggttcagtg gcagtggatc tgggacagat ttcactctca ccatcagcag tctgcaccct    240
gaagattttg caatttacta ctgtcaacag agtgacagtc cccgctcac tttcggcgga    300 gggacaaagg tgggaatcaa g                                              321

<210> SEQ ID NO 141
<211> LENGTH: 354
<212> TYPE: PRT
<213> ORGANISM: JC polyomavirus

<400> SEQUENCE: 141

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

```
Ile Gly Val Thr Ser Leu Met Asn Val His Ser Asn Gly Gln Ala Thr
            115                 120                 125
His Asp Asn Gly Ala Gly Lys Pro Val Gln Gly Thr Ser Phe His Phe
            130                 135                 140
Phe Ser Val Gly Gly Glu Ala Leu Glu Leu Gln Gly Val Leu Phe Asn
145                 150                 155                 160
Tyr Arg Thr Lys Tyr Pro Asp Gly Thr Ile Phe Pro Lys Asn Ala Thr
                165                 170                 175
Val Gln Ser Gln Val Met Asn Thr Glu His Lys Ala Tyr Leu Asp Lys
            180                 185                 190
Asn Lys Ala Tyr Pro Val Glu Cys Trp Val Pro Asp Pro Thr Arg Asn
            195                 200                 205
Glu Asn Thr Arg Tyr Phe Gly Thr Leu Thr Gly Gly Glu Asn Val Pro
            210                 215                 220
Pro Val Leu His Ile Thr Asn Thr Ala Thr Thr Val Leu Leu Asp Glu
225                 230                 235                 240
Phe Gly Val Gly Pro Leu Cys Lys Gly Asp Asn Leu Tyr Leu Ser Ala
                245                 250                 255
Val Asp Val Cys Gly Met Phe Thr Asn Arg Ser Gly Ser Gln Gln Trp
            260                 265                 270
Arg Gly Leu Ser Arg Tyr Phe Lys Val Gln Leu Arg Lys Arg Arg Val
            275                 280                 285
Lys Asn Pro Tyr Pro Ile Ser Phe Leu Leu Thr Asp Leu Ile Asn Arg
            290                 295                 300
Arg Thr Pro Arg Val Asp Gly Gln Pro Met Tyr Gly Met Asp Ala Gln
305                 310                 315                 320
Val Glu Glu Val Arg Val Phe Glu Gly Thr Glu Glu Leu Pro Gly Asp
                325                 330                 335
Pro Asp Met Met Arg Tyr Val Asp Lys Tyr Gly Gln Leu Gln Thr Lys
            340                 345                 350
Met Leu
```